(12) United States Patent
Chang et al.

(10) Patent No.: US 7,101,509 B2
(45) Date of Patent: *Sep. 5, 2006

(54) REACTION VESSEL AND TEMPERATURE CONTROL SYSTEM

(75) Inventors: Ronald Chang, Redwood City, CA (US); Douglas B. Dority, Mill Valley, CA (US); Lee A. Christel, Palo Alto, CA (US); Kurt E. Petersen, San Jose, CA (US)

(73) Assignee: Cepheid, Sunnyvale, CA (US)

( * ) Notice: Subject to any disclaimer, the term of this patent is extended or adjusted under 35 U.S.C. 154(b) by 695 days.

This patent is subject to a terminal disclaimer.

(21) Appl. No.: 10/167,898

(22) Filed: Jun. 11, 2002

(65) Prior Publication Data

US 2002/0168299 A1    Nov. 14, 2002

Related U.S. Application Data

(63) Continuation-in-part of application No. 09/497,848, filed on Feb. 4, 2000, now Pat. No. 6,403,037.

(51) Int. Cl.
*G01N 15/06* (2006.01)
*G01N 21/00* (2006.01)
*G01N 1/10* (2006.01)
*G01N 21/03* (2006.01)
*B01L 3/02* (2006.01)

(52) U.S. Cl. .................. 422/68.1; 422/100; 422/58; 436/180; 436/165

(58) Field of Classification Search ................ 422/100, 422/68.1, 58, 59, 102; 436/180, 165

See application file for complete search history.

(56) References Cited

U.S. PATENT DOCUMENTS

| | | | |
|---|---|---|---|
| 3,708,886 A | | 1/1973 | Ogle |
| 3,937,614 A | | 2/1976 | Sodickson et al. |
| 4,192,429 A | | 3/1980 | Yerman |
| 4,207,394 A | | 6/1980 | Aldridge et al. |
| 4,301,117 A | | 11/1981 | Smernoff |
| 4,323,536 A | * | 4/1982 | Columbus .................... 422/56 |
| 4,396,579 A | | 8/1983 | Schroeder et al. |
| 4,426,451 A | * | 1/1984 | Columbus .................... 436/518 |
| 4,810,653 A | | 3/1989 | Helfer et al. |
| 4,902,624 A | | 2/1990 | Columbus et al. |
| 4,933,146 A | | 6/1990 | Meyer et al. |
| 5,026,526 A | | 6/1991 | Quenin et al. |
| 5,038,852 A | | 8/1991 | Johnson et al. |
| 5,077,017 A | | 12/1991 | Gorin et al. |
| 5,104,813 A | | 4/1992 | Besemer et al. |
| 5,333,675 A | | 8/1994 | Mullis et al. |
| 5,343,909 A | | 9/1994 | Goodman |
| 5,376,313 A | | 12/1994 | Kanewsked, III et al. |
| 5,460,780 A | | 10/1995 | Devaney, Jr. et al. |

(Continued)

*Primary Examiner*—Brian R. Gordon
(74) *Attorney, Agent, or Firm*—Townsend and Townsend and Crew LLP

(57) ABSTRACT

A reaction vessel has a reaction chamber, a loading reservoir connected to the reaction chamber via a first channel, and an aspiration port connected to the chamber via a second channel. To load the sample into the reaction chamber, the sample is dispensed into the loading reservoir and then drawn into the chamber by application of a vacuum to the aspiration port. A system for controlling the temperature of the sample in the reaction vessel includes one or more thermal elements for heating or cooling the sample and optionally optics for detecting one or more analytes in the sample.

82 Claims, 32 Drawing Sheets

U.S. PATENT DOCUMENTS

| | | |
|---|---|---|
| 5,589,136 A | 12/1996 | Northrup et al. |
| 5,652,149 A | 7/1997 | Mileaf et al. |
| 5,656,493 A | 8/1997 | Mullis et al. |
| 5,709,840 A | 1/1998 | Juranas |
| 5,711,917 A | 1/1998 | Juranas et al. |
| 5,721,136 A | 2/1998 | Finney et al. |
| 5,725,831 A * | 3/1998 | Reichler et al. ............... 422/56 |
| 5,783,148 A | 7/1998 | Cottingham et al. |
| 5,786,182 A | 7/1998 | Catanzariti |
| 5,811,296 A | 9/1998 | Chemelli et al. |
| 5,928,907 A | 7/1999 | Woudenberg et al. |
| 5,958,349 A | 9/1999 | Petersen et al. |
| 6,144,448 A | 11/2000 | Mitoma |
| 6,184,029 B1 | 2/2001 | Wilding et al. |
| 6,489,111 B1 * | 12/2002 | Takahashi et al. ............. 435/6 |
| 6,565,815 B1 * | 5/2003 | Yuan et al. .................. 422/198 |
| 6,660,228 B1 * | 12/2003 | Chang et al. ............... 422/68.1 |
| 2005/0112023 A1 * | 5/2005 | Liang .......................... 422/58 |

* cited by examiner

REACTION VESSEL AND TEMPERATURE CONTROL SYSTEM

CROSS-REFERENCES TO RELATED APPLICATIONS

This application is a continuation-in-part of commonly assigned, U.S. patent application Ser. No. 09/497,848, entitled "Reaction Vessel and Temperature Control System," filed Feb. 4, 2000, now U.S. Pat. No. 6,403,037, the entire disclosure of which is incorporated herein by reference.

FIELD OF THE INVENTION

This invention relates to a reaction vessel and temperature control system.

BACKGROUND OF THE INVENTION

There are many applications in the field of chemical processing in which it is desirable to precisely control the temperature of a sample, to induce rapid temperature changes in the sample, and to detect target analytes in the sample. Applications for such heat-exchanging chemical reactions may encompass organic, inorganic, biochemical or molecular reactions. Examples of thermal chemical reactions include isothermal nucleic acid amplification, thermal cycling nucleic acid amplification, such as the polymerase chain reaction (PCR), ligase chain reaction (LCR), self-sustained sequence replication, enzyme kinetic studies, homogeneous ligand binding assays, and more complex biochemical mechanistic studies that require complex temperature changes. Temperature control systems also enable the study of certain physiologic processes where a constant and accurate temperature is required.

One of the most popular uses of temperature control systems is for the performance of PCR to amplify a segment of nucleic acid. In this well known methodology, a DNA template is used with a thermostable DNA polymerase, nucleoside triphosphates, and two oligonucleotides with different sequences, complementary to sequences that lie on opposite strands of the template DNA and which flank the segment of DNA that is to be amplified ("primers"). The reaction components are cycled between a higher temperature (e.g., 95° C.) for dehybridizing double stranded template DNA, followed by lower temperatures (e.g., 40–60° C. for annealing of primers and 70–75° C. for polymerization). Repeated cycling between dehybridization, annealing, and polymerization temperatures provides exponential amplification of the template DNA.

Nucleic acid amplification may be applied to the diagnosis of genetic disorders; the detection of nucleic acid sequences of pathogenic organisms in a variety of samples including blood, tissue, environmental, air borne, and the like; the genetic identification of a variety of samples including forensic, agricultural, veterinarian, and the like; the analysis of mutations in activated oncogenes, detection of contaminants in samples such as food; and in many other aspects of molecular biology. Polynucleotide amplification assays can be used in a wide range of applications such as the generation of specific sequences of cloned double-stranded DNA for use as probes, the generation of probes specific for uncloned genes by selective amplification of particular segments of cDNA, the generation of libraries of cDNA from small amounts of mRNA, the generation of large amounts of DNA for sequencing and the analysis of mutations.

A preferred detection technique for chemical or biochemical analysis is optical interrogation, typically using fluorescence or chemiluminescence measurements. For ligand-binding assays, time-resolved fluorescence, fluorescence polarization, or optical absorption is often used. For PCR assays, fluorescence chemistries are often employed.

Some conventional instruments for conducting thermal reactions and for optically detecting the reaction products incorporate a block of metal having as many as ninety-six conical reaction tubes. The metal block is heated and cooled either by a Peltier heating/cooling apparatus or by a closed-loop liquid heating/cooling system in which liquid flows through channels machined into the block. Such instruments incorporating a metal block are described in U.S. Pat. No. 5,038,852 to Johnson and U.S. Pat. No. 5,333,675 to Mullis.

These conventional instruments have several disadvantages. First, due to the large thermal mass of a metal block, the heating and cooling rates in these instruments are limited, resulting in longer processing times. For example, in a typical PCR application, fifty cycles may require two or more hours to complete. With these relatively slow heating and cooling rates, some processes requiring precise temperature control are inefficient. For example, reactions may occur at the intermediate temperatures, creating unwanted and interfering side products, such as PCR "primer-dimers" or anomalous amplicons, which are detrimental to the analytical process. Poor control of temperature also results in over-consumption of expensive reagents necessary for the intended reaction.

Some of the instrumentation for newer processes requiring faster thermal cycling times has recently become available. One such device is disclosed by Northrup et al. in U.S. Pat. No. 5,589,136. The device includes a silicon-based, sleeve-type reaction chamber that combines heaters, such as doped polysilicon for heating, and bulk silicon for convection cooling. The device optionally includes a secondary tube (e.g., plastic) for holding the sample. In operation, the tube containing the sample is inserted into the silicon sleeve. Each sleeve also has its own associated optical excitation source and fluorescence detector for obtaining real-time optical data.

A different thermal cycling instrument is available from Idaho Technologies. This instrument employs forced-air heating and cooling of capillary sample carriers mounted in a carousel. The instrument monitors each capillary sample carrier in sequence as the capillary sample carriers are rotated past an optical detection site.

SUMMARY

The present invention provides an improved instrument and reaction vessel for thermally controlling and optically interrogating a sample. In preferred aspects, the system of the present invention permits convenient and effective loading of a sample into the reaction vessel, rapid heating and cooling of the sample, optimal thermal transfer between the sample and heating or cooling elements, and real-time optical detection and monitoring of the sample with increased detection sensitivity.

In accordance with an aspect of the present invention, a system for controlling the temperature of a sample comprises a reaction vessel having a reaction chamber defined by two opposing major walls and side walls connecting the major walls to each other. At least one of the major walls comprises a sheet or film. The vessel also has a loading reservoir for receiving the sample prior to loading the sample into the reaction chamber. The loading reservoir is connected to the reaction chamber via a first channel. The vessel further has an aspiration port connected to the reaction chamber via a second channel. The system also includes an aspiration device for establishing a seal with the aspiration port and for drawing the sample from the loading reservoir into the reaction chamber. The vessel further includes flow control means for preventing substantial flow of the sample from the loading reservoir into the reaction chamber until the sample is drawn into the chamber by the aspiration device. The system further includes at least one heating or cooling surface for contacting the sheet or film, the sheet or film being sufficiently flexible to conform to the surface. At least one thermal element heats or cools the surface to induce a temperature change in the reaction chamber.

In some embodiments, the flow control means comprises at least one portion of the first channel having a sufficiently small width or diameter to prevent substantial flow of the sample from the loading reservoir to the chamber until the sample is drawn into the chamber by the aspiration device. In some embodiments, the flow control means comprises at least one valve, membrane, or screen in the first channel.

In a specific embodiment, at least two of the side walls of the reaction chamber are optically transmissive, and the system further includes optics for optically interrogating the reaction chamber while the sheet or film is in contact with the heating or cooling surface. The optics comprise at least one light source for transmitting light to the chamber through a first one of the optically transmissive walls and at least one detector for detecting light exiting the chamber through a second one of the optically transmissive walls. The system also preferably comprises at least one controller for controlling the operation of the thermal element, light source, and detector.

In a specific embodiment, the system further comprises means for increasing the pressure in the reaction chamber. The pressure increase in the reaction chamber is sufficient to force the sheet or film to conform to the heating or cooling surface, ensuring optimal heat transfer to or from the reaction chamber. In some embodiments, the vessel further includes a seal aperture extending over an outer end of the loading reservoir and an outer end of the aspiration port, and the means for increasing the pressure in the chamber comprises a plug that is insertable into the aperture to compress gas in the vessel.

In accordance with another aspect of the invention, a system for controlling the temperature of a sample comprises a reaction vessel having a reaction chamber and having a loading reservoir for receiving the sample prior to loading the sample into the reaction chamber. The loading reservoir is connected to the reaction chamber via a first channel. The vessel also has an aspiration port connected to the reaction chamber via a second channel. The vessel further has a seal aperture extending over an outer end of the loading reservoir and an outer end of the aspiration port. The system also includes an aspiration device for establishing a seal with the aspiration port and for drawing the sample from the loading reservoir into the reaction chamber. The vessel includes flow control means for preventing substantial flow of the sample from the loading reservoir into the reaction chamber until the sample is drawn into the reaction chamber by the aspiration device. The system further includes a plug that is insertable into the aperture, after loading the sample into the reaction chamber, to simultaneously seal the loading reservoir, reaction chamber, and aspiration port from the external environment. At least one thermal element heats or cools the reaction chamber.

In a specific embodiment, the reaction chamber is defined by a plurality of walls, at least two of the walls being optically transmissive to provide optical windows to the reaction chamber, and the system further includes optics for optically interrogating the reaction chamber. The optics comprise at least one light source for transmitting light to the chamber through a first one of the optically transmissive walls and at least one detector for detecting light exiting the chamber through a second one of the optically transmissive walls. The system also preferably comprises at least one controller for controlling the operation of the thermal element, light source, and detector.

In accordance with another aspect of the invention, there is provided a system for loading a sample into a reaction vessel and for controlling the temperature of the sample in the vessel. The vessel includes a reaction chamber, a loading reservoir connected to the reaction chamber via a first channel, an aspiration port connected to the reaction chamber via a second channel, and a seal aperture extending over an outer end of the loading reservoir and an outer end of the aspiration port. The system comprises an aspiration and dispensing device for dispensing the sample into the loading reservoir, for establishing a seal with the aspiration port, and for drawing the sample from the loading reservoir into the reaction chamber. The vessel includes flow control means for preventing substantial flow of the sample from the loading reservoir into the reaction chamber until the sample is drawn into the reaction chamber by the aspiration and dispensing device. The system also comprises an automated machine for inserting a plug into the seal aperture after loading the sample into the chamber. The system further comprises one or more thermal elements for heating or cooling the reaction chamber.

In some embodiments, the reaction chamber is defined by a plurality of walls, at least two of the walls being optically transmissive, and the system further comprises optics for optically interrogating the chamber. The optics comprise at least one light source for transmitting light to the chamber through a first one of the optically transmissive walls and at least one detector for detecting light exiting the chamber through a second one of the optically transmissive walls. The system also preferably includes at least one controller for controlling the operation of the thermal element, light source, and detector.

In accordance with another aspect of the invention, a reaction vessel comprises a reaction chamber defined by two opposing major walls and side walls connecting the major walls to each other. At least one of the major walls comprises a sheet or film sufficiently flexible to conform to a heating or cooling surface. At least two of the side walls are optically transmissive to provide optical windows to the reaction chamber. The vessel also has a loading reservoir for receiving the sample prior to loading the sample into the reaction chamber. The loading reservoir is connected to the reaction chamber via a first channel. The vessel further includes an aspiration port for establishing a seal with an aspiration device. The aspiration port is connected to the reaction chamber via a second channel, thereby enabling the aspiration device to draw the sample from the loading reservoir into the chamber. The vessel also includes flow control means for preventing substantial flow of the sample from the loading reservoir into the reaction chamber until the sample is drawn into the reaction chamber by the aspiration device.

In some embodiments, the flow control means comprises at least one portion of the first channel having a sufficiently small width or diameter to prevent substantial flow of the sample from the loading reservoir to the chamber until the sample is drawn into the chamber by the aspiration device. In some embodiments, the flow control means comprises at least one valve, membrane, or screen in the first channel.

In accordance with another aspect of the invention, a reaction vessel comprises a reaction chamber and a loading reservoir for receiving the sample prior to loading the sample into the reaction chamber. The loading reservoir is connected to the reaction chamber via a first channel. The vessel also has an aspiration port for establishing a seal with an aspiration device, the aspiration port being connected to the reaction chamber via a second channel thereby enabling the aspiration device to draw the sample from the loading reservoir into the reaction chamber. The vessel further includes flow control means for preventing substantial flow of the sample from the loading reservoir into the reaction chamber until the sample is drawn into the reaction chamber by the aspiration device. The vessel also comprises first and second plugs for sealing the loading reservoir and the aspiration port, respectively, and for compressing gas in the vessel, thereby increasing pressure in the reaction chamber.

In accordance with another aspect of the invention, a reaction vessel comprises a reaction chamber and a loading reservoir for receiving the sample prior to loading the sample into the reaction chamber. The loading reservoir is connected to the reaction chamber via a first channel. The vessel also has an aspiration port for establishing a seal with an aspiration device, the aspiration port being connected to the reaction chamber via a second channel, thereby enabling the aspiration device to draw the sample from the loading reservoir into the reaction chamber. The vessel further includes flow control means for preventing substantial flow of the sample from the loading reservoir into the reaction chamber until the sample is drawn into the reaction chamber by the aspiration device. The vessel also has a seal aperture, extending over an outer end of the loading reservoir and an outer end of the aspiration port, for receiving a plug that is inserted into the aperture after loading the sample into the reaction chamber.

In some embodiments, the system of the present invention is configured as a small hand-held instrument, and in other embodiments, as a large instrument with multiple reaction sites for simultaneously processing hundreds of samples. In high throughput embodiments, the heating and/or cooling elements and optics are preferably disposed in a single housing to form an independently controllable, heat-exchanging module with detection capability. The system includes a base instrument for receiving a plurality of such modules, and the base instrument includes processing electronics for independently controlling the operation of each module. Each module provides a reaction site for thermally processing a sample contained in a reaction vessel and for detecting one or more target analytes (e.g., nucleic acid sequences of interest) in the sample. The system may also include a computer for controlling the base instrument.

DETAILED DESCRIPTION

The present invention provides a reaction vessel and system for thermally controlling and optically interrogating a sample. The sample may be a solution or suspension containing particles, cells, microorganisms, ions, or small and large molecules, such as proteins and nucleic acids, etc. In a particular use, the sample may be a bodily fluid (e.g., blood, urine, saliva, sputum, seminal fluid, spinal fluid, mucus, or other bodily fluids). Alternatively, the sample may be a solid made soluble or suspended in a liquid or the sample may be an environmental sample such as ground or waste water, soil extracts, or pesticide residues. Further, the sample may be mixed with one or more chemicals, reagents, diluents, or buffers. The term "sample" is understood to encompass original samples of interest (e.g., bodily fluids), samples containing at least parts of original samples, and reaction products resulting from reactions of original samples.

In a preferred embodiment, the system includes a reaction vessel for holding the sample and a heat-exchanging module into which the vessel is inserted for thermal processing and optical detection. The heat-exchanging module includes a pair of opposing plates between which the vessel is inserted for thermal processing, one or more heating or cooling elements for heating or cooling the plates, and optics for optically interrogating the sample contained in the vessel. The system also includes a base unit with processing electronics for receiving a plurality of such heat-exchanging modules and for independently controlling each module. The system may also include a controller, such as a personal computer or network computer, that provides a user interface to the system and controls the operation of the base unit. The system is useful for performing heat-exchanging chemical reactions, such as nucleic acid amplification, and for detecting target analytes.

Figure 1:
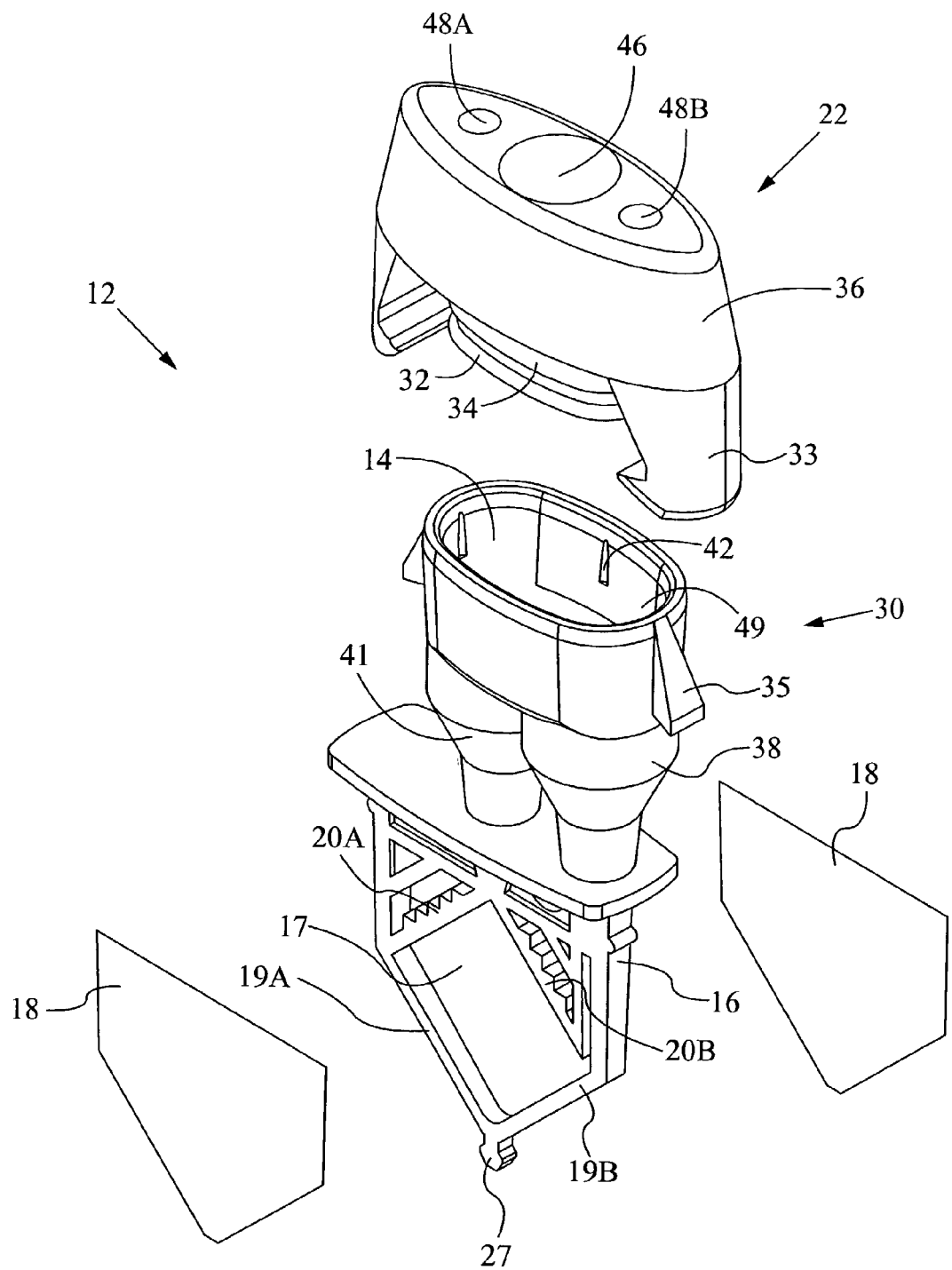
FIG. 1 is a partially exploded, isometric view of a reaction vessel having a reaction chamber. The major walls of the reaction chamber are removed, for illustrative purposes, to show the interior of the chamber.
Figure 2A:
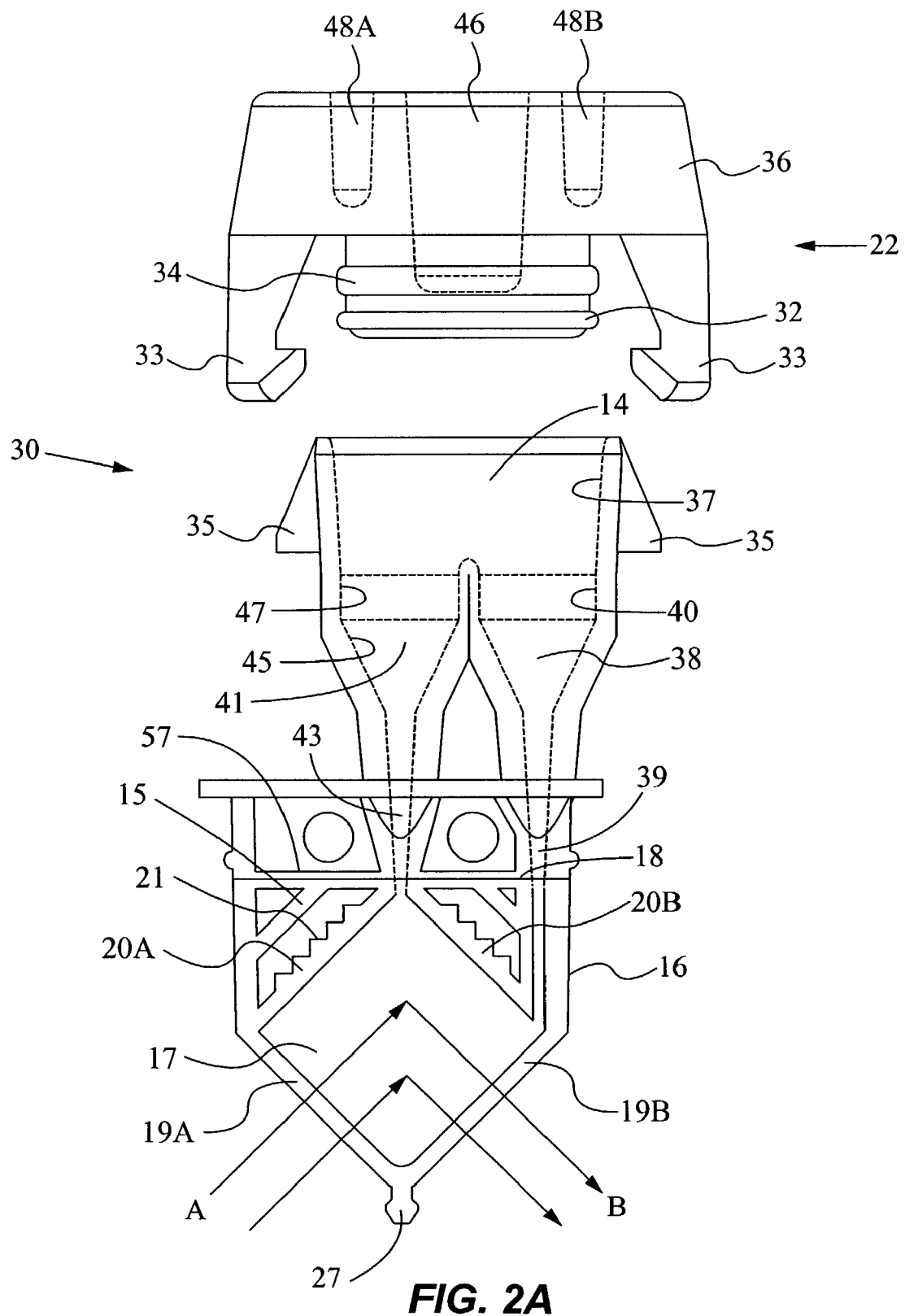
FIG. 2A is a schematic, front view of the vessel of FIG. 1.

FIGS. 1–23D illustrate a preferred embodiment. FIG. 1 shows a partially exploded view of a reaction vessel 12 according to the preferred embodiment, and FIG. 2A shows a front view of the vessel 12. The vessel 12 has a body defining a reaction chamber 17. The chamber 17 holds a sample for thermal processing and optical interrogation. The reaction vessel 12 includes a rigid frame 16 that defines the side walls 19A, 19B, 20A, 20B of the chamber 17. The vessel also includes thin, flexible sheets or films attached to opposite sides of the rigid frame 16 to form two opposing major walls 18 of the chamber. (The major walls 18 are shown in FIG. 1 exploded from the rigid frame 16 for illustrative purposes). The reaction chamber 17 is thus defined by the two opposing major walls 18, attached to opposite sides of the frame 16, and the rigid side walls 19A, 19B, 20A, 20B that connect the major walls 18 to each other.

The major walls 18 facilitate optimal thermal conductance to the sample contained in the chamber 17. Each of the walls 18 is sufficiently flexible to contact and conform to a respective heating or cooling surface, thus providing for optimal thermal contact and heat transfer between the heating or cooling surface and the sample contained in the chamber 17. Furthermore, the flexible walls 18 continue to conform to the surfaces if the shape of the surfaces changes due to thermal expansion or contraction during the course of the heat-exchanging operation.

Figure 4:
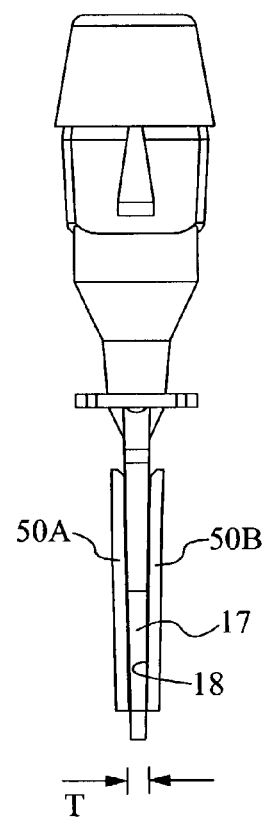
FIG. 4 is a side view of the vessel of FIG. 1 inserted into a thermal sleeve formed by opposing plates.

As shown in FIG. 4, the heating or cooling surfaces for contacting the flexible walls 18 are preferably formed by a pair of opposing plates 50A, 50B positioned to receive the chamber 17 between them. When the chamber 17 of the vessel is inserted between the plates 50A, 50B, the inner surfaces of the plates contact the walls 18 and the flexible walls conform to the surfaces of the plates. The plates are preferably spaced a distance from each other equal to the thickness T of the chamber 17 as defined by the thickness of the frame 16. In this position, minimal or no gaps are found between the plate surfaces and the walls 18. The plates may be heated and cooled by various thermal elements to induce temperature changes within the chamber 17, as is described in greater detail below.

The walls 18 are preferably flexible films of polymeric material such as polypropylene, polyethylene, polyester, or other polymers. The films may either be layered, e.g., laminates, or the films may be homogeneous. Layered films are preferred because they generally have better strength and structural integrity than homogeneous films. In particular, layered polypropylene films are presently preferred because polypropylene is not inhibitory to PCR. Alternatively, the walls 18 may comprise any other material that may be formed into a thin, flexible sheet and that permits rapid heat transfer. For good thermal conductance, the thickness of each wall 18 is preferably between about 0.003 to 0.5 mm, more preferably between 0.01 to 0.15 mm, and most preferably between 0.025 to 0.08 mm.

Referring again to FIGS. 1–2A, the reaction vessel 12 also includes a loading structure 30 extending from the frame 16 for loading the sample into the chamber 17. The loading structure 30 is preferably integrally formed (e.g., molded in one piece) with the frame 16. The loading structure 30 defines a loading reservoir 38 in fluid communication with the chamber 17. The loading reservoir 38 receives the sample prior to loading the sample into the chamber 17. The loading reservoir preferably has a volume capacity equal to or greater than the volume capacity of the chamber 17. The loading reservoir 38 is connected to the chamber 17 by an inlet channel 39. The loading structure 30 also defines an aspiration port 41 connected to the chamber 17 by an outlet channel 43. The aspiration port 41 has tapered walls 45 for establishing a seal with an aspiration and dispensing device (e.g., a pipette), thereby enabling the device to draw the sample from the loading reservoir 38, through the channel 39, and into the chamber 17. In general, the aspiration and dispensing device may comprise a pipette, syringe, probe, luer fitting, or any other device capable of aspirating and dispensing a fluid.

The reaction vessel preferably includes flow control means for preventing substantial flow of the sample from the loading reservoir 38 to the reaction chamber 17 until the sample is drawn into the chamber 17 by the aspiration device. As used herein, the phrase "substantial flow of the sample" is intended to mean flow of at least 50% of the sample. The flow control means should be sufficient to prevent at least 50% of the sample from flowing from the loading reservoir 38 into the chamber 17 for the time period beginning when the sample is dispensed into the loading reservoir 38 and ending when the sample is drawn into the chamber 17 by the aspiration device (typically a time period in the range of 3 to 60 seconds). In most applications, the sample is drawn into the chamber 17 only a few seconds after loading the sample into the loading reservoir 38. In other applications, however, the sample may be held in the loading reservoir 38 for longer periods of time while additional liquids or materials are added to the loading reservoir 38 (e.g., reagents, probes, additional sample material). The additional liquids or materials are mixed with the sample in the loading reservoir 38, and then the mixture is drawn into the chamber 17.

Figure 2B:
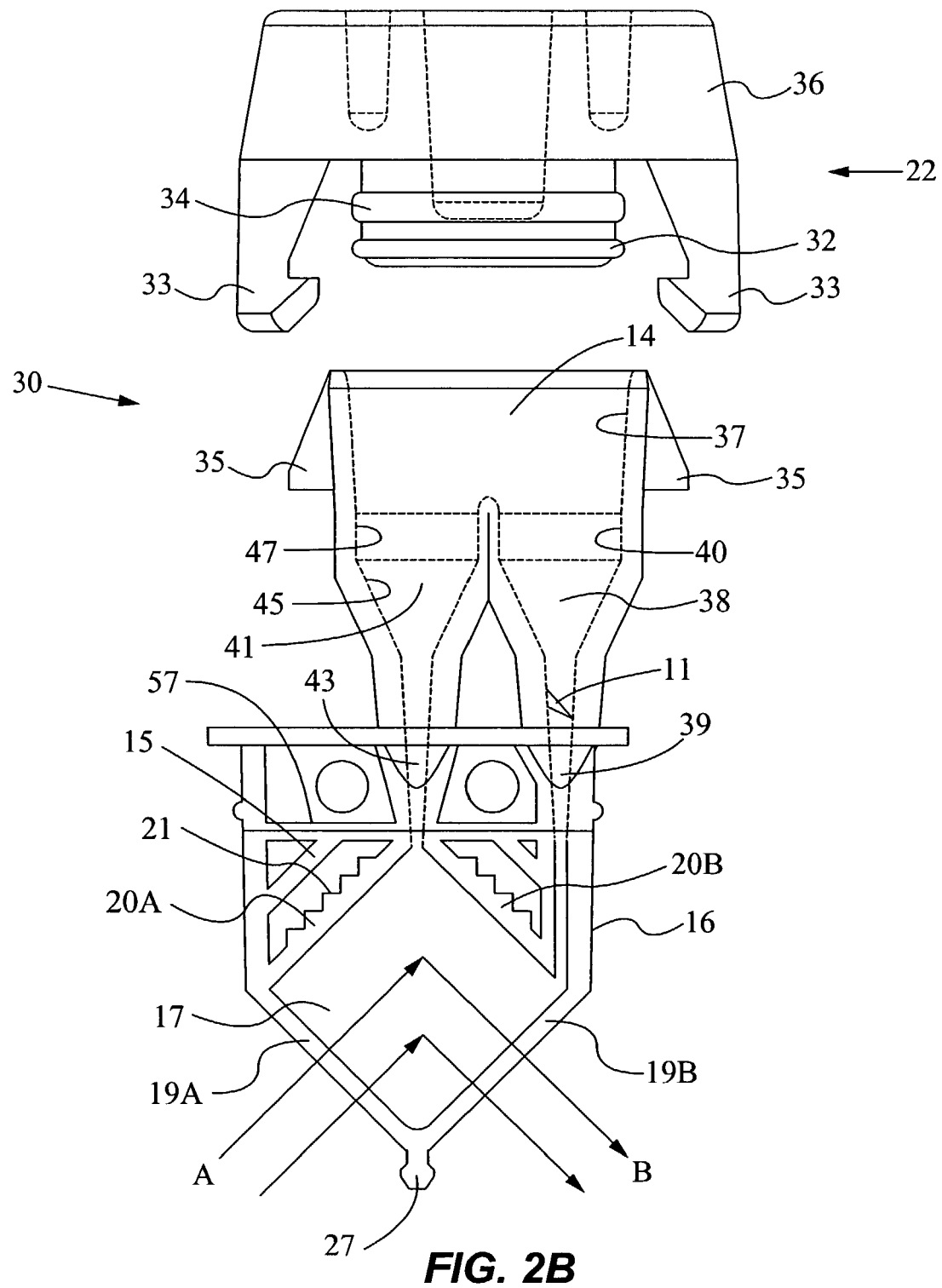
FIG. 2B is a schematic, front view of a reaction vessel having a valve.
Figure 2C:
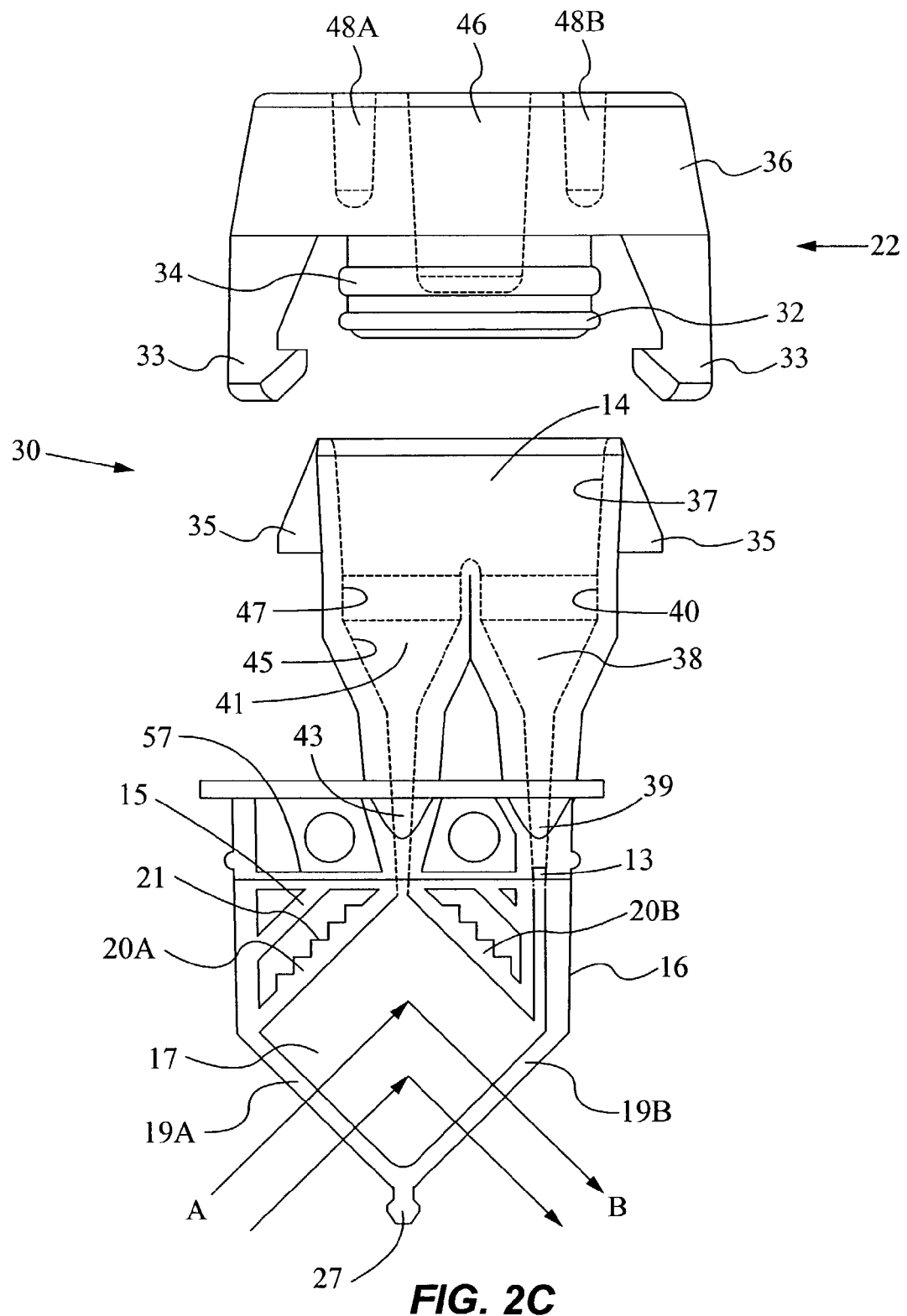
FIG. 2C is a schematic, front view of a reaction vessel having a membrane or screen.

Suitable flow control means include, but are not limited to: a channel having a narrow width or diameter; one or more valves; one or more membranes; or one or more screens. FIG. 2A shows one embodiment of the vessel in which the flow control means is at least one portion of the inlet channel 39 having a sufficiently small width or diameter (e.g., 0.031 inches or less is suitable for most aqueous solutions having the viscosity of water) to prevent substantial flow of the sample (e.g., due to gravitational force) from the loading reservoir 38 to the chamber 17 until the sample is drawn into the chamber by the aspiration device. FIG. 2B shows another embodiment of the vessel in which the flow control means is a valve 11 in the channel 39. There are many types of valves known in the art that are suitable for this purpose including, e.g., a flap valve, check valve, or rotary valve. FIG. 2C shows another embodiment of the vessel in which the flow control means is a membrane or screen 13 in the channel 39. Suitable membranes include, e.g., burstable or piercable membranes that are burst or pierced to permit fluid flow through the channel 39. If a screen is used as the flow control component, the screen should have a pore size sufficient to prevent substantial flow of the sample before a vacuum is applied to the aspiration port 41 and permit flow of the sample when the vacuum is applied.

The flow control permits simple and accurate metering of the volume of sample loaded into the chamber 17. For example, accurate loading of the sample into the chamber 17 may be performed as follows. A volume of sample equal to the volume capacity of the chamber 17 (e.g., 100 microliters) is initially placed in the loading reservoir 38 using a pipette. The pipette is then inserted into the aspiration port 41 and used to suck the same amount of air (e.g., 100 microliters) out of the chamber 17, so that the correct volume of sample is sucked from the loading reservoir 38 into the chamber 17 to precisely fill the chamber. Alternatively, the volume of sample loaded into the chamber 17 may be monitored visually, optically, or electronically.

Referring again to FIGS. 1–2A, the loading structure 30 also defines a seal aperture 14 that extends over the outer end of the loading reservoir 38 and over the outer end of the aspiration port 41. The vessel 12 includes a plug 22 that is inserted into the aperture 14 after filling the chamber 17 with the sample. The plug 22 seals the aperture 14, and thus simultaneously seals the chamber 17, loading reservoir 38, and aspiration port 41 from the environment external to the vessel 12. The plug 22 also compresses gas in the vessel 12, thereby increasing pressure in the chamber 17 and outwardly expanding the flexible walls 18. The gas compressed by the plug 22 is typically air filling the aperture 14, loading reservoir 38, and aspiration port 41. The pressurization of the chamber 17 is important because the pressure increase in the chamber forces the walls 18 against the surfaces of the plates 50A, 50B (see FIG. 4) and ensures that the walls 18 fully contact and conform to the inner surfaces of the plates, thus guaranteeing optimal thermal conductance between the plates 50A, 50B and the chamber 17.

The plug may comprise any device capable of establishing a seal with the walls of the aperture 14 and of compressing gas in the vessel 12. Such devices include, but are not limited to, pistons, plungers, or stoppers. The plug 22 of the preferred embodiment includes a sealing ring 32 and a stabilizer ring 34. When the plug 22 is inserted into the aperture 14, the sealing ring 32 establishes an annular seal with the inner walls 37 of the aperture 14 and compresses air in the aperture. The stabilizer ring 34 maintains the plug 22 in coaxial alignment with the aperture 14 as the plug is inserted into the aperture. The plug 22 also includes a cap 36 having latches 33. The vessel 12 includes corresponding catches 35 extending from the sides of the loading structure 30. When the plug 22 is inserted into the aperture 14, the catches 35 engage the latches 33, thereby securing the plug in the aperture. As shown in FIG. 1, the plug 22 and aperture 14 are preferably oval in shape to give the vessel 12 a slim profile. The slim profile enables multiple vessels to be spaced closely to each other (e.g., standard 9 mm spacing between vessels). It is to be understood, however, that the plug 22 and aperture 14 may have any shape desired, e.g., circular, square, rectangular, etc.

Figure 24A:
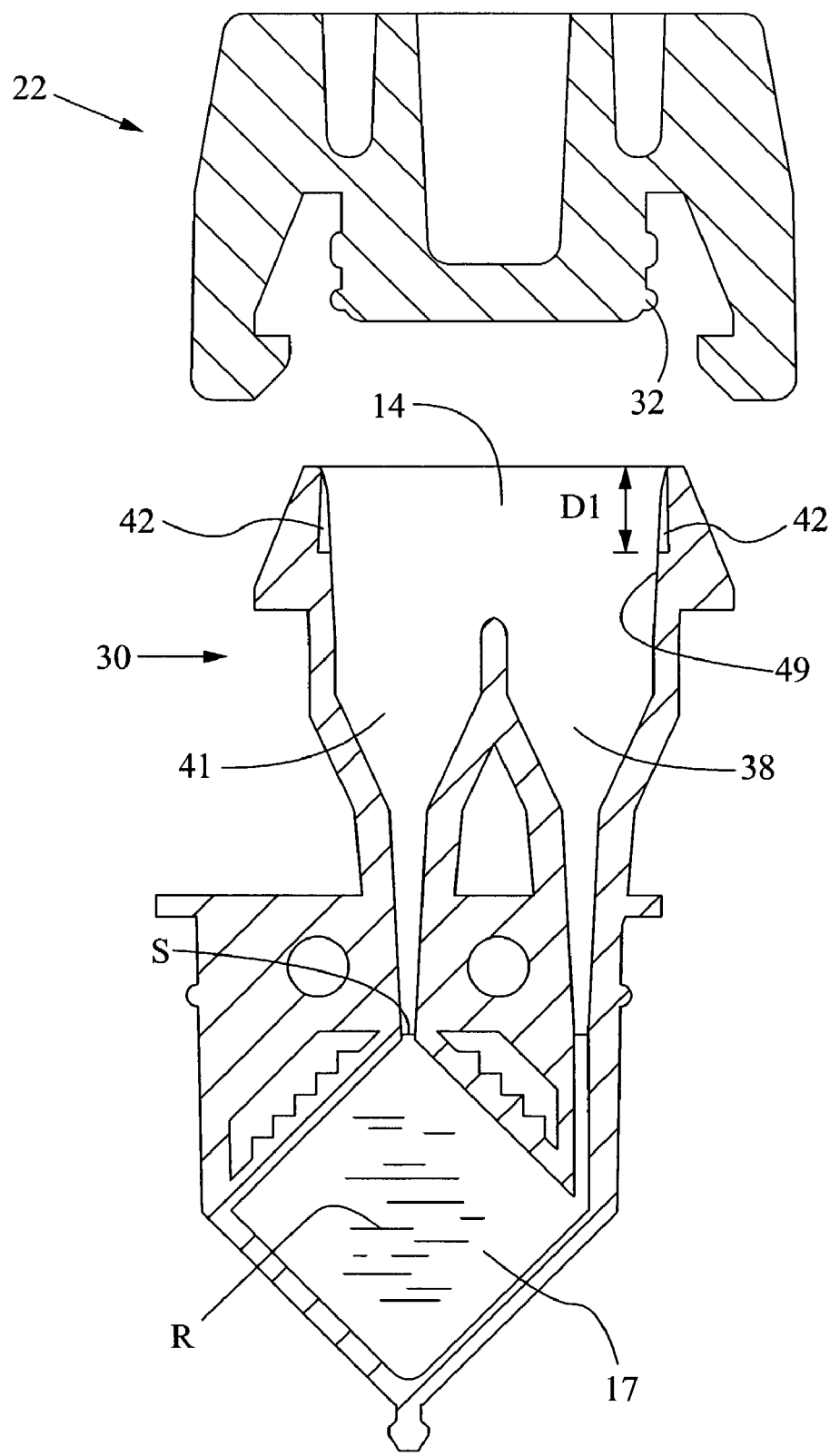
FIGS. 24A–24B are schematic, cross-sectional views of a plug being inserted into an aperture of the vessel of FIG. 1.

The loading structure 30 has an inner surface 49 defining the aperture 14. The inner surface 49 may optionally have one or more pressure control grooves 42 formed therein. In the preferred embodiment, the inner surface has four pressure control grooves (only two visible in the isometric view of FIG. 1) spaced equidistantly about the circumference of the aperture 14. Referring now to FIG. 24A, the pressure control grooves 42 extend to a predetermined depth $D_1$ in the aperture 14. The grooves 42 allow gas to escape from the aperture 14 and thus prevent pressurization of the chamber 17 until the sealing ring 32 reaches the depth $D_1$ in the aperture. When the sealing ring 32 reaches the depth $D_1$, the sealing ring establishes an annular seal with the surface 49 and begins to compress air trapped in the aperture 14, loading reservoir 38, and aspiration port 41. The compression of the trapped air causes the desired pressurization of the chamber 17.

Figure 24B:
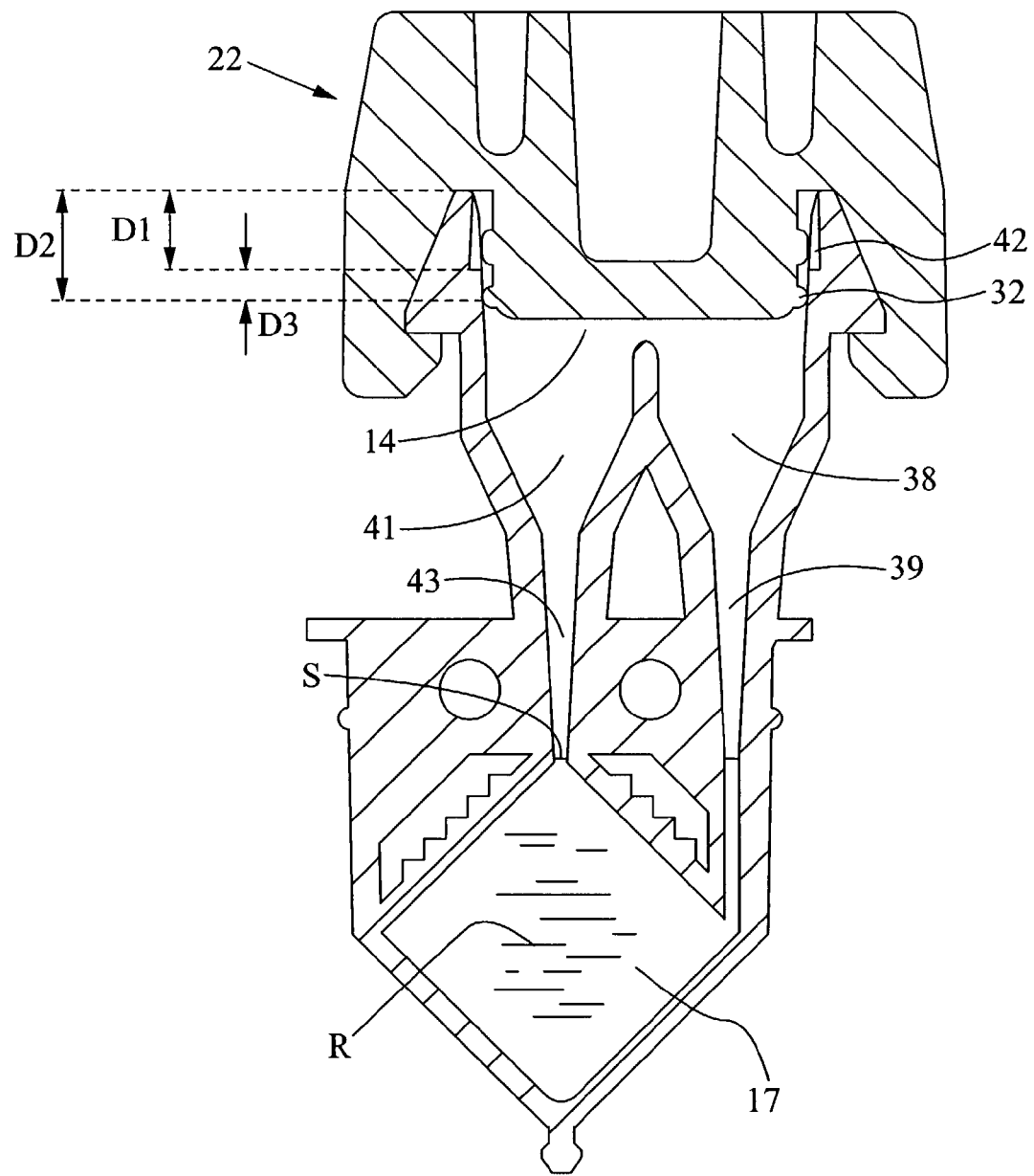

The insertion of the plug 22 into the aperture 14 is illustrated in FIGS. 24A–24B. As shown in FIG. 24A, prior to inserting the plug 22 into the aperture 14, the chamber 17 is filled with a reaction mixture R, typically the sample mixed with one or more reagents. Specific methods for filling the chamber 17 are discussed in detail below. The reaction mixture R fills the vessel 12 to a liquid surface level S. Also prior to inserting the plug 22 into the aperture 14, the aperture 14 contains air having pressure equal to the pressure of the atmosphere external to the vessel, hereinafter called ambient pressure. The ambient pressure is usually standard atmospheric pressure, e.g., about 14.7 pounds per square inch (psi). When the plug 22 is first inserted into the aperture 14, the sealing ring 32 begins to displace the air in the aperture. The displaced air escapes from the aperture 14 through the pressure control grooves 42.

Referring now to FIG. 24B, when the sealing ring 32 reaches the depth $D_1$ at which the pressure control grooves end, the sealing ring 32 establishes an annular seal with the walls of the aperture 14 and begins to compress air trapped in the vessel between the sealing ring 32 and the surface level S of the reaction mixture. The reaction mixture is usually a liquid and therefore substantially incompressible by the plug. The air trapped in the vessel 12, however, may be compressed to increase pressure in the chamber 17. As the plug 22 is inserted further into the aperture 14, the ring 34 keeps the plug 22 coaxially aligned with the aperture 14 as the sealing ring 32 continues to compress air.

When the plug 22 is fully inserted, the sealing ring 32 seals the aperture 14 at a depth $D_2$ which is lower than the depth $D_1$ at which the pressure control grooves 42 terminate.

The distance $D_3$ traveled by the sealing ring 32 between depths $D_1$ and $D_2$, i.e. the distance of the pressure stroke, determines the amount of pressurization of the chamber 17. Referring again to FIG. 4, the pressure in the chamber 17 should be sufficiently high to ensure that the flexible major walls 18 of the chamber outwardly expand to contact and conform to the inner surfaces of the plates 50A, 50B. The pressure should not be so great, however, that the flexible walls 18 burst, become unattached from the rigid frame 16, or deform the frame or plates.

It is presently preferred to pressurize the chamber 17 to a pressure in the range of 2 to 50 psi above ambient pressure. This range is presently preferred because 2 psi is generally enough pressure to ensure conformity between the flexible walls 18 and the surfaces of the plates 50A, 50B, while pressures above 50 psi may cause bursting of the walls 18 or deformation of the frame 16 or plates 50A, 50B. More preferably, the chamber 17 is pressurized to a pressure in the range of 8 to 15 psi above ambient pressure. This range is more preferred because it is safely within the practical limits described above, i.e. pressures of 8 to 15 psi are usually more than enough to ensure that the flexible walls 18 contact and conform to the surfaces of the plates 50A, 50B, but are significantly lower than the pressures that might burst the walls 18 or deform the frame 16.

Referring again to FIG. 24B, the desired pressurization of the chamber 17 may be achieved by proper design of the plug 22, aperture 14, and pressure control grooves 42 and by use of the equation:

$$P_1 * V_1 = P_2 * V_2;$$

where:

$P_1$ is equal to the pressure in the vessel 12 prior to insertion of the plug 22;

$V_1$ is equal to the volume capacity of the vessel between the liquid surface level S and the depth $D_1$ to which the pressure control grooves 42 extend;

$P_2$ is equal to the desired final pressure in the chamber 17 after insertion of the plug 22 into the aperture 14; and $V_2$ is equal to the volume capacity of the vessel between the liquid surface level S and the depth $D_2$ at which the sealing ring 32 establishes a seal with the walls of the aperture 14 when the plug 22 is fully inserted into the vessel.

To ensure the desired pressurization $P_2$ of the chamber 17, one should size the aperture 14 and pressure stroke distance $D_3$ such that the ratio of the volumes $V_1:V_2$ is equal to the ratio of the pressures $P_2:P_1$. An engineer having ordinary skill in the art will be able to select suitable values for the volumes $V_1$ and $V_2$ using the description and equation given above. For example, in the presently preferred embodiment, the initial pressure $P_1$ in the vessel is equal to standard atmospheric pressure of about 14.7 psi, the volume $V_1$ is equal to 500 l, the depth $D_1$ is equal to 0.2 inches, the depth $D_2$ is equal to 0.34 inches to give a pressure stroke distance $D_3$ of 0.14 inches, and the volume $V_2$ is equal to 275 l to give a final pressure $P_2$ of about 26.7 psi (the desired 12 psi above ambient pressure). This is just one example of suitable dimensions for the vessel 12 and is not intended to limit the scope of the invention. Many other suitable values may be selected.

In selecting suitable dimensions for the aperture 14 and pressure stroke distance $D_3$ (and thus the volumes $V_1$, $V_2$), there is no theoretical limit to how large or small the dimensions may be. It is only important that the ratio of the volumes $V_1:V_2$ yield the desired final desired pressure $P_2$ in the chamber. As a practical matter, however, it is presently preferred to design the vessel such that the distance $D_3$ of the pressure stroke is at least 0.05 inches, i.e., so that the plug 22 when fully inserted into the aperture 14 extends to a depth $D_2$ that is at least 0.05 inches below the depth $D_1$ at which the pressure control grooves end. This minimum length of the pressure stroke is preferred to reduce or make negligible the effect that any manufacturing or operating errors may have on the pressurization of the chamber. For example, the length of the pressure stroke may differ slightly from vessel to vessel due to manufacturing deviations, or the volume of air compressed may vary due to operator error in filling the vessel (e.g., different fill levels). If the vessel is designed to have a sufficiently long pressure stroke, however, such variances will have a lesser or negligible effect on the ratio of volumes $V_1:V_2$ and suitable pressurization of the chamber will still occur.

In addition, to provide a safety margin for manufacturing or operator errors, one should select a pressure stroke sufficient to achieve a final pressure $P_2$ that is safely higher (e.g., at least 3 psi higher) than the minimum pressure needed to force the flexible walls of the chamber against the inner surfaces of the plates. With such a safety margin, any deviations in the final pressure due to manufacturing deviations or errors in filling the chamber will have a negligible effect and suitable pressurization of the chamber 17 will still occur. As stated above, the plunger stroke is preferably designed to increase pressure in the chamber 17 to a pressure in the range of 8 to 15 psi above ambient pressure to provide the safety margin.

The pressure control grooves 42 provide several advantages. First, the pressure control grooves 42 provide a simple mechanism for precisely and accurately controlling the pressure stroke of the plug 22, and hence the pressurization of the chamber 17. Second, the pressure control grooves 42 allow the plug 22 to become fully aligned with the aperture 14 before the pressure stroke begins and thus prevent the plunger from becoming misaligned or cocked in the channel. This ensures a highly consistent pressure stroke. Although it is possible for the vessel to have only one pressure control groove, it is preferable for the vessel to have multiple pressure control grooves (e.g., 2 to 6 grooves) spaced equidistantly about the circumference of the aperture 14. Referring again to FIG. 24A, the pressure control grooves 42 preferably cut about 0.01 to 0.03 inches into the surface 49 defining the aperture 14. This range is preferred so that the pressure control grooves 42 are large enough to allow air to escape from the aperture 14, but do not cut so deeply into the surface 41 that they degrade the structural integrity of the loading structure 30.

Although the pressure control grooves 42 are advantageous, they are not a mandatory feature of the vessel 12. It is possible to construct the vessel 12 without the pressure control grooves and still achieve the desired pressurization of the chamber 17. Embodiments in which the vessel lacks pressure control grooves are intended to fall within the scope of the present invention. In embodiments in which the vessel lacks pressure control grooves, the pressure stroke of the plug 22 begins when the sealing ring 32 enters the aperture 14 and establishes a seal with the walls of the aperture. In these embodiments, the volume $V_1$ (for use in the equation above) is equal to the volume capacity of the vessel 12 between the liquid surface level S and the top of the loading structure 30 where the sealing ring 32 first establishes a seal with the inner surface 49.

Referring again to FIG. 2A, the vessel 12 also preferably includes optical windows for in situ optical interrogation of the sample in the chamber 17. In the preferred embodiment, the optical windows are the side walls 19A, 19B of the rigid frame 16. The side walls 19A, 19B are optically transmissive to permit the transmission of light to the chamber 17 through the side wall 19A and detection of light exiting the chamber 17 through the side wall 19B. Arrows A represent illumination beams entering the chamber 17 through the side wall 19A and arrows B represent emitted light (e.g., fluorescent emission from labeled analytes in the sample) exiting the chamber 17 through the side wall 19B.

The side walls 19A, 19B are preferably angularly offset from each other. It is usually preferred that the walls 19A, 19B are offset from each other by an angle of about 90°. A 90° angle between excitation and detection paths assures that a minimum amount of excitation radiation entering through the wall 19A will exit through wall 19B. In addition, the 90° angle permits a maximum amount of emitted light, e.g fluorescence, to be collected through wall 19B. The walls 19A, 19B are preferably joined to each other to form a "V" shaped intersection at the bottom of the chamber 17. Alternatively, the angled walls 19A, 19B need not be directly joined to each other, but may be separated by an intermediary portion, such as another wall or various mechanical or fluidic features which do not interfere with the thermal and optical performance of the vessel. For example, the walls 19A, 19B may meet at a port which leads to another processing area in communication with the chamber 17, such as an integrated capillary electrophoresis area. In the presently preferred embodiment, a locating tab 27 extends from the frame 16 below the intersection of walls 19A, 19B. The locating tab 27 is used to properly position the vessel 12 in a heat-exchanging module described below with reference to FIG. 6.

Optimum optical sensitivity may be attained by maximizing the optical path length of the light beams exciting the labeled analytes in the sample and the emitted light that is detected, as represented by the equation:

$$I_o/I_i = C * L * A,$$

where $I_o$ is the illumination output of the emitted light in volts, photons or the like, C is the concentration of analyte to be detected, $I_i$ is the input illumination, L is the path length, and A is the intrinsic absorptivity of the dye used to label the analyte.

Figure 3:
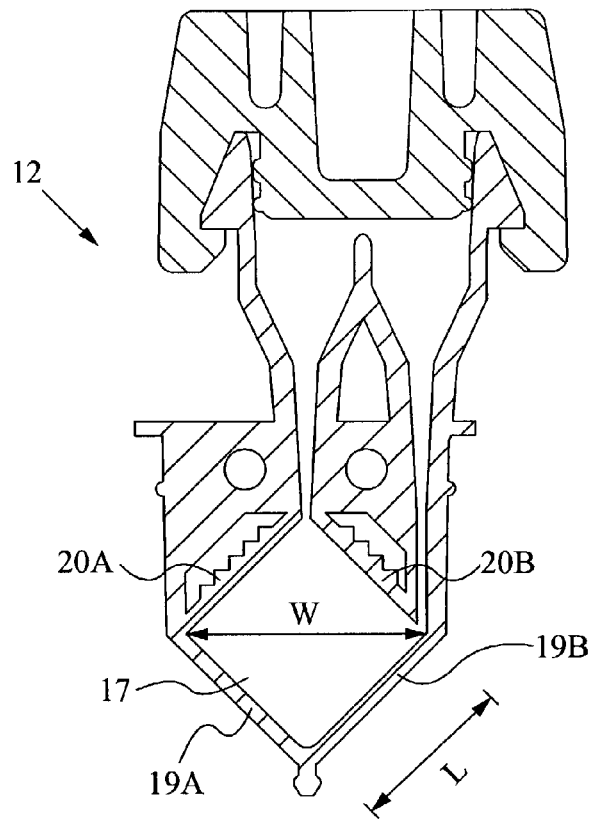
FIG. 3 is another front view of the vessel of FIG. 1.

The thin, flat reaction vessel 12 of the present invention optimizes detection sensitivity by providing maximum optical path length per unit analyte volume. Referring to FIGS. 3–4, the vessel 12 is preferably constructed such that each of the sides walls 19A, 19B, 20A, 20B of the chamber 17 has a length L in the range of 1 to 15 mm, the chamber has a width W in the range of 1.4 to 20 mm, the chamber has a thickness T in the range of 0.5 to 5 mm, and the ratio of the width W of the chamber to the thickness T of the chamber is at least 2:1. These parameters are presently preferred to provide a vessel having a relatively large average optical path length through the chamber, i.e. 1 to 15 mm on average, while still keeping the chamber sufficiently thin to allow for extremely rapid heating and cooling of the sample contained therein. The average optical path length of the chamber 17 is the distance from the center of the side wall 19A to the center of the chamber 17 plus the distance from the center of the chamber 17 to the center of the side wall 19B. The thickness T of the chamber 17 is defined by the thickness of the sides walls 19A, 19B, 20A, 20B.

More preferably, the vessel 12 is constructed such that each of the sides walls 19A, 19B, 20A, 20B of the chamber 17 has a length L in the range of 5 to 12 mm, the chamber has a width W in the range of 7 to 17 mm, the chamber has a thickness T less than or equal to 3 mm, and the ratio of the width W of the chamber to the thickness T of the chamber is at least 4:1. These ranges are more preferable because they provide a vessel having both a larger average optical path length (i.e., 5 to 12 mm) and volume capacity (i.e., 10 to 430 microliters) while still maintaining a chamber sufficiently thin to permit extremely rapid heating and cooling of a sample. The relatively large volume capacity provides for increased sensitivity in the detection of low concentration analytes, such as nucleic acids.

In the presently preferred embodiment, the reaction vessel 12 has a diamond-shaped chamber 17 defined by the side walls 19A, 19B, 20A, 20B, each of the side walls has a length of about 10 mm, the chamber has a width of about 14 mm, the chamber has a thickness T of 1 mm as defined by the thickness of the frame 16, and the chamber has a volume capacity of about 100 microliters. This reaction vessel provides a relatively large average optical path length of 10 mm through the chamber 17. Additionally, the thin chamber allows for extremely rapid heating and/or cooling of the sample contained therein. The diamond-shape of the chamber 17 helps prevent air bubbles from forming in the chamber as it is filled with the sample and also aids in optical interrogation of the sample.

The frame 16 is preferably made of an optically transmissive material, e.g., a polycarbonate or clarified polypropylene, so that the side walls 19A, 19B are optically transmissive. As used herein, the term optically transmissive means that one or more wavelengths of light may be transmitted through the walls. In the preferred embodiment, the optically transmissive walls 19A, 19B are substantially transparent. In addition, one or more optical elements may be present on the optically transmissive side walls 19A, 19B. The optical elements may be designed, for example, to maximize the total volume of solution which is illuminated by a light source, to focus excitation light on a specific region of the chamber 17, or to collect as much fluorescence signal from as large a fraction of the chamber volume as possible. In alternative embodiments, the optical elements may comprise gratings for selecting specific wavelengths, filters for allowing only certain wavelengths to pass, or colored lenses to provide filtering functions. The wall surfaces may be coated or comprise materials such as liquid crystal for augmenting the absorption of certain wavelengths. In the presently preferred embodiment, the optically transmissive walls 19A, 19B are substantially clear, flat windows having a thickness of about 1 mm.

As shown in FIG. 2, the side walls 20A, 20B preferably includes reflective faces 21 which internally reflect light trying to exit the chamber 17 through the side walls 20A, 20B. The reflective faces 21 are arranged such that adjacent faces are angularly offset from each other by about 90°. In addition, the frame 16 defines open spaces between the side walls 20A, 20B and support ribs 15. The open spaces are occupied by ambient air that has a different refractive index than the material composing the frame (e.g., plastic). Due to the difference in the refractive indexes, the reflective faces 21 are effective for internally reflecting light trying to exit the chamber 17 through the walls 20A, 20B and provide for increased detection of optical signal through the walls 19A, 19B. In the preferred embodiment, the optically transmissive side walls 19A, 19B define the bottom portion of the diamond-shaped chamber 17, and the retro-reflective side walls 20A, 20B define the top portion of the chamber.

The reaction vessel 12 may be used in manual operations performed by human technicians or in automated operations performed by machines, e.g. pick-and-place machines. As shown in FIG. 2, for automated embodiments, the cap 36 preferably includes a tapered engagement aperture 46 for receiving and establishing a fit with a robotic arm or machine tip (not shown in FIG. 2), thus enabling the machine tip to pick and place the plug 22 into the aperture 14. The engagement aperture 46 preferably has tapered side walls for establishing a friction fit with the machine tip. Alternatively, the engagement aperture 46 may be designed to establish a vacuum fit with the machine tip. The cap 36 may optionally include alignment apertures 48A, 48B used by the machine tip to properly align the cap 36 as the plug 22 is inserted into the aperture 14.

A preferred method for fabricating the reaction vessel 12 will now be described with reference to FIGS. 1–2A. The reaction vessel 12 may be fabricated by first molding the rigid frame 16 and the loading structure 30 using known injection molding techniques. The frame 16 and loading structure 30 are preferably molded as a single piece of polymeric material, e.g., clarified polypropylene. The channel 39 is preferably produced with at least one narrow cross-sectional dimension to control fluid flow as previously described. In embodiments in which the vessel includes a valve 11 in the channel 39 (FIG. 2B) or screen or membrane 13 in the channel 39 (FIG. 2C), the valve or membrane can also be integrally molded in one piece with the frame 16 and loading structure 30. This one-piece molding technique is suitable for forming a flap valve or piercable or burstable membrane in the channel 39. Alternatively, the vessel can be insert molded by placing a valve, screen, or membrane in the mold and molding the frame and loading structure around the inserted piece to produce a vessel with a valve, screen, or membrane in the channel 39. Alternatively, a valve, screen, or membrane may simply be inserted into the channel 39 after molding the frame 16 and loading structure 30.

Referring again to FIGS. 1–2A, after the frame and loading structure are produced, thin, flexible sheets are cut to size and sealed to opposite sides of the frame 16 to form the major walls 18 of the chamber 17. The major walls 18 are preferably cast or extruded films of polymeric material, e.g., polypropylene films, that are cut to size and attached to the frame 16 using the following procedure. A first piece of film is placed over one side of the bottom portion of the frame 16. The frame 16 preferably includes a tack bar 57 (FIG. 2) for aligning the top edge of the film. The film is placed over the bottom portion of the frame 16 such that the top edge of the film is aligned with the tack bar 57 and such that the film completely covers the bottom portion of the frame 16 below the tack bar 57. The film should be larger than the bottom portion of the frame 16 so that it may be easily held and stretched flat across the frame. The film is then cut to size to match the outline of the frame by clamping to the frame the portion of the film that covers the frame and cutting away the portions of the film that extend past the perimeter of the frame using, e.g., a laser or die. The film is then tack welded to the frame, preferably using a laser.

The film is then sealed to the frame 16, preferably by heat sealing. Heat sealing is presently preferred because it produces a strong seal without introducing potential contaminants to the vessel as the use of adhesive or solvent bonding techniques might do. Heat sealing is also simple and inexpensive. At a minimum, the film should be completely sealed to the surfaces of the side walls 19A, 19B, 20A, 20B. More preferably, the film is additionally sealed to the surfaces of the support ribs 15 and tack bar 57. The heat sealing may be performed using, e.g., a heated platen. An identical procedure may be used to cut and seal a second sheet to the opposite side of the frame 16 to form the other major wall of the chamber 17.

Many variations to this fabrication procedure are possible. For example, in an alternative embodiment, the film is stretched across the bottom portion of the frame 16 and then sealed to the frame prior to cutting the film to size. After sealing the film to the frame, the portions of the film that extend past the perimeter of the frame are cut away using, e.g., a laser or die. Although it is presently preferred to mold the frame 16 as a single piece, it is also possible to fabricate the frame from multiple pieces. For example, the side walls 19A, 19B forming the angled optical windows may be molded from polycarbonate, which has good optical transparency, while the rest of the frame is molded from polypropylene, which is inexpensive and compatible with PCR. The separate pieces can be attached together in a secondary step. For example, the side walls 19A, 19B may be press-fitted and/or bonded to the remaining portion of the frame 16. The flexible walls 18 may then be attached to opposite sides of the frame 16 as previously described.

The plug 22 is preferably produced using known injection molding techniques. In the preferred embodiment, the plug 22 is molded as a one-piece part of elastomeric material. Suitable elastomers from which the plug may be molded include thermalplastic elastomers (e.g., Santoprene® commercially available from the Monsanto Company of St. Louis, Mo.). Alternatively, the plug 22 may be produced by molding a plastic body and placing an elastomeric ring (e.g., an o-ring) around the plastic body to form the sealing ring 32.

Referring again to FIG. 4, the plates 50A, 50B may be made of various thermally conductive materials including ceramics or metals. Suitable ceramic materials include aluminum nitride, aluminum oxide, beryllium oxide, and silicon nitride. Other materials from which the plates may be made include, e.g., gallium arsenide, silicon, silicon nitride, silicon dioxide, quartz, glass, diamond, polyacrylics, polyamides, polycarbonates, polyesters, polyimides, vinyl polymers, and halogenated vinyl polymers, such as polytetrafluoroethylenes. Other possible plate materials include chrome/aluminum, superalloys, zircaloy, aluminum, steel, gold, silver, copper, tungsten, molybdenum, tantalum, brass, sapphire, or any of the other numerous ceramic, metal, or polymeric materials available in the art.

Ceramic plates are presently preferred because their inside surfaces may be conveniently machined to very high smoothness for high wear resistance, high chemical resistance, and good thermal contact to the flexible walls of the reaction vessel. Ceramic plates can also be made very thin, preferably between about 0.5 and 1 mm, for low thermal mass to provide for extremely rapid temperature changes. A plate made from ceramic is also both a good thermal conductor and an electrical insulator, so that the temperature of the plate may be well controlled using a resistive heating element coupled to the plate.

Various thermal elements may be employed to heat and/or cool the plates 50A, 50B and thus control the temperature of the sample in the chamber 17. In general, suitable heating elements for heating the plate include conductive heaters, convection heaters, or radiation heaters. Examples of conductive heaters include resistive or inductive heating elements coupled to the plates, e.g., resistors or thermoelectric devices. Suitable convection heaters include forced air heaters or fluid heat-exchangers for flowing fluids past the plates. Suitable radiation heaters include infrared or microwave heaters. Similarly, various cooling elements may be used to cool the plates. For example, various convection cooling elements may be employed such as a fan, Peltier device, refrigeration device, or jet nozzle for flowing cooling fluids past the surfaces of the plates. Alternatively, various conductive cooling elements may be used, such as a heat sink, e.g. a cooled metal block, in direct contact with the plates.

Figure 5:
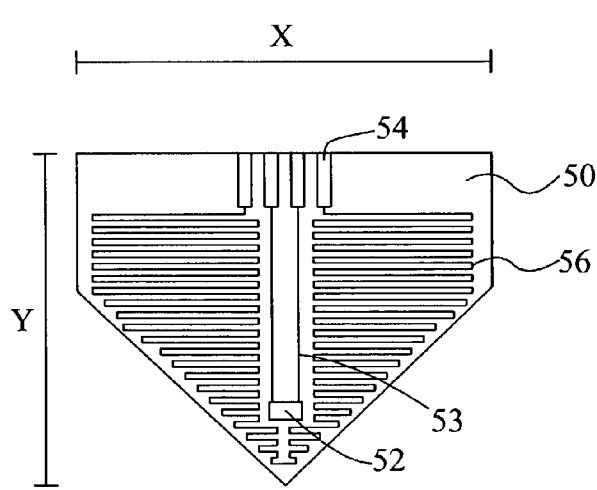
FIG. 5 is a front view of one of the plates of FIG. 4.

Referring to FIG. 5, in the preferred embodiment a resistive heating element 56 is coupled to each plate 50. The resistive heating element 56 is preferably a thick or thin film and may be directly screen printed onto each plate 50, particularly plates comprising a ceramic material, such as aluminum nitride or aluminum oxide. Screen-printing provides high reliability and low cross-section for efficient transfer of heat into the reaction chamber. Thick or thin film resistors of varying geometric patterns may be deposited on the outer surfaces of the plates to provide more uniform heating, for example by having denser resistors at the extremities and thinner resistors in the middle. Although it is presently preferred to deposit a heating element on the outer surface of each plate, a heating element may alternatively be baked inside of each plate, particularly if the plates are ceramic. The heating element 56 may comprise metals, tungsten, polysilicon, or other materials that heat when a voltage difference is applied across the material.

The heating element 56 has two ends which are connected to respective contacts 54 which are in turn connected to a voltage source (not shown in FIG. 5) to cause a current to flow through the heating element 56. Each plate 50 also preferably includes a temperature sensor 52, such as a thermocouple, thermistor, or RTD, which is connected by two traces 53 to respective contacts 54. The temperature sensor 52 may be used to monitor the temperature of the plate 50 in a controlled feedback loop.

The plates preferably have a low thermal mass to enable rapid heating and cooling of the plates. In particular, it is presently preferred that each of the plates has a thermal mass less than about 5 J/° C., more preferably less than 3 J/° C., and most preferably less than 1 J/° C. As used herein, the term thermal mass of a plate is defined as the specific heat of the plate multiplied by the mass of the plate. In addition, each plate should be large enough to cover a respective major wall of the reaction chamber. In the presently preferred embodiment, for example, each of the plates has a width X in the range of 2 to 22 mm, a length Y in the range of 2 to 22 mm, and a thickness in the range of 0.5 to 5 mm. The width X and length Y of each plate is selected to be slightly larger than the width and length of the reaction chamber. Moreover, each plate preferably has an angled bottom portion matching the geometry of the bottom portion of the reaction chamber, as is described below with reference to FIG. 12. Also in the preferred embodiment, each of the plates is made of aluminum nitride having a specific heat of about 0.75 J/g ° C. The mass of each plate is preferably in the range of 0.005 to 1.3 g so that each plate has a thermal mass in the range of 0.00375 to 1 J/° C.

Figure 6:
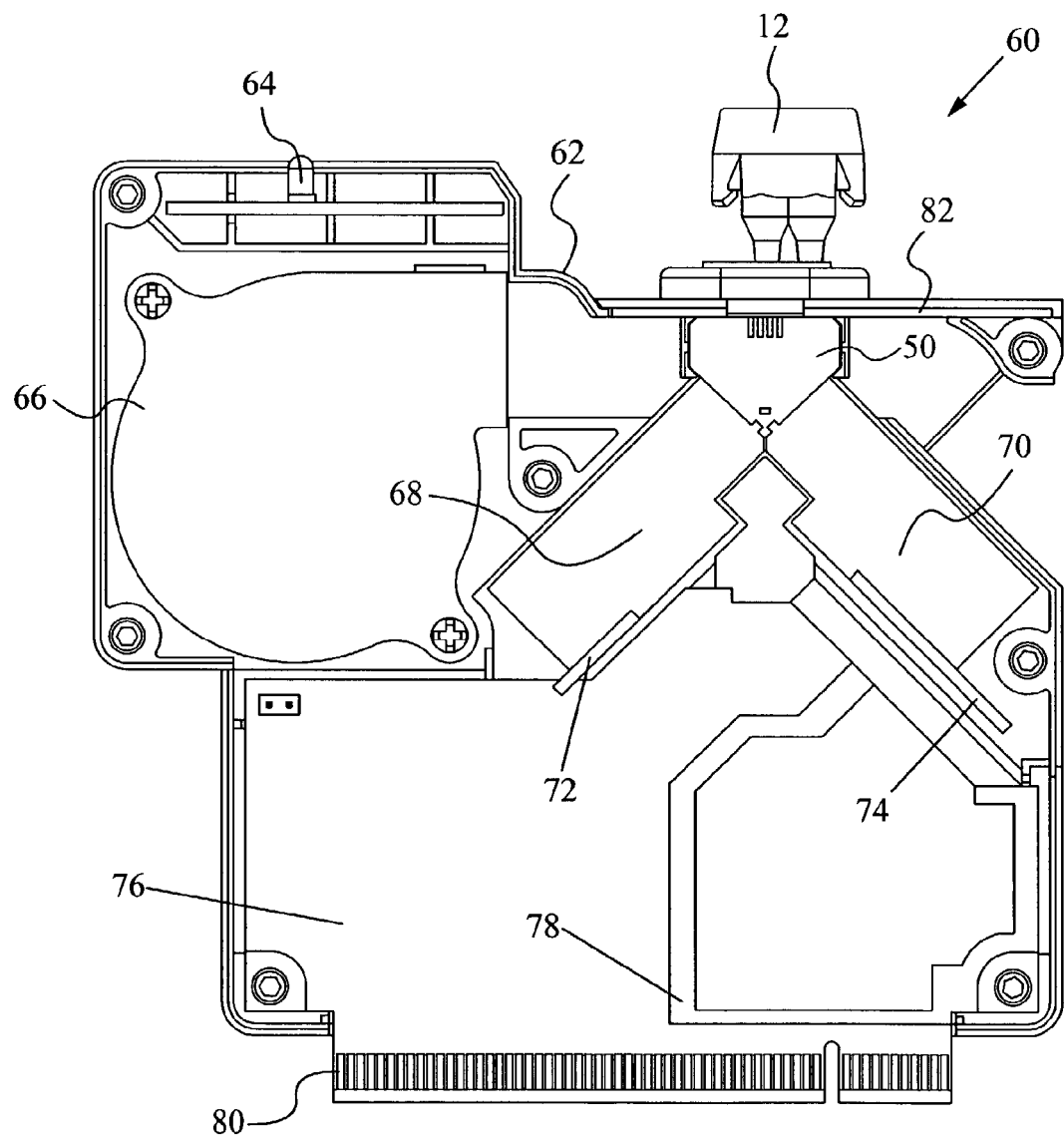
FIG. 6 is a schematic, front view of a heat-exchanging module according to the present invention having a thermal sleeve, a pair of optics assemblies, and a cooling system. The reaction vessel of FIG. 1 is inserted into the thermal sleeve.

FIG. 6 is a schematic side view of a heat-exchanging module 60 into which the reaction vessel 12 is inserted for thermal processing and optical interrogation. The module 60 preferably includes a housing 62 for holding the various components of the module. The module 60 also includes the thermally conductive plates 50 described above. The housing 62 includes a slot (not shown in FIG. 6) above the plates 50 so that the reaction chamber of the vessel 12 may be inserted through the slot and between the plates. The heat-exchanging module 60 also preferably includes a cooling system, such as a fan 66. The fan 66 is positioned to blow cooling air past the surfaces of the plates 50 to cool the plates and hence cool the sample in the vessel 12. The housing 62 preferably defines channels for directing the cooling air past the plates 50 and out of the module 60.

The heat-exchanging module 60 further includes an optical excitation assembly 68 and an optical detection assembly 70 for optically interrogating the sample contained in the vessel 12. The excitation assembly 68 includes a first circuit board 72 for holding its electronic components, and the detection assembly 68 includes a second circuit board 74 for holding its electronic components. The excitation assembly 68 includes one or more light sources, such as LEDs, for exciting fluorescently-labeled analytes in the vessel 12. The excitation assembly 68 also includes one or more lenses for collimating the light from the light sources, as well as filters for selecting the excitation wavelength ranges of interest. The detection assembly 70 includes one or more detectors, such as photodiodes, for detecting the light emitted from the vessel 12. The detection assembly 70 also includes one or more lenses for focusing and collimating the emitted light, as well as filters for selecting the emission wavelength ranges of interest. The specific components of the optics assemblies 68, 70 are described in greater detail below with reference to FIGS. 14–17.

The optics assemblies 68, 70 are positioned in the housing 62 such that when the chamber of the vessel 12 is inserted between the plates 50, the first optics assembly 68 is in optical communication with the chamber 17 through the optically transmissive side wall 19A (see FIG. 2) and the second optics assembly 70 is in optical communication with the chamber through the optically transmissive side wall 19B (FIG. 2). In the preferred embodiment, the optics assemblies 68, 70 are placed into optical communication with the optically transmissive side walls by simply locating the optics assemblies 68, 70 next to the bottom edges of the plates 50 so that when the chamber of the vessel is placed between the plates, the optics assemblies 68, 70 directly contact, or are in close proximity to, the side walls.

Figure 12:
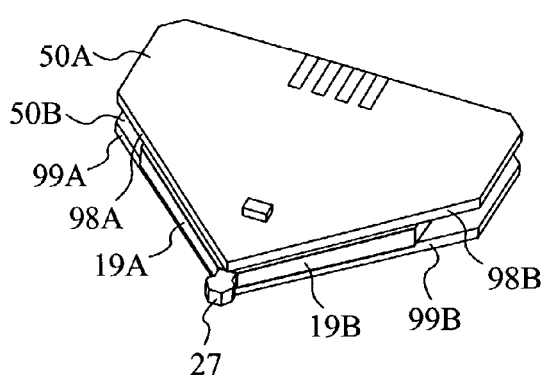
FIG. 12 is an isometric view of the vessel of FIG. 1 inserted between the plates of FIG. 4.

As shown in the partially cut-away view of FIG. 12 (in which the top portion of the vessel 12 has been cut away), the vessel 12 has an angled bottom portion (e.g., triangular) formed by the optically transmissive side walls 19A, 19B. Each of the plates 50A, 50B has a correspondingly shaped bottom portion. The bottom portion of the first plate 50A has a first bottom edge 98A and a second bottom edge 98B. Similarly, the bottom portion of the second plate 50B has a first bottom edge 99A and a second bottom edge 99B. The first and second bottom edges of each plate are preferably angularly offset from each other by the same angle that the side walls 19A, 19B are offset from each other (e.g., 90°). Additionally, the plates 50A, 50B are preferably positioned to receive the chamber of the vessel 12 between them such that the first side wall 19A is positioned substantially adjacent and parallel to each of the first bottom edges 98A, 99A and such that the second side wall 19B is positioned substantially adjacent and parallel to each of the second bottom edges 98B, 99B. This arrangement provides for easy optical access to the optically transmissive side walls 19A, 19B and hence to the chamber of the vessel 12.

The side walls 19A, 19B may be positioned flush with the edges of the plates 50A, 50B, or more preferably, the side walls 19A, 19B may be positioned such that they protrude slightly past the edges of the plates. As is explained below with reference to FIGS. 14–17, each optics assembly preferably includes a lens that physically contacts a respective one of the side walls 19A, 19B. It is preferred that the side walls 19A, 19B protrude slightly (e.g., 0.02 to 0.3 mm) past the edges of the plates 50A, 50B so that the plates do not physically contact and damage the lenses. A gel or fluid may optionally be used to establish or improve optical communication between each optics assembly and the side walls 19A, 19B. The gel or fluid should have a refractive index close to the refractive indexes of the elements that it is coupling.

Referring again to FIG. 6, the optics assemblies 68, 70 are preferably arranged to provide a 90° angle between excitation and detection paths. The 90° angle between excitation and detection paths assures that a minimum amount of excitation radiation entering through the first side wall of the chamber exits through the second side wall. Also, the 90° angle permits a maximum amount of emitted radiation to be collected through the second side wall. In the preferred embodiment, the vessel 12 includes a locating tab 27 (see FIG. 2) that fits into a slot formed between the optics assemblies 68, 70 to ensure proper positioning of the vessel 12 for optical detection. For improved detection, the module 60 also preferably includes a light-tight lid (not shown) that is placed over the top of the vessel 12 and made light-tight to the housing 62 after the vessel is inserted between the plates 50.

Although it is presently preferred to locate the optics assemblies 68, 70 next to the bottom edges of the plates 50, many other arrangements are possible. For example, optical communication may be established between the optics assemblies 68, 70 and the walls of the vessel 12 via optical fibers, light pipes, wave guides, or similar devices. One advantage of these devices is that they eliminate the need to locate the optics assemblies 68, 70 physically adjacent to the plates 50. This leaves more room around the plates in which to circulate cooling air or refrigerant, so that cooling may be improved.

The heat-exchanging module 60 also includes a PC board 76 for holding the electronic components of the module and an edge connector 80 for connecting the module 60 to a base instrument, as will be described below with reference to FIG. 18. The heating elements and temperature sensors on the plates 50, as well as the optical boards 72, 74, are connected to the PC board 76 by flex cables (not shown in FIG. 6 for clarity of illustration). The module 60 may also include a grounding trace 78 for shielding the optical detection circuit. The module 60 also preferably includes an indicator, such as an LED 64, for indicating to a user the current status of the module such as "ready to load sample", "ready to load reagent." "heating," "cooling," "finished," or "fault".

The housing 62 may be molded from a rigid, high-performance plastic, or other conventional material. The primary functions of the housing 62 are to provide a frame for holding the plates 50, optics assemblies 68, 70, fan 66, and PC board 76. The housing 62 also preferably provides flow channels and ports for directing cooling air from the fan 66 across the surfaces of the plates 50 and out of the housing. In the preferred embodiment, the housing 62 comprises complementary pieces (only one piece shown in the schematic side view of FIG. 6) that fit together to enclose the components of the module 60 between them.

The opposing plates 50 are positioned to receive the chamber of the vessel 12 between them such that the flexible major walls of the chamber contact and conform to the inner surfaces of the plates. It is presently preferred that the plates 50 be held in an opposing relationship to each other using, e.g., brackets, supports, or retainers. Alternatively, the plates 50 may be spring-biased towards each other as described in International Publication Number WO 98/38487, the disclosure of which is incorporated by reference herein. In another embodiment of the invention, one of the plates is held in a fixed position, and the second plate is spring-biased towards the first plate. If one or more springs are used to bias the plates towards each other, the springs should be sufficiently stiff to ensure that the plates are pressed against the flexible walls of the vessel with sufficient force to cause the walls to conform to the inner surfaces of the plates.

Figure 7:
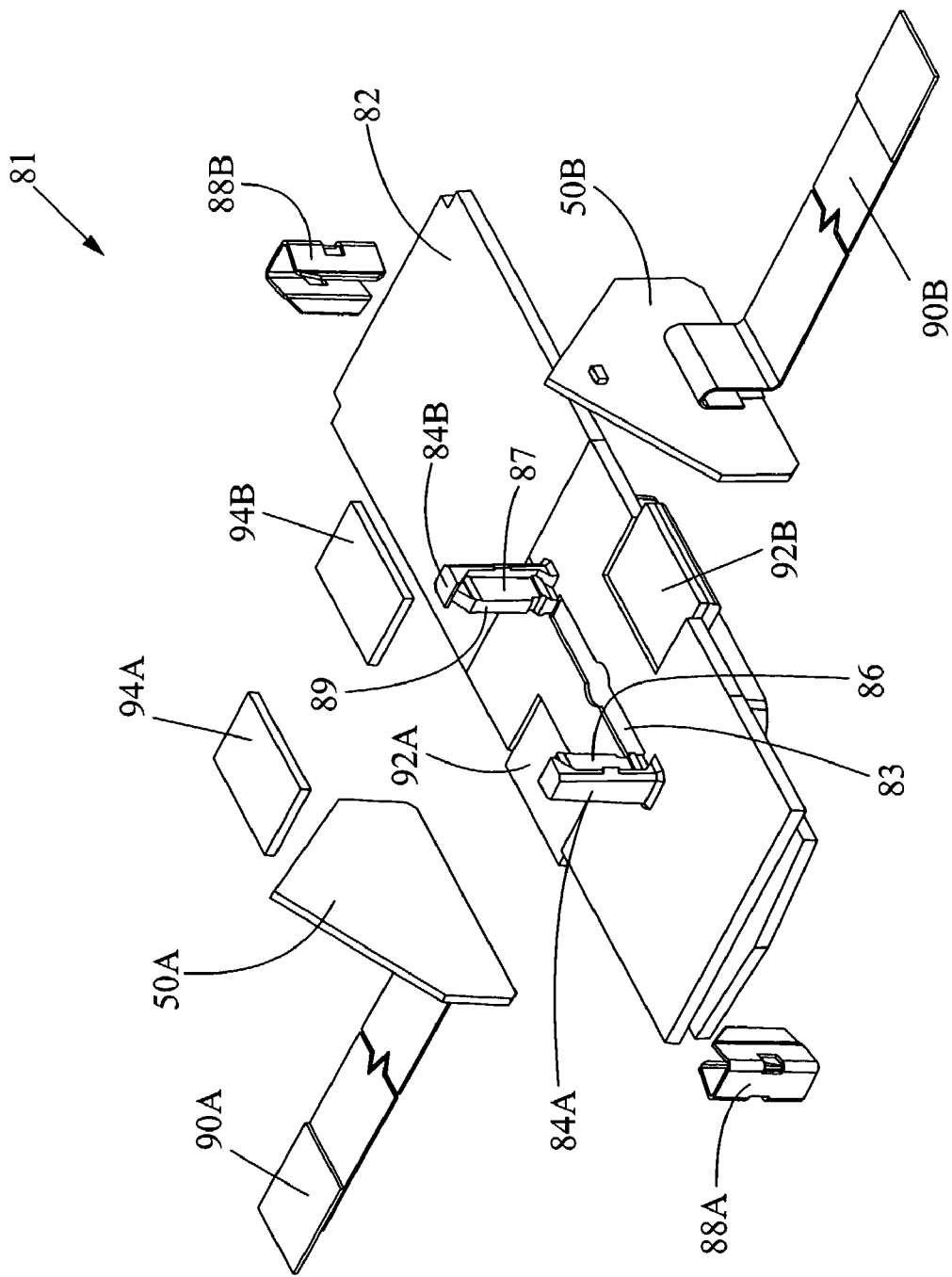
FIG. 7 is an exploded view of a support structure for holding the plates of FIG. 4.
Figure 8:
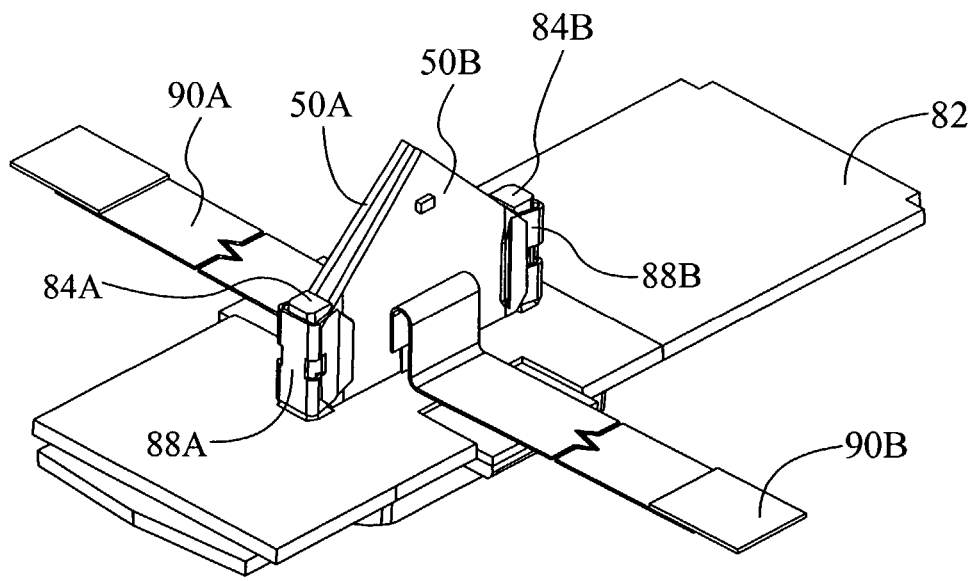
FIGS. 8–9 are assembled views of the support structure of FIG. 7.

FIGS. 7–8 illustrate a preferred support structure 81 for holding the plates 50A, 50B in an opposing relationship to each other. FIG. 7 shows an exploded view of the structure, and FIG. 8 shows an assembled view of the structure. For clarity of illustration, the support structure 81 and plates 50A, 50B are shown upside down relative to their normal orientation in the heat-exchanging module of FIG. 6. Referring to FIG. 7, the support structure 81 includes a mounting plate 82 having a slot 83 formed therein. The slot 83 is sufficiently large to enable the chamber of the vessel to be inserted through it. Spacing posts 84A, 84B extend from the mounting plate 82 on opposite sides of the slot 83. Spacing post 84A has indentations 86 formed on opposite sides thereof (only one side visible in the isometric view of FIG. 7), and spacing post 84B has indentations 87 formed on opposite sides thereof (only one side visible in the isometric view of FIG. 7). The indentations 86, 87 in the spacing posts are for receiving the edges of the plates 50A, 50B. To assemble the structure, the plates 50A, 50B are placed against opposite sides of the spacing posts 84A, 84B such that the edges of the plates are positioned in the indentations 86, 87. The edges of the plates are then held in the indentations using a suitable retention means. In the preferred embodiment, the plates are retained by retention clips 88A, 88B. Alternatively, the plates 50A, 50B may be retained by adhesive bonds, screws, bolts, clamps, or any other suitable means.

The mounting plate 82 and spacing posts 84A, 84B are preferably integrally formed as a single molded piece of plastic. The plastic should be a high temperature plastic, such as polyetherimide, which will not deform of melt when the plates 50A, 50B are heated. The retention clips 84A, 84B are preferably stainless steel. The mounting plate 82 may optionally include indentations 92A, 92B for receiving flex cables 90A, 90B, respectively, that connect the heating elements and temperature sensors disposed on the plates 50A, 50B to the PC board 76 of the heat-exchanging module 60 (FIG. 6). The portion of the flex cables 90A adjacent the plate 50A is held in the indentation 92A by a piece of tape 94A, and the portion of the flex cables 90B adjacent the plate 50B is held in the indentation 92B by a piece of tape 94B.

Figure 9:
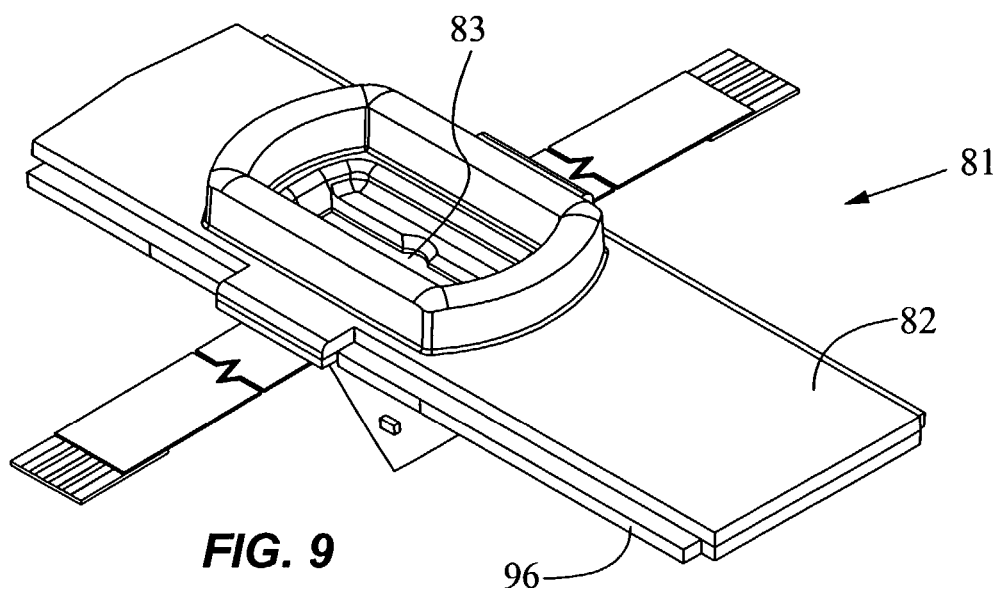

FIG. 9 is an isometric view of the assembled support structure 81. The mounting plate 82 preferably includes tabs 96 extending from opposite sides thereof for securing the structure 81 to the housing of the heat-exchanging module. Referring again to FIG. 6, the housing 62 preferably includes slots for receiving the tabs to hold the mounting plate 82 securely in place. Alternatively, the mounting plate 82 may be attached to the housing 62 using, e.g., adhesive bonding, screws, bolts, clamps, or any other conventional means of attachment.

Referring again to FIG. 7, the support structure 81 preferably holds the plates 50A, 50B so that their inner surfaces are angled very slightly towards each other. In the preferred embodiment, each of the spacing posts 84A, 84B has a wall 89 that is slightly tapered so that when the plates 50A, 50B are pressed against opposite sides of the wall, the inner surfaces of the plates are angled slightly towards each other. As best shown in FIG. 4, the inner surfaces of the plates 50A, 50B angle towards each other to form a slightly V-shaped slot into which the chamber 17 is inserted. The amount by which the inner surfaces are angled towards each other is very slight, preferably about 1° from parallel. The surfaces are angled towards each other so that, prior to the insertion of the chamber 17 between the plates 50A, 50B, the bottoms of the plates are slightly closer to each other than the tops. This slight angling of the inner surfaces enables the chamber 17 of the vessel to be inserted between the plates and withdrawn from the plates more easily. Alternatively, the inner surfaces of the plates 50A, 50B could be held parallel to each other, but insertion and removal of the vessel 12 may be more difficult.

In addition, the inner surfaces of the plates 50A, 50B are preferably spaced from each other a distance equal to the thickness of the frame 16. In embodiments in which the inner surfaces are angled towards each other, the centers of the inner surfaces are preferably spaced a distance equal to the thickness of the frame 16 and the bottoms of the plates are initially spaced a distance that is slightly less than the thickness of the frame 16. When the chamber 17 is inserted between the plates 50A, 50B, the rigid frame 16 forces the bottom portions of the plates apart so that the chamber 17 is firmly sandwiched between the plates. The distance that the plates 50A, 50B are wedged apart by the frame 16 is usually very small, e.g., about 0.035 mm if the thickness of the frame is 1 mm and the inner surfaces are angled towards each other by 1°.

Referring again to FIG. 8, the retention clips 88A, 88B should be sufficiently flexible to accommodate this slight outward movement of the plates 50A, 50B, yet sufficiently stiff to hold the plates within the recesses in the spacing posts 84A, 84B during insertion and removal of the vessel. The wedging of the vessel between the plates 50A, 50B provides an initial preload against the chamber and ensures that the flexible major walls of the chamber, when pressurized, establish good thermal contact with the inner surfaces of the plates.

Figure 10:
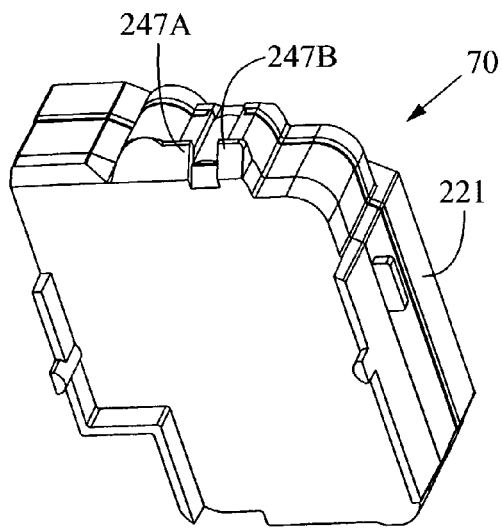
FIG. 10 is an isometric view showing the exterior of one the optics assemblies of FIG. 6.
Figure 11:
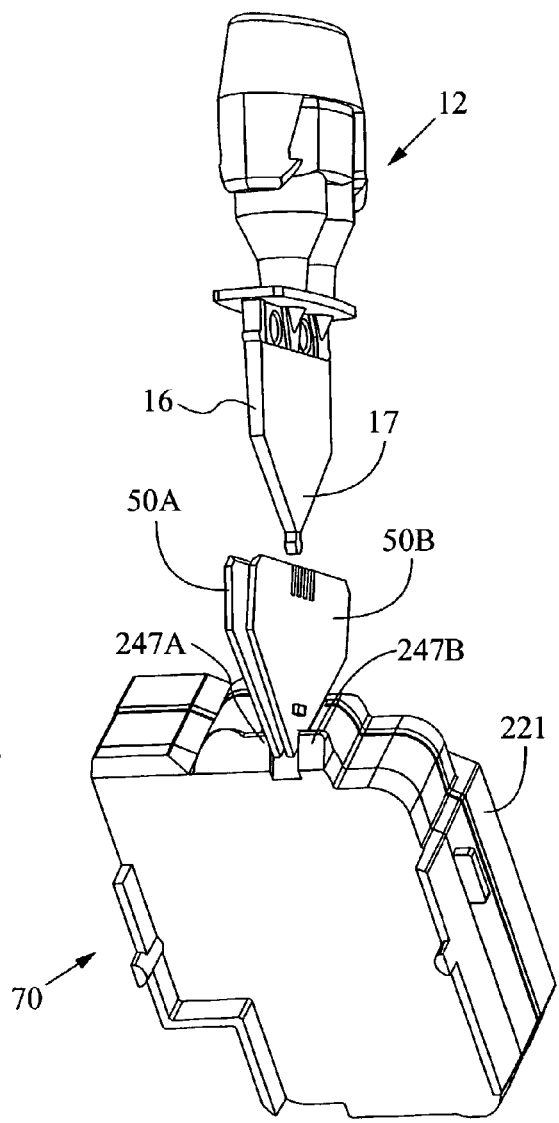
FIG. 11 is an isometric view of the plates of FIG. 4 in contact with the optics assembly of FIG. 10 with the vessel of FIG. 1 positioned above the plates.

Referring again to FIG. 6, to limit the amount that the plates 50 can spread apart due to the pressurization of the vessel 12, stops may be molded into the housings of optics assemblies 68, 70. As shown in FIG. 10, the housing 221 of the optics assembly 70 includes claw-like stops 247A, 247B that extend outwardly from the housing. As shown in FIG. 11, the housing 221 is positioned such that the bottom edges of the plates 50A, 50B are inserted between the stops 247A, 247B. The stops 247A, 247B thus prevent the plates 50A, 50B from spreading farther than a predetermined maximum distance from each other. Although not shown in FIG. 11 for illustrative clarity, the optics assembly 68 (see FIG. 6) has a housing with corresponding stops for preventing the other halves of the plates 50A, 50B from spreading farther than the predetermined maximum distance from each other. Referring again to FIG. 11, the maximum distance that stops 247A, 247B permit the inner surfaces of the plates 50A, 50B to be spaced from each other should closely match the thickness of the frame 16. Preferably, the maximum spacing of the inner surfaces of the plates 50A, 50B is slightly larger than the thickness of the frame 16 to accommodate tolerance variations in the vessel 12 and plates 50A, 50B. For example. the maximum spacing is preferably about 0.1 to 0.3 mm greater than the thickness of the frame 16.

Figure 13A:
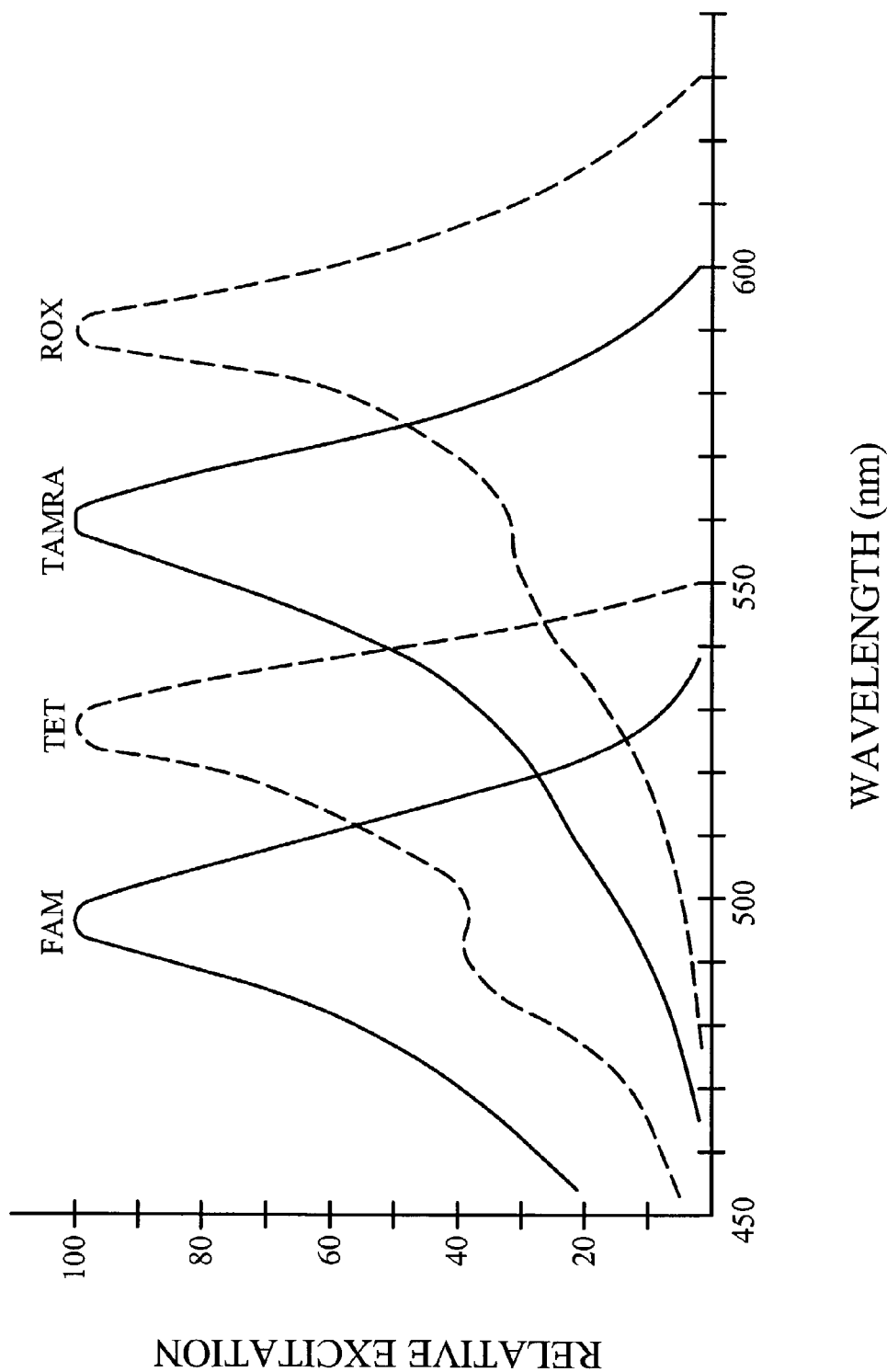
FIGS. 13A and 13B are graphs showing the excitation and emission spectra, respectively, of four dyes often used in thermal reactions.
Figure 13B:
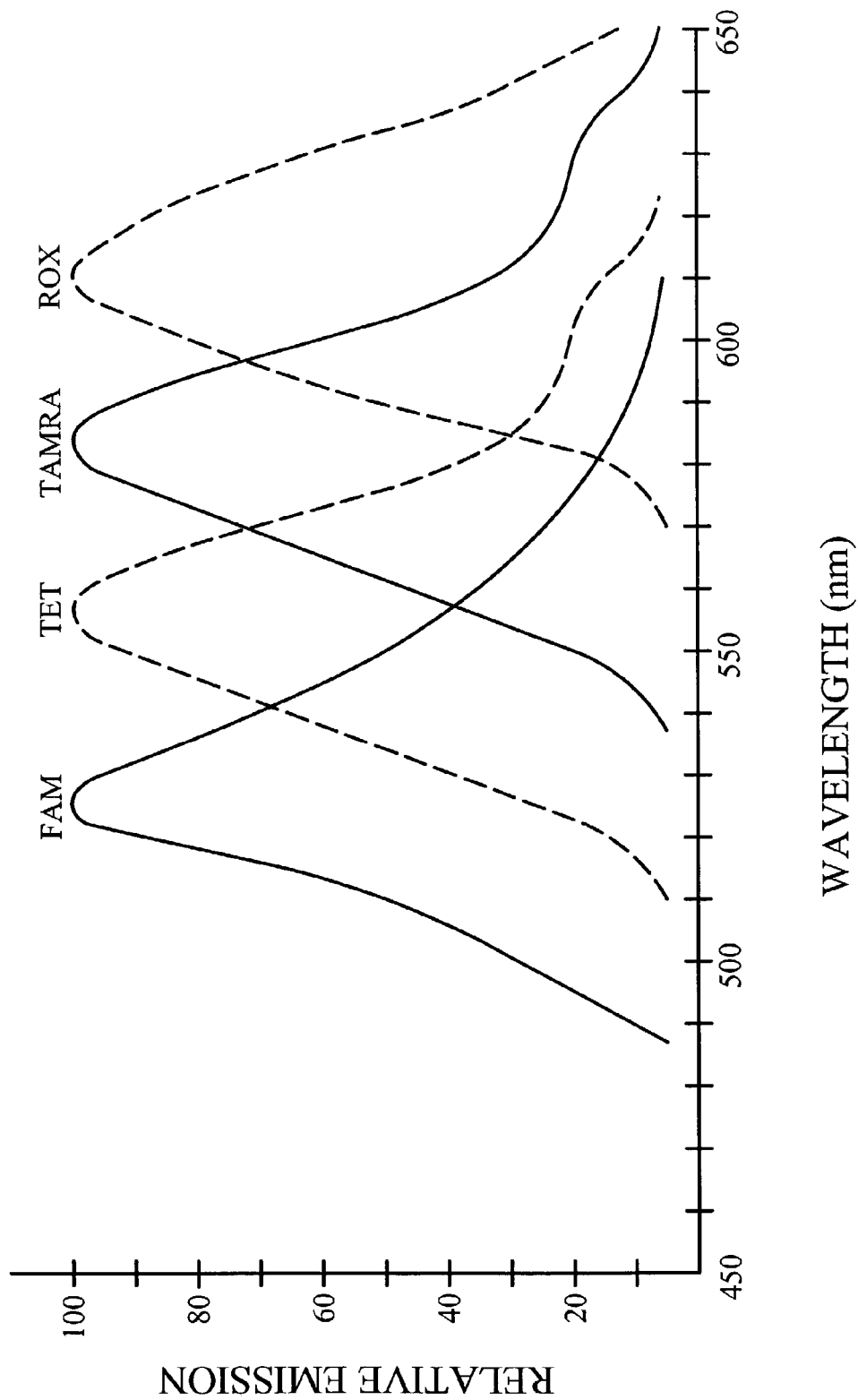

FIGS. 13A and 13B show the fluorescent excitation and emission spectra, respectively, of four fluorescent dyes of interest. These dyes are standard fluorescent dyes used with the TaqMan® chemistry (available from the Perkin-Elmer Corporation, Foster City, Calif.) and are well known by their acronyms FAM, TET, TAMRA, and ROX. Although the preferred embodiment is described with reference to these four dyes, it is to be understood that the system of the present invention is not limited to these particular dyes or to the TaqMan® chemistry. The system may be used with any fluorescent dyes or with interculating dyes such as SYBRGreen™ or ethidium bromide. Such dyes are commercially available from various well known suppliers. Fluorescent dyes, probes, and labeling chemistries for labeling analytes in a sample are well known in the art and need not be discussed further herein. Further, although fluorescence detection is presently preferred, the system of the present invention is not limited to detection based upon fluorescent labels. The system may be applicable to detection based upon phosphorescent labels, chemiluminescent labels, or electrochemiluminescent labels.

As shown in FIG. 13A, the excitation spectra curves for FAM, TET, TAMRA, and ROX are typically very broad at the base, but sharper at the peaks. As shown in FIG. 13B, the relative emission spectra curves for the same dyes are also very broad at the base and sharper at the peaks. Thus, these dyes have strongly overlapping characteristics in both their excitation and emission spectra. The overlapping characteristics have traditionally made it difficult to distinguish the fluorescent signal of one dye from another when multiple dyes are used to label different analytes in a sample.

Figure 13C:
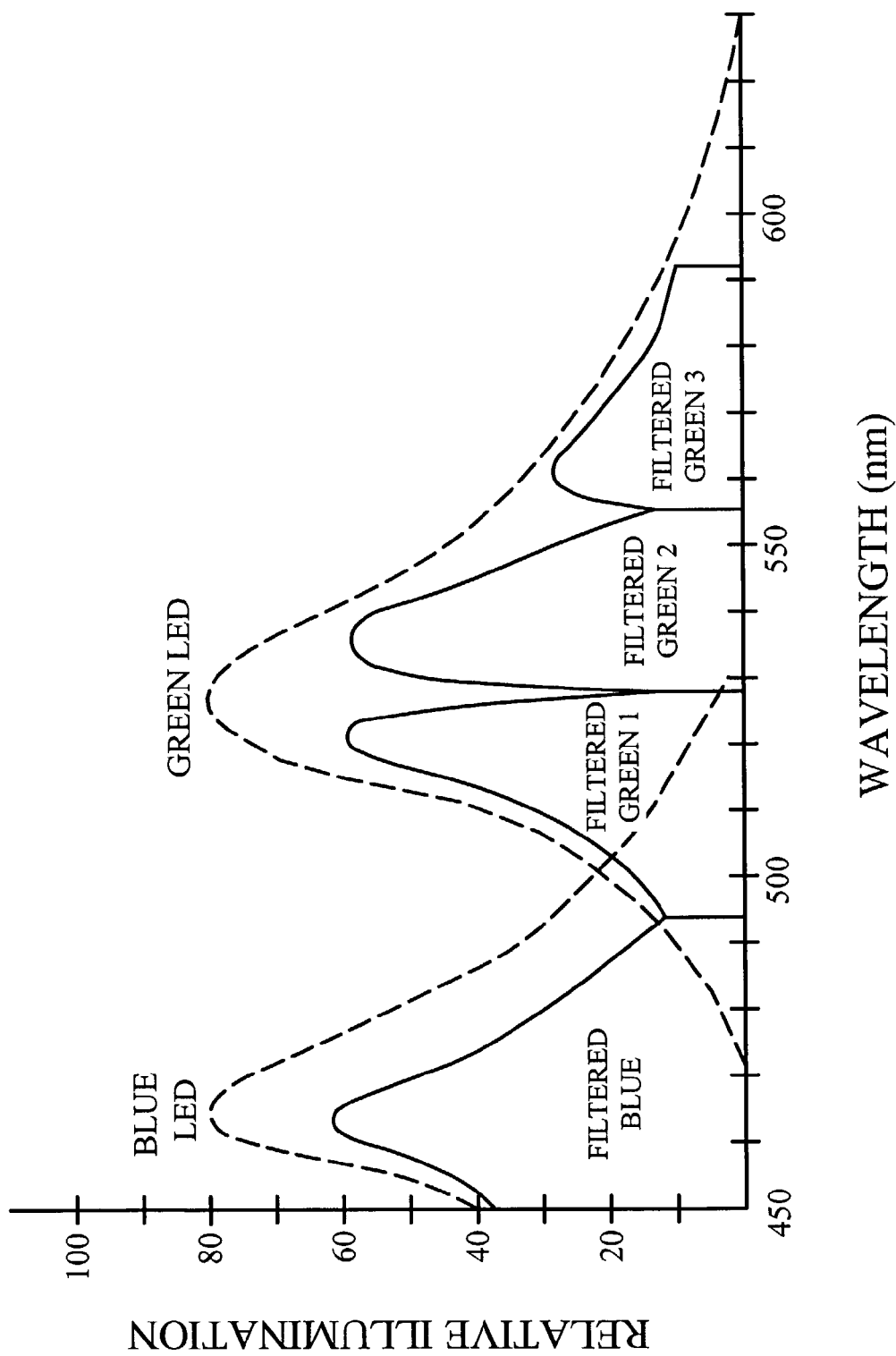
FIG. 13C shows the effects of filtering the outputs of green and blue LEDs to provide distinct excitation wavelength ranges.

Preferably, multiple light sources are used to provide excitation beams to the dyes in multiple excitation wavelength ranges. Each light source provides excitation light in a wavelength range matched to the peak excitation range of a respective one of the dyes. In the preferred embodiment, the light sources are blue and green LEDs. FIG. 13C shows the effects of filtering the outputs of blue and green LEDs to provide substantially distinct excitation wavelength ranges. Typical blue and green LEDs have substantial overlap in the range of around 480 nm through 530 nm. By the filtering regime of the present invention, the blue LED light is filtered to a range of about 450 to 495 nm to match the relative excitation peak for FAM. The green LED light is filtered to a first range of 495 to 527 nm corresponding to the excitation peak for TET, a second range of 527 to 555 nm corresponding to the excitation peak for TAMRA, and a third range of 555 to 593 nm corresponding to the excitation peak for ROX.

Figure 13D:
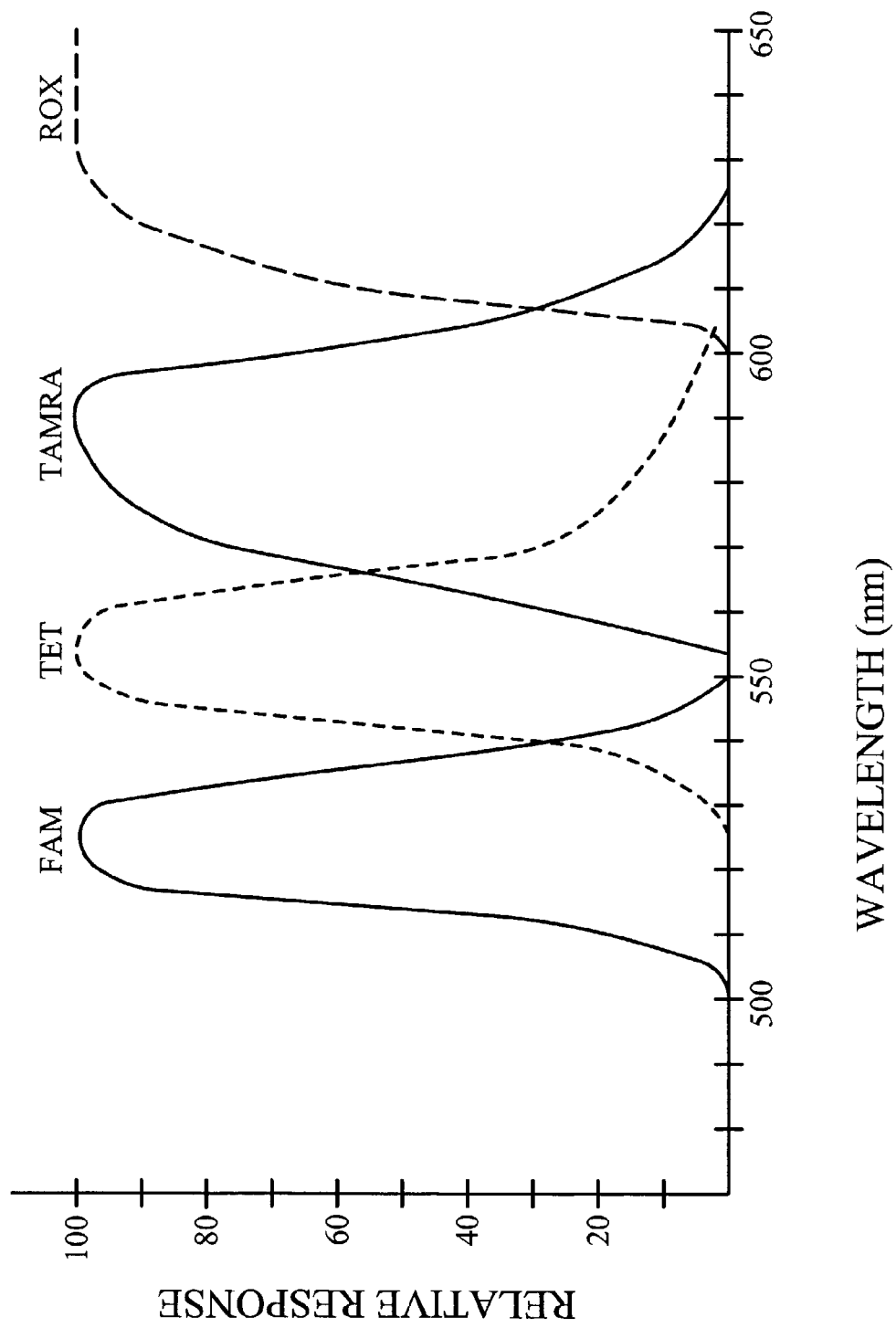
FIG. 13D shows the effects of filtering light emitted from each of the four dyes of FIGS. 13A–B to form distinct emission wavelength ranges.

FIG. 13D shows the effects of filtering light emitted (fluorescent emission) from each of the four dyes to form distinct emission wavelength ranges. As shown previously in FIG. 13B, the fluorescent emissions of the dyes before filtering are spherically diffuse with overlapping spectral bandwidths, making it difficult to distinguish the fluorescent output of one dye from another. As shown in FIG. 13D, by filtering the fluorescent emissions of the dyes into substantially distinct wavelength ranges, a series of relatively narrow peaks (detection windows) are obtained, making it possible to distinguish the fluorescent outputs of different dyes, thus enabling the detection of a number of different fluorescently-labeled analytes in a sample.

Figure 14:
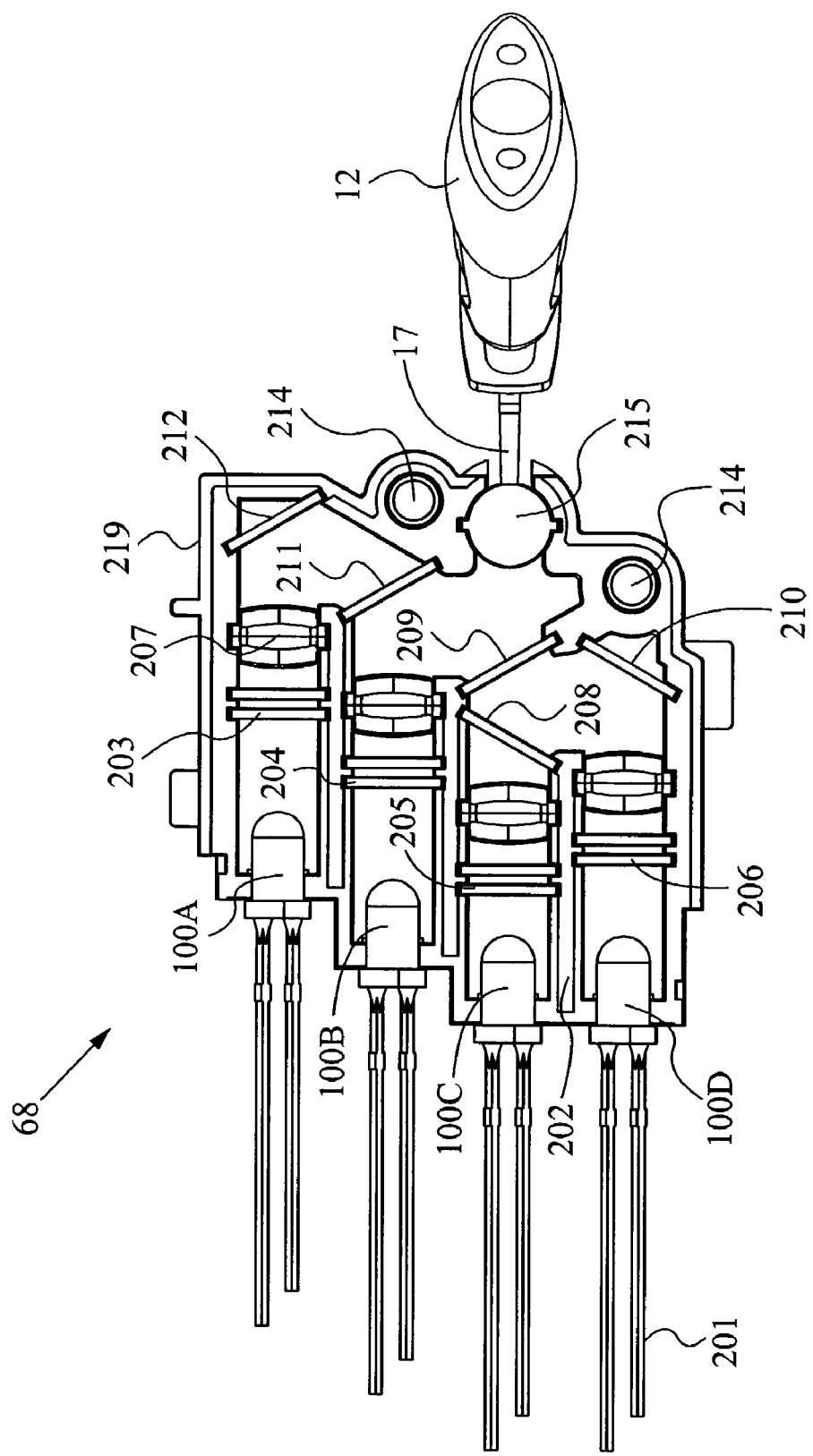
FIG. 14 is a plan view of an optical excitation assembly of the module of FIG. 6.
Figure 15:
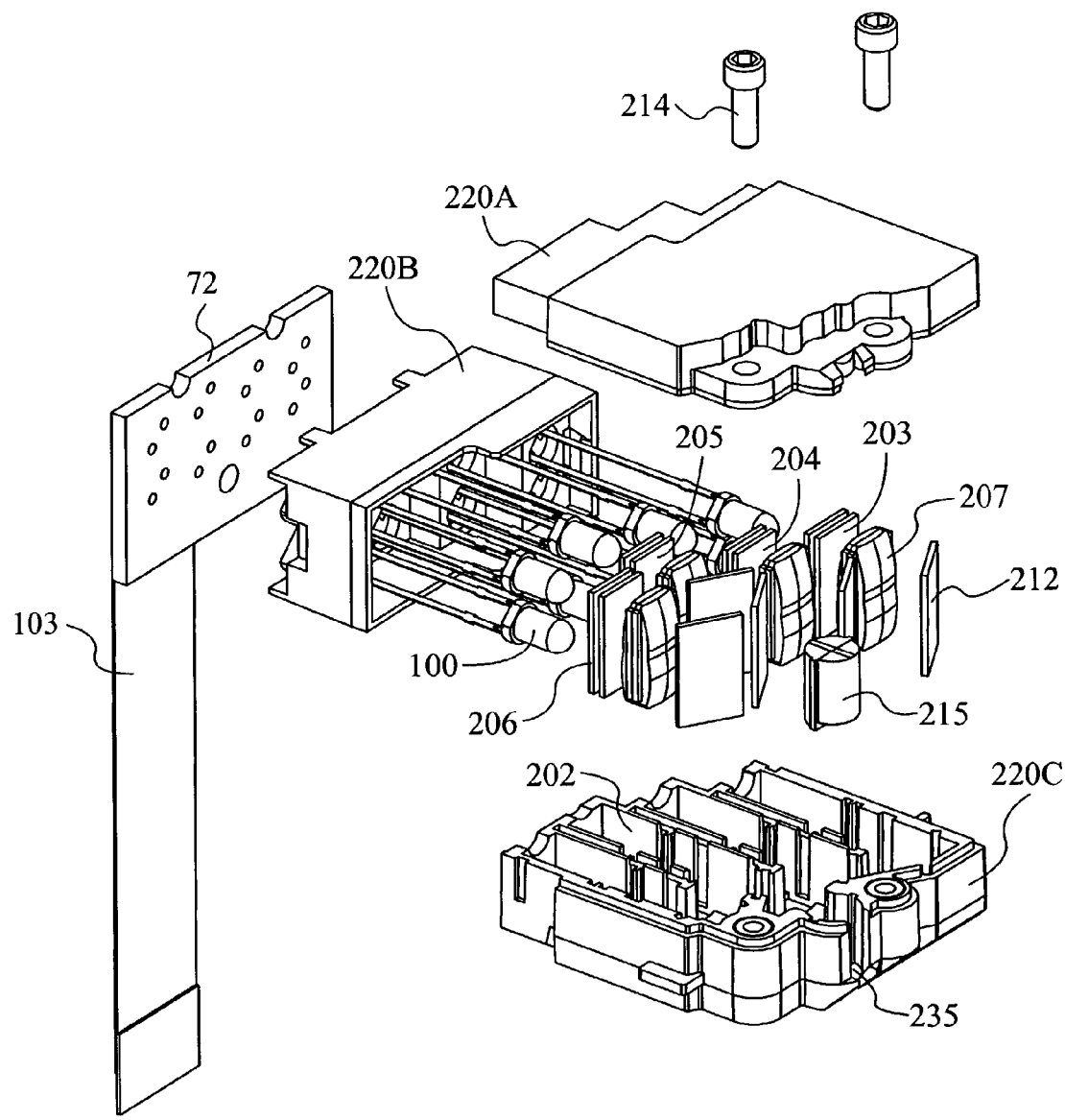
FIG. 15 is an exploded view of the excitation assembly of FIG. 14.

FIG. 14 is a schematic, plan view of the optical excitation assembly 68. The assembly 68 is positioned adjacent the reaction vessel 12 to transmit excitation beams to the sample contained in the chamber 17. FIG. 15 is an exploded view of the excitation assembly. As shown in FIGS. 14–15, the excitation assembly 68 includes a housing 219 for holding various components of the assembly. The housing 219 preferably comprises one or more molded pieces of plastic. In the preferred embodiment, the housing 219 is a multi-part housing comprised of three housing elements 220A, 220B, and 220C. The upper and lower housing elements 220A and 220C are preferably complementary pieces that couple together and snap-fit into housing element 220B. In this embodiment, the housing elements 220A and 220C are held together by screws 214. In alternative embodiments, the entire housing 219 may be a one-piece housing that holds a slide-in optics package.

The lower housing element 220C includes an optical window 235 into which is placed a cylindrical rod lens 215 for focusing excitation beams into the chamber 17. In general, the optical window 235 may simply comprise an opening in the housing through which excitation beams may be transmitted to the chamber 17. The optical window may optionally include an optically transmissive or transparent piece of glass or plastic serving as a window pane, or as in the preferred embodiment, a lens for focusing excitation beams. The lens 215 preferably directly contacts one of the optically transmissive side walls of the chamber 17.

The optics assembly 68 also includes four light sources, preferably LEDs 100A, 100B, 100C, and 100D, for transmitting excitation beams through the lens 215 to the sample contained in the chamber 17. In general, each light source may comprise a laser, a light bulb, or an LED. In the preferred embodiment, each light source comprises a pair of directional LEDs. In particular, the four light sources shown in FIGS. 14–15 are preferably a first pair of green LEDs 100A, a second pair of green LEDs 100B, a pair of blue LEDs 100C, and a third pair of green LEDs 100D. The LEDs receive power through leads 201 which are connected to a power source (not shown in FIGS. 14–15). The LEDs are mounted to the optical circuit board 72 which is attached to the back of the housing element 220B so that the LEDs are rigidly fixed in the housing. The optical circuit board 72 is connected to the main PC board of the heat-exchanging module (shown in FIG. 6) via the flex cable 103.

The optics assembly 68 further includes a set of filters and lenses arranged in the housing 219 for filtering the excitation beams generated by the LEDs so that each of the beams transmitted to the chamber 17 has a distinct excitation wavelength range. As shown in FIG. 15, the lower housing element 220C preferably includes walls 202 that create separate excitation channels in the housing to reduce potential cross-talk between the different pairs of LEDs. The walls 202 preferably include slots for receiving and rigidly holding the filters and lenses. The filters and lenses may also be fixed in the housing by means of an adhesive used alone, or more preferably, with an adhesive used in combination with slots in the housing.

Referring to FIG. 14, the filters in the optics assembly 68 may be selected to provide excitation beams to the sample in the chamber 17 in any desired excitation wavelength ranges. The optics assembly 68 may therefore be used with any fluorescent, phosphorescent, chemiluminescent, or electrochemiluminescent labels of interest. For purposes of illustration, one specific embodiment of the assembly 68 will now be described in which the assembly is designed to provide excitation beams corresponding to the peak excitation wavelength ranges FAM, TAMRA, TET, and ROX.

In this embodiment, a pair of 593 nm low pass filters 203 are positioned in front of green LEDs 100A, a pair of 555 nm low pass filters 204 are positioned in front of green LEDs 100B, a pair of 495 nm low pass filters 205 are positioned in front of blue LEDs 100C, and a pair of 527 nm low pass filters 206 are positioned in front of green LEDs 100D. Although it is presently preferred to position a pair of low pass filters in front of each pair of LEDs for double filtering of excitation beams, a single filter may be used in alternative embodiments. In addition, a lens 207 is preferably positioned in front of each pair of filters for collimating the filtered excitation beams. The optics assembly 68 also includes a 495 nm high pass reflector 208, a 527 nm high pass reflector 209, a mirror 210, a 555 nm low pass reflector 211, and a 593 nm low pass reflector 212. The reflecting filters and mirrors 208–212 are angularly offset by 30° from the low pass filters 203–206.

The excitation assembly 68 transmits excitation beams to the chamber 17 in four distinct excitation wavelength ranges as follows. When the green LEDs 100A are activated, they generate an excitation beam that passes through the pair of 593 nm low pass filters 203 and through the lens 207. The excitation beam then reflects off of the 593 nm low pass reflector 212, passes through the 555 nm low pass reflector 211, reflects off of the 527 nm high pass reflector 209, and passes through the lens 215 into the reaction chamber 17. The excitation beam from the LEDs 100A is thus filtered to a wavelength range of 555 to 593 nm corresponding to the peak excitation range for ROX. When the green LEDs 100B are activated, they generate an excitation beam that passes through the pair of 555 nm low pass filters 204, reflects off of the 555 nm low pass reflector 211, reflects off of the 527 nm high pass reflector 209, and passes through the lens 215 into the reaction chamber 17. The excitation beam from LEDs 100B is thus filtered to a wavelength range of 527 to 555 nm corresponding to the peak excitation range for TAMRA.

When the blue LEDs 100C are activated, they generate an excitation beam that passes through the pair of 495 nm low pass filters 205, through the 495 nm high pass reflector 208, through the 527 nm high pass reflector 209, and through the lens 215 into the reaction chamber 17. The excitation beam from LEDs 100C is thus filtered to a wavelength below 495 nm corresponding to the peak excitation range for FAM. When the green LEDs 100D are activated, they generate an excitation beam that passes through the pair of 527 nm low pass filters 206, reflects off of the mirror 210, reflects off of the 495 nm high pass reflector 208, passes through the 527 nm high pass reflector 209, and passes through the lens 215 into the reaction chamber 17. The excitation beam from LEDs 100D is thus filtered to a wavelength range of 495 to 527 nm corresponding to the peak excitation range for TET. In operation, the LEDs 100A, 100B, 100C, 100D are sequentially activated to excite the different fluorescent labels contained in the chamber 17 with excitation beams in substantially distinct wavelength ranges.

Figure 16:
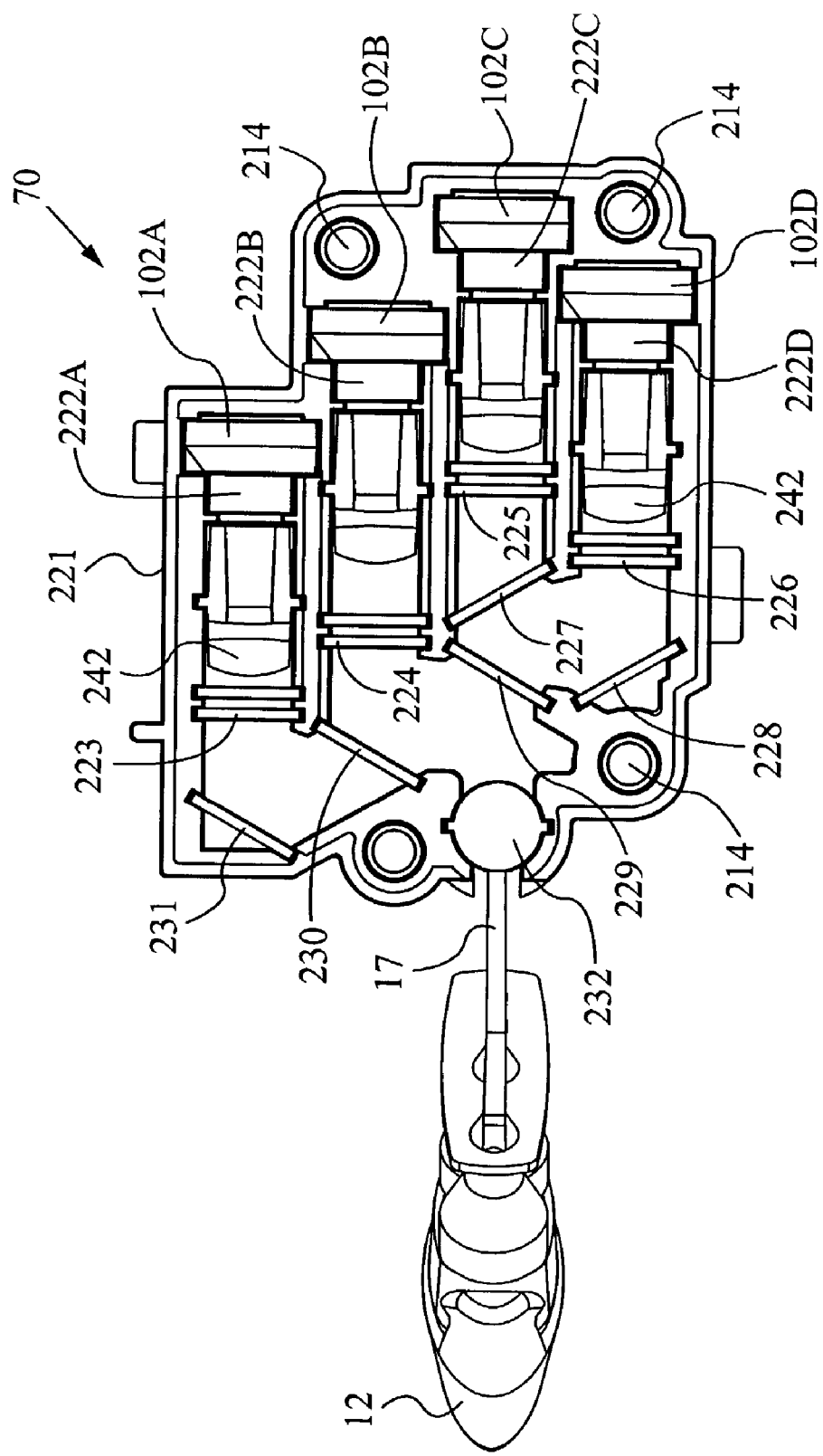
FIG. 16 is a plan view of an optical detection assembly of the module of FIG. 6.
Figure 17:
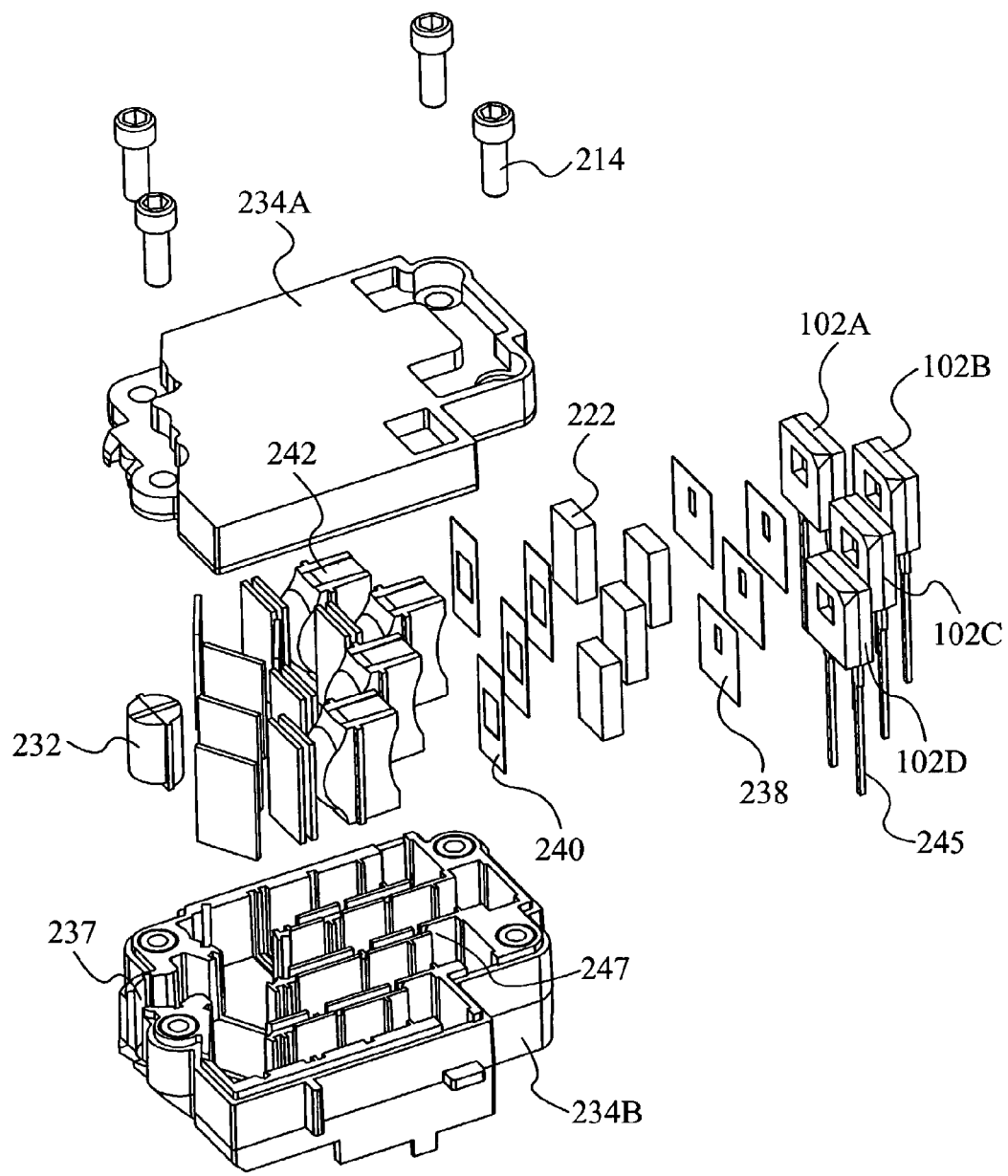
FIG. 17 is an exploded view of the detection assembly of FIG. 16.

FIG. 16 is a schematic, plan view of the optical detection assembly 70. The assembly 70 is positioned adjacent the reaction vessel 12 to receive light emitted from the chamber 17. FIG. 17 is an exploded view of the detection assembly 70. As shown in FIGS. 16–17, the assembly 70 includes a housing 221 for holding various components of the assembly. The housing 221 preferably comprises one or more molded plastic pieces. In the preferred embodiment, the housing 221 is a multi-part housing comprised of upper and lower housing elements 234A and 234B. The housing elements 234A, 234B are complementary, mating pieces that are held together by screws 214. In alternative embodiments, the entire housing 221 may be a one-piece housing that holds a slide-in optics package.

The lower housing element 234B includes an optical window 237 into which is placed a cylindrical rod lens 232 for collimating light emitted from the chamber 17. In general, the optical window may simply comprise an opening in the housing through which the emitted light may be received. The optical window may optionally include an optically transmissive or transparent piece of glass or plastic serving as a window pane, or as in the preferred embodiment, the lens 232 for collimating light emitted from the chamber 17. The lens 232 preferably directly contacts one of the optically transmissive side walls of the chamber 17.

The optics assembly 70 also includes four detectors 102A, 102B, 102C, and 102D for detecting light emitted from the chamber 17 that is received through the lens 232. In general, each detector may be a photomultiplier tube, CCD, photodiode, or other known detector. In the preferred embodiment, each detector is a PIN photodiode. The detectors 102A, 102B, 102C, and 102D are preferably rigidly fixed in recesses formed in the lower housing element 234B. The detectors are electrically connected by leads 245 to the optical circuit board 74 (see FIG. 6) which is preferably mounted to the underside of the lower housing element 234B.

The optics assembly 70 further includes a set of filters and lenses arranged in the housing 221 for separating light emitted from the chamber 17 into different emission wavelength ranges and for directing the light in each of the emission wavelength ranges to a respective one of the detectors. As shown in FIG. 17, the lower housing element 234B preferably includes walls 247 that create separate detection channels in the housing, with one of the detectors positioned at the end of each channel. The walls 247 preferably include slots for receiving and rigidly holding the filters and lenses. The filters and lenses may also be rigidly fixed in the housing 221 by an adhesive used alone, or more preferably, with an adhesive used in combination with slots in the housing.

Referring to FIG. 16, the filters in the optics assembly 70 may be selected to block light emitted from the chamber 17 outside of any desired emission wavelength ranges. The optics assembly 70 may therefore be used with any fluorescent, phosphorescent, chemiluminescent, or electrochemiluminescent labels of interest. For purposes of illustration, one specific embodiment of the assembly 70 will now be described in which the assembly is designed to detect light emitted from the chamber 17 in the peak emission wavelength ranges of FAM, TAMRA, TET, and ROX.

In this embodiment, the set of filters preferably includes a 515 nm Schott Glass® filter 222A positioned in front of the first detector 102A, a 550 nm Schott Glass® filter 222B positioned in front of the second detector 102B, a 570 nm Schott Glass® filter 222C positioned in front of the third detector 102C, and a 620 nm Schott Glass® filter 222D positioned in front of the fourth detector 102D. These Schott Glass® filters are commercially available from Schott Glass Technologies, Inc. of Duryea, Pa. The optics assembly 70 also includes a pair of 505 nm high pass filters 223 positioned in front of the first detector 102A, a pair of 537 nm high pass filters 224 positioned in front of the second detector 102B, a pair of 565 nm high pass filters 225 positioned in front of the third detector 102C, and a pair of 605 nm high pass filters 226 positioned in front of the fourth detector 102D.

Although it is presently preferred to position a pair of high pass filters in front of each detector for double filtering of light, a single filter may be used in alternative embodiments. In addition, a lens 242 is preferably positioned in each detection channel between the pair of high pass filters and the Schott Glass® filter for collimating the filtered light. The optics assembly 70 further includes a 605 nm high pass reflector 227, a mirror 228, a 565 nm low pass reflector 229, a 537 nm high pass reflector 230, and a 505 nm high pass reflector 231. The reflecting filters and mirrors 227–231 are preferably angularly offset by 30° from the high pass filters 223–226. As shown in FIG. 17, the detection assembly 70 also preferably includes a first aperture 238 positioned between each detector and Schott Glass® filter 222 and an aperture 240 positioned between each lens 242 and Schott Glass® filter 222. The apertures 238, 240 reduce the amount of stray or off-axis light that reaches the detectors 102A, 102B, 102C, and 102D.

Referring again to FIG. 16, the detection assembly 70 detects light emitted from the chamber 17 in four emission wavelength ranges as follows. The emitted light passes through the lens 232 and strikes the 565 nm low pass reflector 229. The portion of the light having a wavelength in the range of about 505 to 537 nm (corresponding to the peak emission wavelength range of FAM) reflects from the 565 nm low pass reflector 229, passes through the 537 nm high pass reflector 230, reflects from the 505 nm high pass reflector 231, passes through the pair of 505 nm high pass filters 223, through the lens 242, through the 515 nm Schott Glass® filter 222A, and is detected by the first detector 102A. Meanwhile, the portion of the light having a wavelength in the range of about 537 to 565 nm (corresponding to the peak emission wavelength range of TET) reflects from the 565 nm low pass reflector 229, reflects from the 537 nm high pass reflector 230, passes through the pair of 537 nm high pass filters 224, through the lens 242, through the 550 nm Schott Glass® filter 222B, and is detected by the second detector 102B.

Further, the portion of the light having a wavelength in the range of about 565 to 605 nm (corresponding to the peak emission wavelength range of TAMRA) passes through the 565 nm low pass reflector 229, through the 605 nm high pass reflector 227, through the pair of 565 nm high pass filters 225, through the lens 242, through the 570 nm Schott Glass® filter 222C, and is detected by the third detector 102C. The portion of the light having a wavelength over 605 nm (corresponding to the peak emission wavelength range of ROX) passes through the 565 nm low pass reflector 229, reflects from the 605 nm high pass reflector 227, reflects from the mirror 228, passes through the pair of 605 nm high pass filters 226, through the lens 242, through the 620 nm Schott Glass® filter 222D, and is detected by the fourth detector 102D. In operation, the outputs of detectors 102A, 102B, 102C, and 102D are analyzed to determine the concentrations of each of the different fluorescently-labeled analytes contained in the chamber 17, as will be described in greater detail below.

Figure 18:
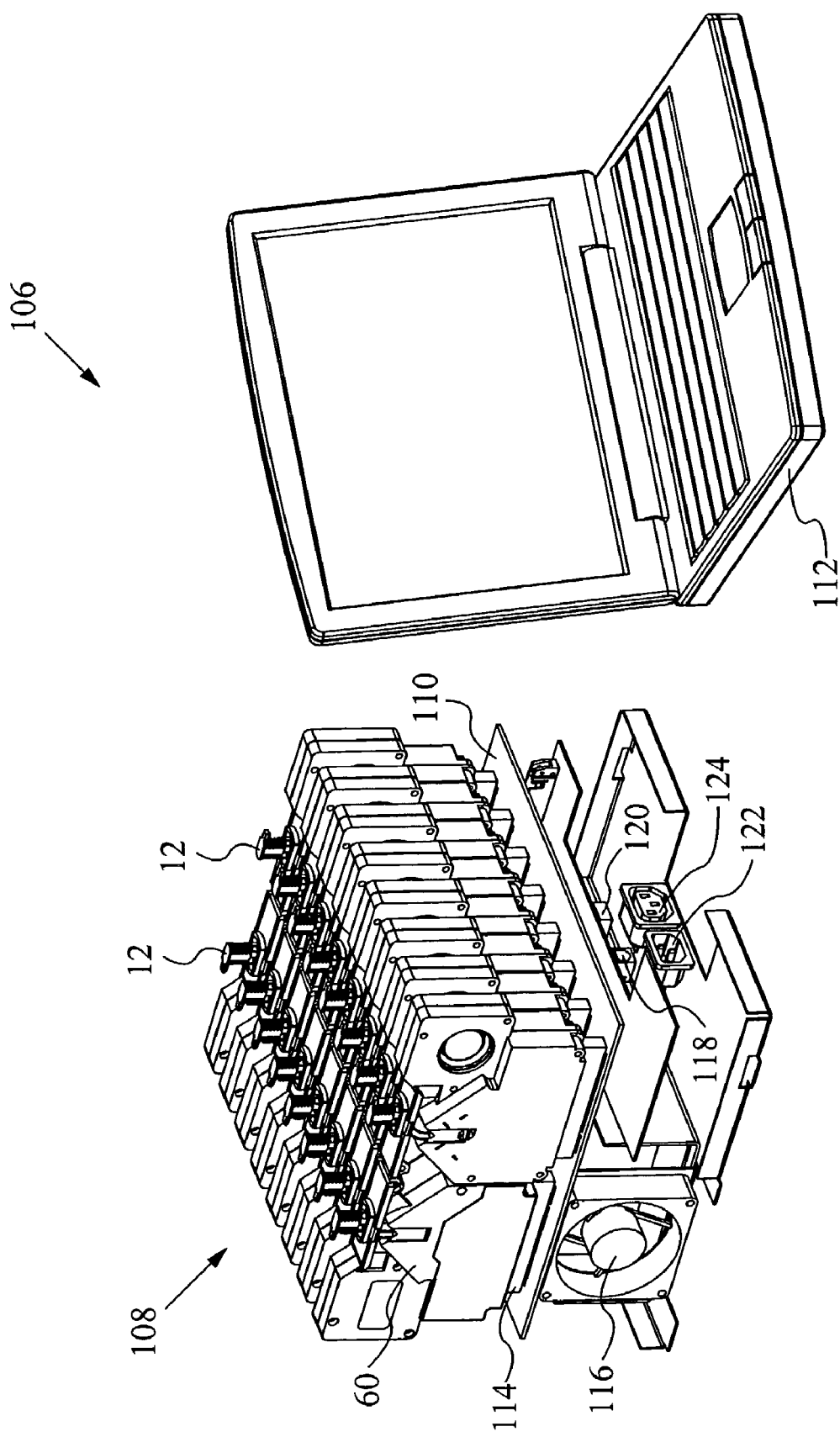
FIG. 18 is an isometric view of a multi-site reactor system according to an embodiment present invention.
Figure 19:
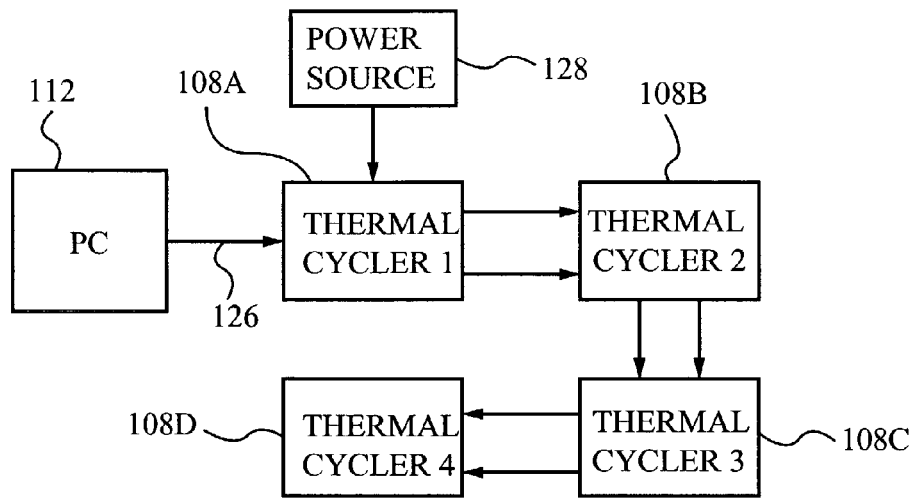
FIG. 19 is a schematic, block diagram of another multi-site reactor system having multiple thermal cycling instruments daisy-chained to a computer and a power source.

FIG. 18 shows a multi-site reactor system 106 according to the present invention. The reactor system 106 comprises a thermal cycler 108 and a controller 112, such as a personal or network computer. The thermal cycler 108 includes a base instrument 110 for receiving multiple heat-exchanging modules 60 (previously described with reference to FIG. 6). The base instrument 110 has a main logic board with edge connectors 114 for establishing electrical connections to the modules 60. The base instrument 110 also preferably includes a fan 116 for cooling its electronic components. The base instrument 110 may be connected to the controller 112 using any suitable data connection, such as a universal serial bus (USB), ethernet connection, or serial line. It is presently preferred to use a USB that connects to the serial port of controller 112. Alternatively, the controller may be built into the base instrument 110.

The term "thermal cycling" is herein intended to mean at least one change of temperature, i.e. increase or decrease of temperature, in a sample. Therefore, samples undergoing thermal cycling may shift from one temperature to another and then stabilize at that temperature, transition to a second temperature or return to the starting temperature. The temperature cycle may be performed only once or may be repeated as many times as required to study or complete the particular chemical reaction of interest. Due to space limitations in patent drawings, the thermal cycler 108 shown in FIG. 18 includes only sixteen reaction sites provided by the sixteen heat-exchanging modules 60 arranged in two rows of eight modules each. It is to be understood, however, that the thermal cycler can include any number of desired reaction sites, i.e., it can be configured as a multi-hundred site instrument for simultaneously processing hundreds of samples. Alternatively, it may be configured as a small, hand held, battery-operated instrument having, e.g., 1 to 4 reaction sites.

Each of the reaction sites in the thermal cycler 108 is provided by a respective one of the heat-exchanging modules 60. The modules 60 are preferably independently controllable so that different chemical reactions can be run simultaneously in the thermal cycler 108. The thermal cycler 108 is preferably modular so that each heat-exchanging module 60 can be individually removed from the base instrument 110 for servicing, repair, or replacement. This modularity reduces downtime since all the modules 60 are not off line to repair one, and the instrument 110 can be upgraded and enlarged to add more modules as needed. The modularity of the thermal cycler 108 also means that individual modules 60 can be precisely calibrated, and module-specific schedules or corrections can be included in the control programs, e.g., as a series of module-specific calibration or adjustment charts.

In embodiments in which the base instrument 110 operates on external power, e.g. 110 V AC, the instrument preferably includes two power connections 122, 124. Power is received though the first connection 122 and output through the second connection 124. Similarly, the instrument 110 preferably includes network interface inlet and outlet ports 118, 120 for receiving a data connection through inlet port 118 and outputting data to another base instrument through outlet port 120. As shown in the block diagram of FIG. 19, this arrangement permits multiple thermal cyclers 108A, 108B, 108C, 108D to be daisy-chained from one controller 112 and one external power source 128.

Figure 20:
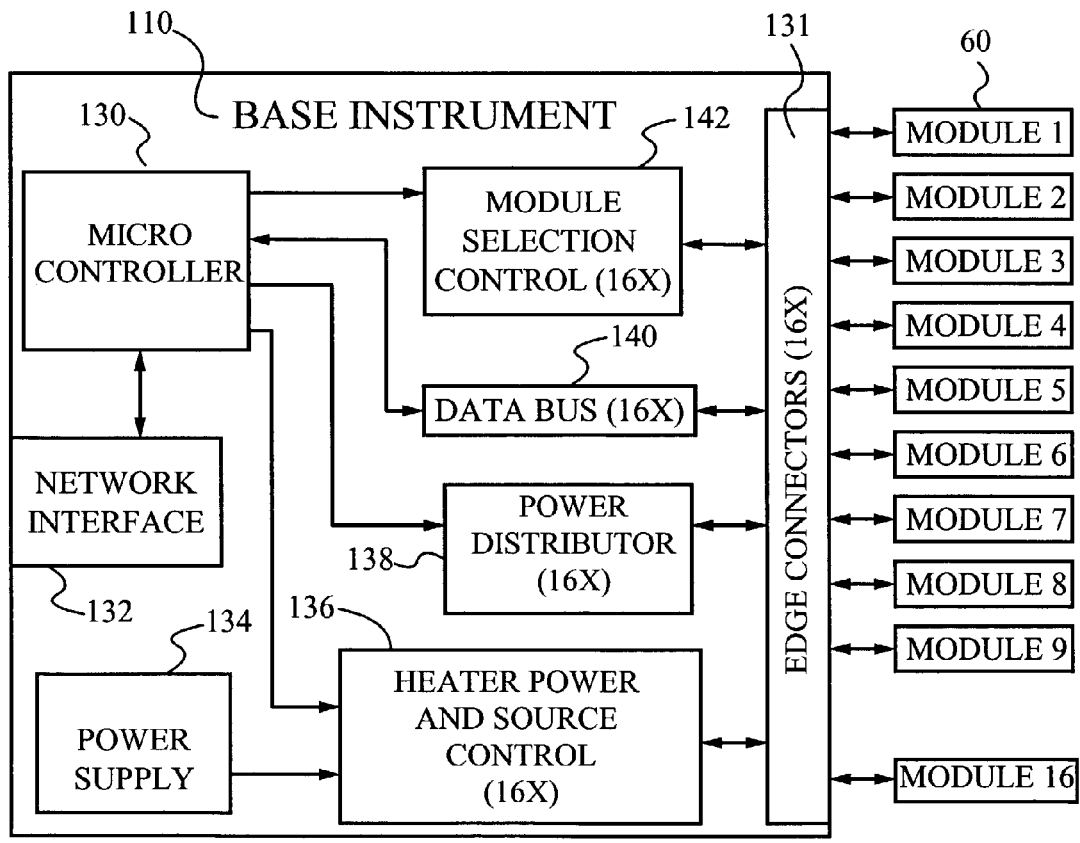
FIG. 20 is a schematic, block diagram of a base instrument of the system of FIG. 18.

FIG. 20 is a schematic, block diagram of the base instrument 110. The base instrument includes a power supply 134 for supplying power to the instrument and to each module 60. The power supply 134 may comprise an AC/DC converter for receiving power from an external source and converting it to direct current, e.g., for receiving 110V AC and converting it to 12V DC. Alternatively, the power supply 134 may comprise a battery, e.g., a 12V battery. The base instrument 110 also includes a microprocessor or microcontroller 130 containing firmware for controlling the operation of the base instrument 110 and modules 60. The microcontroller 130 communicates through a network interface 132 to the controller computer via a USB. Due to current limitations of processing power, it is currently preferred to include at least one microcontroller in the base instrument per sixteen modules 60. Thus if the base instrument has a thirty-two module capacity, at least two microcontrollers should be installed in the instrument 110 to control the modules.

The base instrument 110 further includes a heater power source and control circuit 136, a power distributor 138, a data bus 140, and a module selection control circuit 142. Due to space limitations in patent drawings, control circuit 136, power distributor 138, data bus 140, and control circuit 142 are shown only once in the block diagram of FIG. 20. However, the base instrument 110 actually contains one set of these four functional components 136, 138, 140, 142 for each heat-exchanging module 60. Thus, in the embodiment of FIG. 20, the base instrument 110 includes sixteen control circuits 136, power distributors 138, data buses 140, and control circuits 142. Similarly, the base instrument 110 also includes a different edge connector 131 for connecting to each of the modules 60, so that the instrument includes sixteen edge connectors for the embodiment shown in FIG. 20. The edge connectors are preferably 120 pin card edge connectors that provide cableless connection from the base instrument 110 to each of the modules 60. Each control circuit 136, power distributor 138, data bus 140, and control circuit 142 is connected to a respective one of the edge connectors and to the microcontroller 130.

Each heater power and source control circuit 136 is a power regulator for regulating the amount of power supplied to the heating element(s) of a respective one of the modules 60. The source control circuit 136 is preferably a DC/DC converter that receives a +12V input from the power supply 134 and outputs a variable voltage between 0 and −24V. The voltage is varied in accordance with signals received from the microcontroller 130. Each power distributor 138 provides −5 v, +5V, +12V, and GND to a respective module 60. The power distributor thus supplies power for the electronic components of the module. Each data bus 140 provides parallel and serial connections between the microcontroller 130 and the digital devices of a respective one of the modules 60. Each module selection controller 94 allows the microcontroller 130 to address an individual module 60 in order to read or write control or status information.

Figure 21:
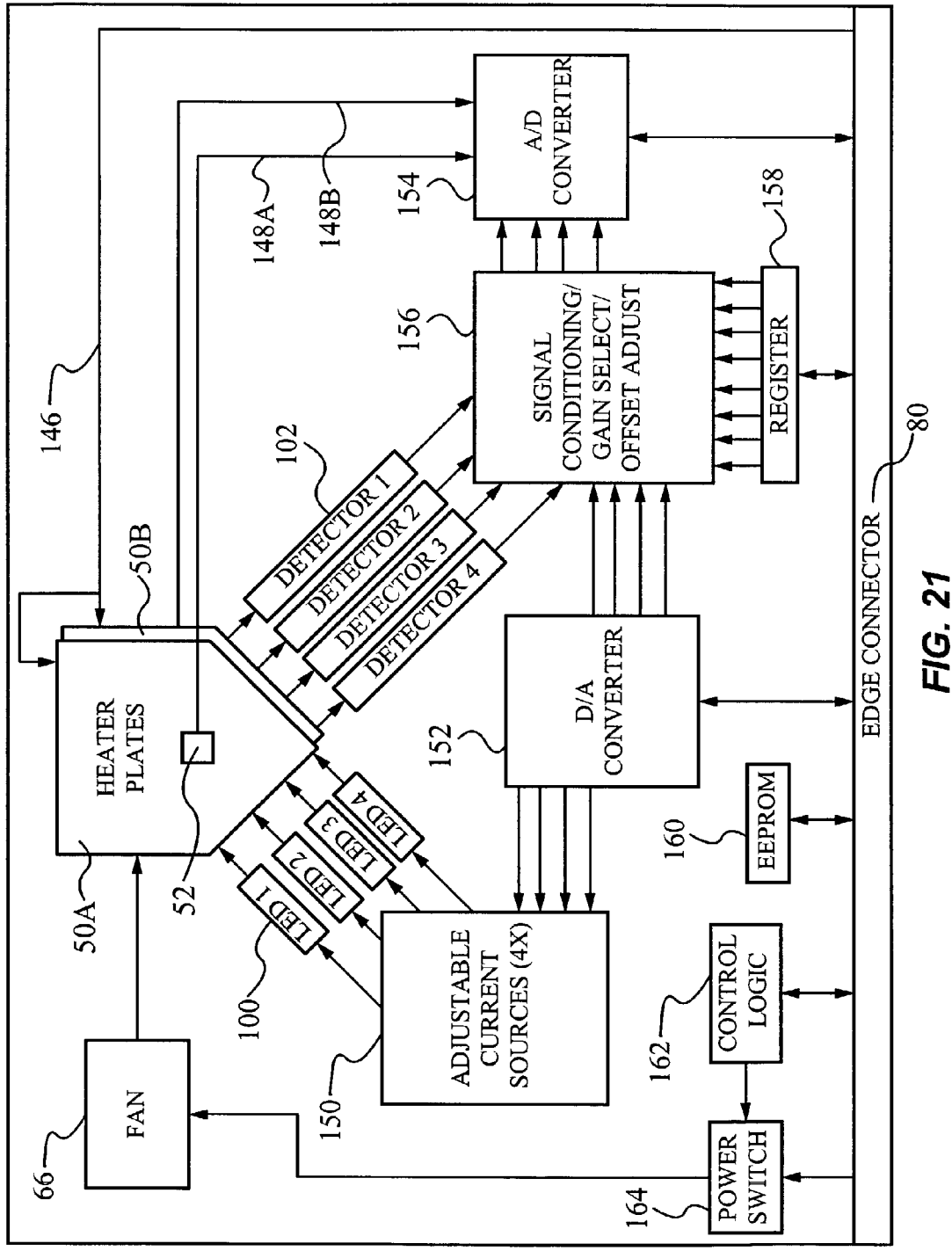
FIG. 21 is a schematic, block diagram of the electronic components of the module of FIG. 6.

FIG. 21 is a schematic, block diagram of the electronic components of a heat-exchanging module 60. Each module includes an edge connector 80 for cableless connection to a corresponding edge connector of the base instrument. The module also includes heater plates 50A, 50B each having a resistive heating element as described above. The plates 50A, 50B are wired in parallel to receive power input 146 from the base instrument. The plates 50A, 50B also include temperature sensors 52, e.g. thermistors, that output analog temperature signals to an analog-to-digital converter 154. The converter 154 converts the analog signals to digital signals and routes them to the microcontroller in the base instrument through the edge connector 80. The heat-exchanging module also includes a cooling system, such as a fan 66, for cooling the plates 50A, 50B. The fan 66 receives power from the base instrument and is activated by switching a power switch 164. The power switch 164 is in turn controlled by a control logic block 162 that receives control signals from the microcontroller in the base instrument.

The module further includes four light sources, such as LEDs 100, for excitation of labeled analytes in the sample and four detectors 102, preferably photodiodes, for detecting fluorescent emissions from the sample. The module also includes an adjustable current source 150 for supplying a variable amount of current (e.g., in the range of 0 to 30 mA) to each LED to vary the brightness of the LED. A digital-to-analog converter 152 is connected between the adjustable current source 150 and the microcontroller of the base instrument to permit the microcontroller to adjust the current source digitally. The adjustable current source 150 may be used to ensure that each LED has about the same brightness when activated. Due to manufacturing variances, many LEDs have different brightnesses when provided with the same amount of current. The brightness of each LED may be tested during manufacture of the heat-exchanging module and calibration data stored in a memory 160 of the module. The calibration data indicates the correct amount of current to provide to each LED. The microcontroller reads the calibration data from the memory 160 and controls the current source 150 accordingly. The microcontroller may also control the current source 150 to adjust the brightness of the LEDs 100 in response to optical feedback received from the detectors 102.

The module additionally includes a signal conditioning/gain select/offset adjust block 156 comprised of amplifiers, switches, electronic filters, and a digital-to-analog converter. The block 156 adjusts the signals from the detectors 102 to increase gain, offset, and reduce noise. The microcontroller in the base instrument controls block 156 through a digital output register 158. The output register 158 receives data from the microcontroller and outputs control voltages to the block 156. The block 156 outputs the adjusted detector signals to the microcontroller through the analog-to-digital converter 154 and the edge connector 80. The module also includes the memory 160, preferably a serial EEPROM, for storing data specific to the module, such as calibration data for the LEDs 100, thermal plates 50A, 50B, and temperature sensors 52, as well as calibration data for a deconvolution algorithm described in detail below.

Referring again to FIG. 18, the reactor system 106 may be configured for manual filling and pressurization of each reaction vessel 12 by a human operator. Manual use of the system is suitable for lower throughput embodiments. For higher throughput embodiments, however, the system 106 preferably includes automated machinery, e.g., a pick-and-place machine, for filling and pressurizing each of the vessels 12.

Figure 22:
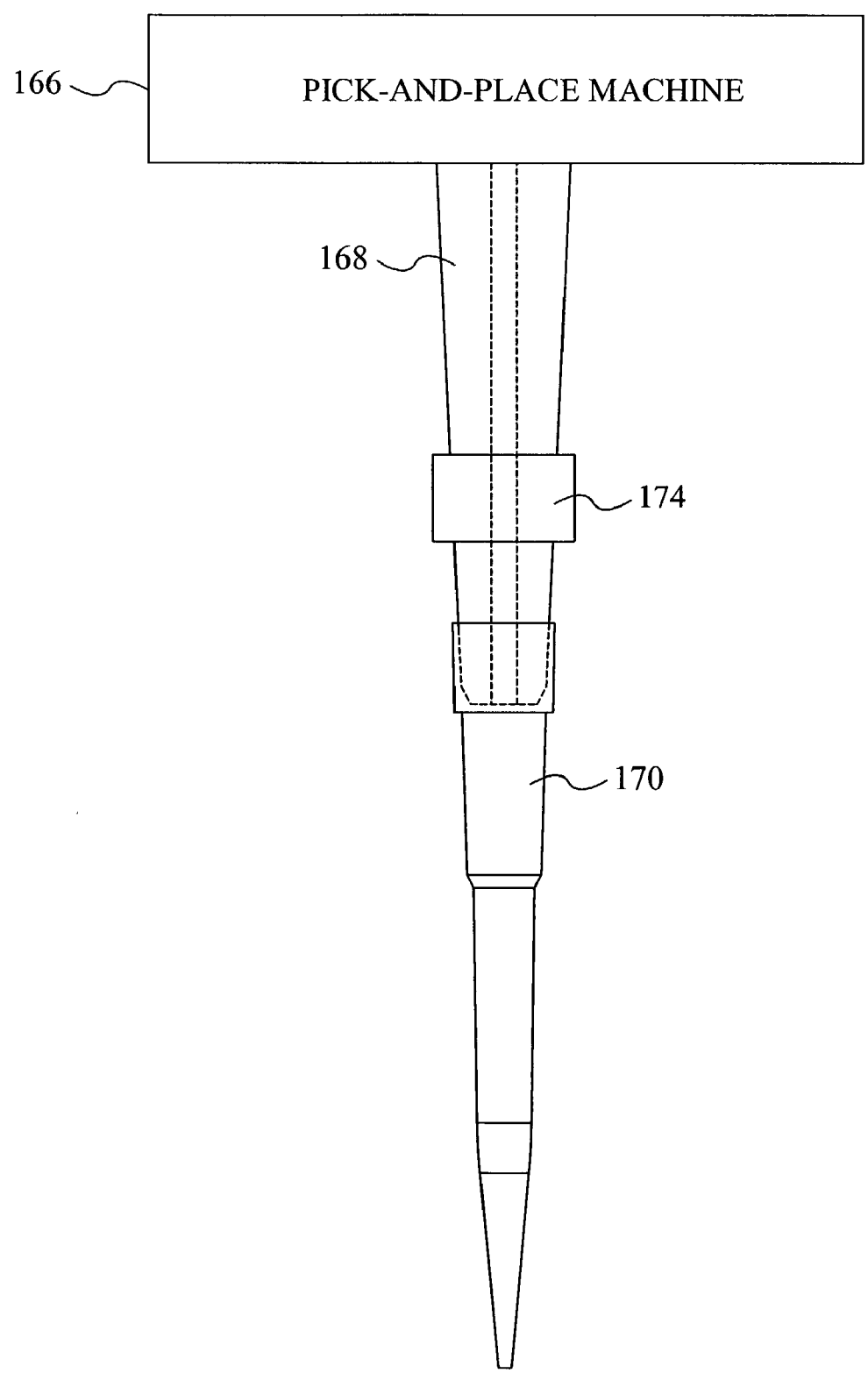
FIG. 22 is a schematic diagram of a pick-and-place machine having a pipette for filling the vessel of FIG. 1.

FIG. 22 shows a schematic diagram of a pick-and-place machine 166 for automatically filling and pressurizing a reaction vessel. The machine 166 has a machine tip 168 for engaging a disposable pipette tip 170. The machine tip 168 has an axial bore for communicating with the pipette tip 170. The machine 166 also has controllable vacuum and pressure sources in communication with the machine tip 168 for aspirating and dispensing fluids using the pipette tip 170. The vacuum and pressure sources may comprise, e.g., one or more syringe pumps, compressed air sources, pneumatic pumps, vacuum pumps, or connections to external sources of pressure.

The machine tip may also be used to pick and place a reaction vessel or to insert a plug into the vessel, as is described below with reference to FIGS. 23A–23D. The pick-and-place machine 166 also preferably includes an ejector plate 174 that slides down the machine tip 168 to eject the vessel, pipette tip, or plug from the machine tip. Referring again to FIG. 2, the loading reservoir 38 preferably includes tapered walls 40 for establishing a friction fit with the machine tip, thereby enabling the machine tip to pick and place the vessel 12. Similarly, the aspiration port 41 also preferably includes tapered walls 47 for establishing a fit with the machine tip, so that the machine tip can pick and place the vessel 12 using either the loading reservoir 38 or the aspiration port 41.

Referring again to FIG. 18, the controller 112 preferably includes software for controlling the thermal cycler 108 and the pick-and-place machine to perform the functions described in the operation section below. These functions include providing a user interface to enable a user to select desired thermal processing parameters (e.g., set point temperatures and hold times at each temperature) and optical detection parameters, automatic filling and pressurization of the vessels 12, thermal processing of the vessels according to the selected parameters, optical interrogation of the samples in the vessels, and recording of the optical data generated. The creation of software and/or firmware for performing these functions can be performed by a computer programmer having ordinary skill in the art. Moreover, the software and/or firmware may reside solely in the controller 112 or may be distributed between the controller and one or more microprocessors in the thermal cycler or pick-and-place machine. Alternatively, the controller 112 may simply be built into the thermal cycler or pick-and-place machine.

In operation, the reactor system 106 is used to thermally process and optically interrogate one or more samples. An exemplary use of the system 106 is for the amplification of nucleic acid in a sample (e.g., using PCR) and for the optical detection of one or more target analytes in the sample. A user selects a desired thermal profile for the sample using, e.g., the keyboard or mouse of the controller 112. For example, for a PCR amplification, the user may select the thermal profile to begin with a 30 second induction hold at 95° C., followed by 45 thermal cycles in which the sample is cycled between higher and lower temperatures for denaturization, annealing, and polymerization. For example, each thermal cycle may include a first set point temperature of 95° C. which is held for 1 second to denature double-stranded DNA, followed by a second set point temperature of 60° C. which is held for 6 seconds for annealing of primers and polymerization.

Figure 23D:
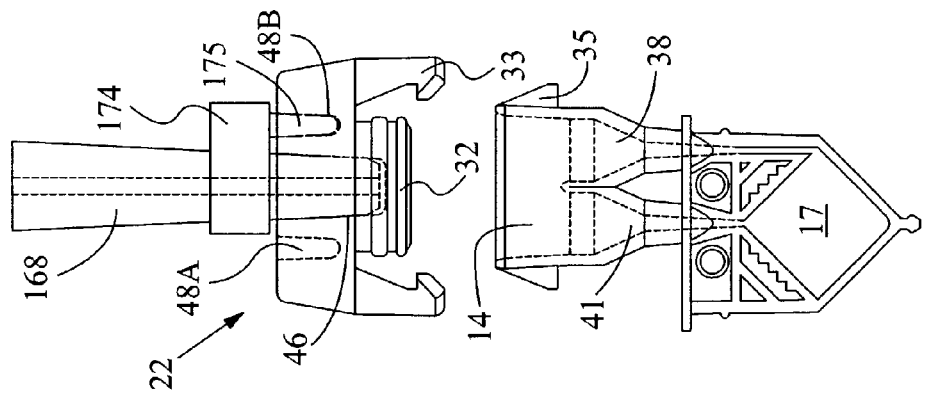
FIGS. 23A–23D are schematic diagrams of the pick-and-place machine of FIG. 22 filling and pressurizing a reaction vessel.
Figure 23C:
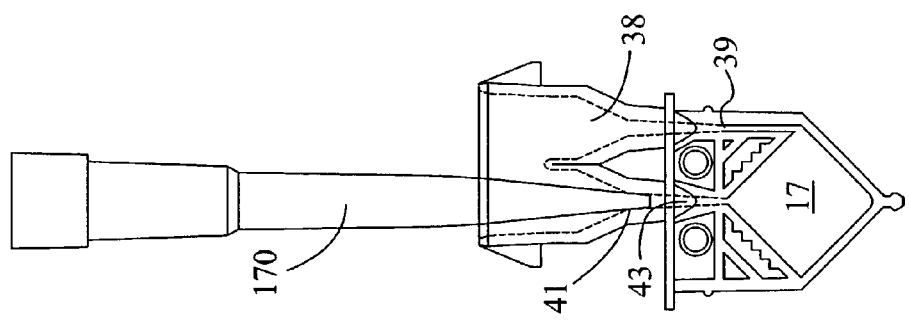
Figure 23B:
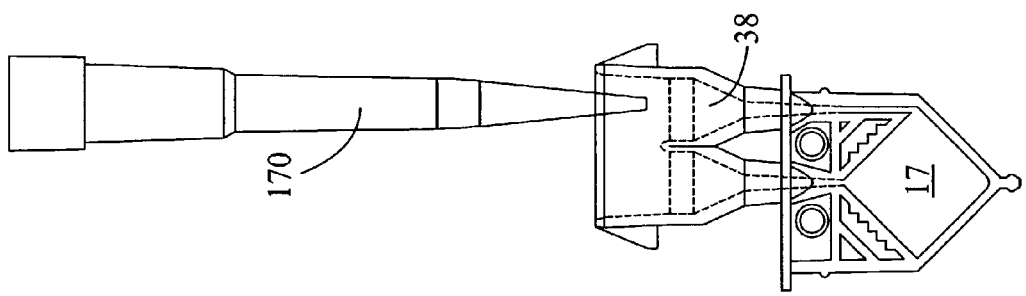
Figure 23A:
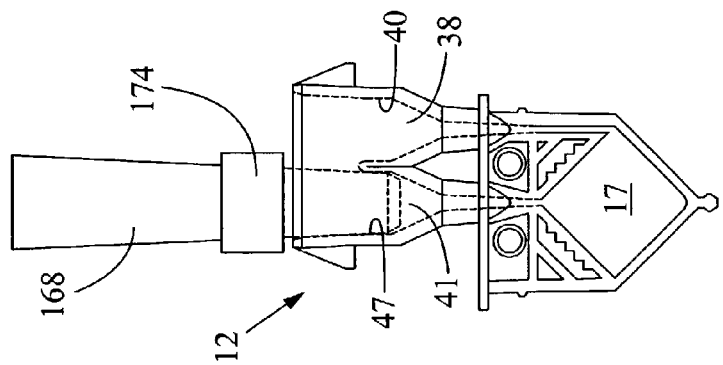

FIGS. 23A–23D illustrate a preferred procedure for loading the sample into the vessel 12 and for sealing and pressurizing the vessel. Referring to FIG. 23A, an empty vessel 12 is first picked up by the machine tip 168 and placed into one of the heat-exchanging modules. To pick up the vessel 12, the machine tip 168 is inserted into the aspiration port 41 so that the tip 168 establishes a friction fit with the tapered walls 47. Once the vessel 12 is inserted between the plates of a heat-exchanging module, the ejector plate 174 ejects the vessel from the machine tip 168.

As shown in FIG. 23B, the machine tip next picks up the pipette tip 170, and the sample is aspirated into the pipette tip. The sample is then dispensed into the loading reservoir 38 using the pipette tip 170. The sample may be mixed with chemicals necessary for the intended reaction (e.g., PCR reagents and/or fluorescent probes) prior to being added to the loading reservoir 38. Alternatively, the reagents may be added to the loading reservoir 38 before or after the sample so that the reagents and sample are mixed together in the reservoir 38. In another embodiment, the sample is introduced to the chemicals or reagents in the chamber 17. For example, the necessary reagents and/or fluorescent probes for the intended reaction may be placed in the chamber 17 when the vessel is manufactured. The reagents are preferably placed in the chamber 17 in dried or lyophilized form so that they are adequately preserved until the vessel is used. When the fluid sample is added to the chamber, it reconstitutes the dried or lyophilized reagents to form the desired reaction mixture.

Referring to FIG. 23C, after the sample and/or reagents are dispensed into the loading reservoir 38, the pipette tip 170 is inserted into the aspiration port 41. The pipette tip 170 establishes annular seal with the tapered walls of the aspiration port 41 and applies vacuum pressure to the sample in the loading reservoir 38. The vacuum pressure is applied to the sample through the channel 43, chamber 17, and channel 39. In this manner, the pipette 170 draws (aspirates) the sample from the loading reservoir 38 into the chamber 17. Loading the sample into the chamber 17 in this manner reduces the likelihood of any air bubbles forming in the chamber. Air bubbles would have a negative effect on subsequent optical detection of target analytes in the sample. Following loading of the sample into the chamber 17, the pipette tip 170 is ejected.

As shown in FIG. 23D, the machine tip 168 then engages the cap 36 of the plug 22 and inserts the plug into the aperture 14, thereby simultaneously sealing the chamber 17, loading reservoir 38, and aspiration port 41 from the environment external to the vessel. The cap 36 includes a tapered engagement aperture 46 for receiving and establishing a friction fit with the machine tip 168. The machine tip 168 also preferably includes an alignment pin 175 for aligning the plug 22 in a desired angular orientation with respect to the aperture 14 (i.e., so that the oval-shaped plug fits into the correspondingly oval-shaped aperture). The alignment pin 175 provides a convenient mechanism for rotating the cap to the necessary angular orientation before inserting the plug 22 into the aperture 14. The cap 36 includes alignment apertures 48A, 48B, either one of which may receive the alignment pin 175. As the plug 22 is inserted, the sealing ring 32 seals the aperture 14 and the plug 22 compresses gas in the vessel to increase pressure in the chamber 17, preferably to about 8 to 15 psi above ambient pressure, as previously discussed with reference to FIGS. 24A–24B. When the plug 22 is inserted into the aperture 14, the catches 35 engage the latches 33 to lock the plug 22 in place. After the plug 22 is inserted, the ejector plate 174 ejects the plug 22 from the machine tip 168.

Although this embodiment of the pick-and-place machine is presently preferred, many other embodiments are possible. For example, the machine tip 168 may be designed to establish a vacuum fit with the cap 36. Alternatively, the pick-and-place machine may have a robotic gripper arm for gripping the plug 22 and inserting it into the aperture 14. Suitable pick-and-place machines for use in the system of the present invention are commercially available as machines built to specification from several suppliers, such as Tecan U.S. Inc. located at 4022 Stirrup Creek Drive, Durham, N.C. 27703.

Many modifications to the procedure described above for filling and pressurizing the vessel 12 are possible. For example, the vessel 12 may be inserted between the plates of a respective heat-exchanging module after the vessel is filled and pressurized rather than before. In this embodiment, the vessel 12 is preferably held in a rack, tray, or similar support device during filling and pressurization. After the vessel 12 is filled and capped, the machine tip 168 picks up the vessel 12 by the cap 36 and inserts the chamber 17 of the vessel between the plates of a heat-exchanging module. The plug 22 is held in the aperture 14 during this movement by the latches 33 that engage the catches 35. After the vessel 12 is inserted, the ejector plate 174 ejects the cap 36 from the machine tip 168. The latches 33 are also effective for holding the cap 36 on the vessel 12 as the vessel is removed from the module after thermal processing and optical detection. Although automated filling and pressurization of the vessel 12 has been described herein, it is to be understood that the vessel may also be filled and pressurized manually by a human operator using, e.g., a pipette and human hands.

Referring again to FIG. 18, once a filled and pressurized reaction vessel 12 is placed between the thermal plates of a heat-exchanging module 60, the sample contained in the vessel is subjected to the thermal profile selected by the user. The controller 112 implements proportional-integral-derivative (PID) control to execute the selected thermal profile. Referring again to FIG. 21, the controller receives signals indicating the temperatures of the plates 50A, 50B from the temperature sensors 52. Polling of the plate temperatures preferably occurs every 100 milliseconds throughout the running of the temperature profile. After each polling, the controller averages the temperatures of the two plates 50A, 50B to determine an average plate temperature. The controller then determines the difference (delta) between the profile target temperature, i.e. the set point temperature defined by the user for the particular time in the profile, and the average plate temperature. Based on the relationship between the average plate temperature and the current target temperature, the controller controls the amount of power supplied to the heating elements on the plates 50A, 50B or to the fan 66 as appropriate to reach or maintain the current set point temperature. Standard PID control is well known in the art and need not be described further herein. The controller may optionally implement a modified version of PID control described in International Publication Number WO 99/48608 published Sep. 30, 1999, the disclosure of which is incorporated by reference herein.

Referring again to FIGS. 14 and 16, the sample in the vessel 12 is optically interrogated in real-time as the thermal profile is executed to determine if the sample contains one or more target analytes (e.g., nucleic acid sequences of interest). The sample is preferably optically interrogated once per thermal cycle at the lowest temperature in the cycle. Optical interrogation is preferably accomplished by sequentially activating LEDs 100A, 100B, 100C, and 100D to excite different fluorescently-labeled analytes in the sample and by detecting light emitted (fluorescent output) from the chamber 17 using detectors 102A, 102B, 102C, and 102D. Specific techniques for detecting analytes that labeled with dyes or probes are known in the art. Suitable examples of operation of the optical detection system of FIGS. 14–17 are given in commonly assigned U.S. Pat. No. 6,369,893 "Multi-Channel Optical Detection System" the disclosure of which is incorporated by reference herein.

In a typical implementation of the four-channel system, three of the optical channels are used to detect target analytes (e.g., amplified nucleic acid sequences) while the fourth channel is used to monitor an internal control to check the performance of the system. For example, beta actin is often used as an internal control in nucleic acid amplification reactions because it has a predictable amplification response and can be easily labeled and monitored to verify that the amplification is occurring properly.

One advantage of the system of the preferred embodiment is that it provides extremely rapid heating and cooling of a sample. This rapid heating and cooling is particularly beneficial for nucleic acid amplification because of the increased speed with which the amplification may be accomplished and because it significantly reduces the likelihood of creating unwanted and interfering side products, such as PCR "primer-dimers" or anomalous amplicons. Another advantage of the system is that it provides for sensitive, real-time detection of one or more analytes in a sample as the reaction is performed. Another advantage is that the loading structure of the reaction vessel provides for an extremely clean fill of the chamber without the formation of air bubbles that would be detrimental to optical detection. The loading reservoir and aspiration port also eliminate the need to insert the pipette into the chamber 17. Consequently, the thickness of the chamber is not limited by the minimum practical pipette diameter which can be employed in the sample transfer process. Thus, the chamber can have a thickness less than the width or diameter of the aspiration device.

Figure 30:
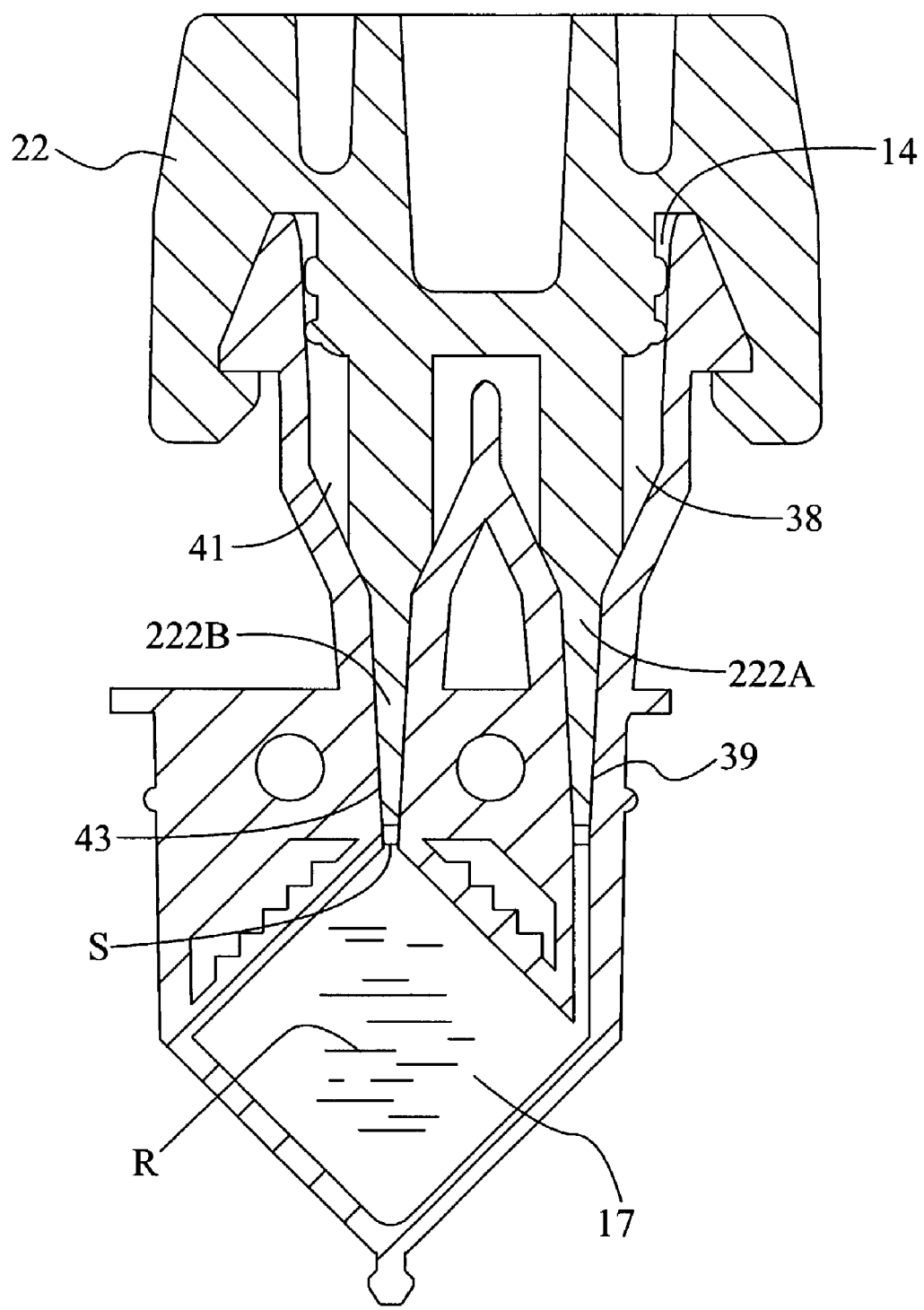
FIG. 30 is a schematic, cross sectional view of a reaction vessel according to another embodiment of the invention.

FIG. 30 shows another embodiment of the invention in which the plug 22 includes first and second tongues 222A, 222B extending from the main body of the plug. The first tongue 222A is sized to be inserted into the inlet channel 39 that connects the loading reservoir 38 to the chamber 17. Similarly, the second tongue 222B is sized to be inserted into the outlet channel 43 that connects the aspiration port 41 to the chamber 17. The tongues 222A, 222B are positioned with respect to the main body of the plug 22 such that when the plug 22 is inserted into the aperture 14, the plugs 222A, 222B are inserted into the channels 39 and 43, respectively. The tongues 222A, 222B provide a physical obstacle for preventing the reaction mixture R in the chamber 17 from refluxing (i.e. bubbling up or evaporating) into the loading reservoir 38 or aspiration port 41 as the mixture is heated. The tongues 222A, 222B thus prevent some vapor loss from the chamber 17 as the reaction mixture R is thermally processed. The tongues 222A, 222B should not form a seal with the walls of the channels 39, 43. Such sealing would cause the chamber 17 to become hydraulically locked, which is undesirable. Such a hydraulically locked condition could result in damage to the major walls 18 or plates 50A, 50B (FIG. 4) and/or prevent the major walls 18 from conforming to the surfaces of the plates 50A, 50B.

Figure 25A:
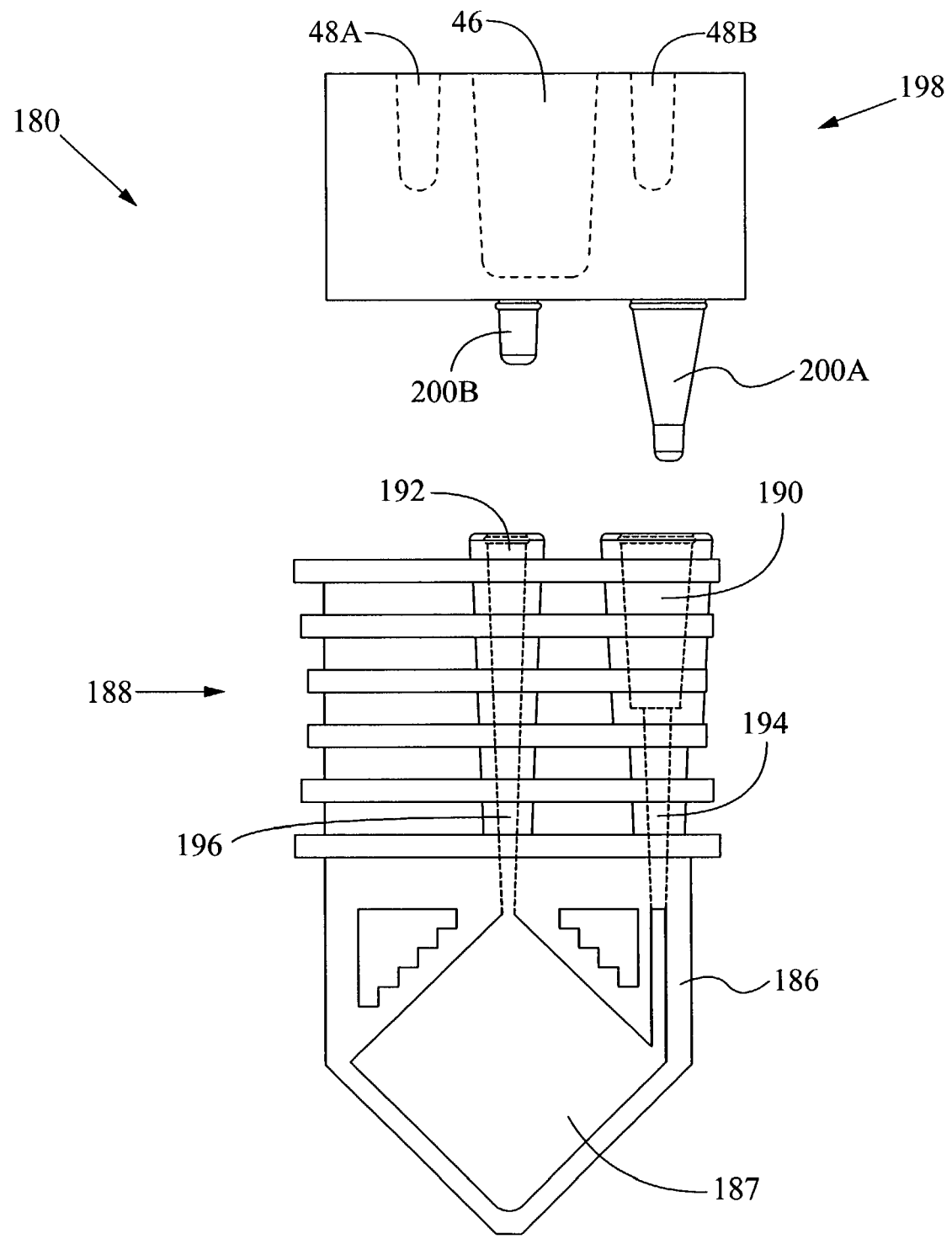
FIG. 25A is a schematic, front view of a reaction vessel according to another embodiment of the invention.

FIG. 25A shows a reaction vessel 180 according to another embodiment of the invention. Like the vessel of FIG. 2A, the vessel 180 has a rigid frame 186 defining the side walls of a reaction chamber 187, flexible sheets attached to opposite sides of the frame 186 to form opposing major walls of the chamber, and a loading structure 188 extending from the frame 186 for loading a sample into the chamber. The loading structure 188 is preferably integrally molded with the frame 186. The loading structure 188 defines a loading reservoir 190 connected to the chamber 187 by an inlet channel 194. The loading structure 188 also defines an aspiration port 192 connected to the chamber 187 by an outlet channel 196. The aspiration port 192 has tapered walls for establishing a seal with an aspiration device (e.g., a pipette tip), thereby enabling the aspiration device to draw the sample from the loading reservoir 190 into the chamber 187.

The vessel 180 differs from the vessel of FIG. 2A in the mechanism for sealing and pressurizing the vessel. The vessel 180 includes a cap 198 having first and second plugs 200A, 200B for sealing the loading reservoir 190 and the aspiration port 192, respectively, and for compressing gas in the vessel, thereby increasing pressure in the chamber 187. The cap 198 may optionally include an engagement aperture 46 for receiving and establishing a fit with a machine tip. The cap 198 may also include alignment apertures 48A, 48B for receiving alignment pins to permit automated picking and placing of the cap by a pick-and-place machine.

Figure 25B:
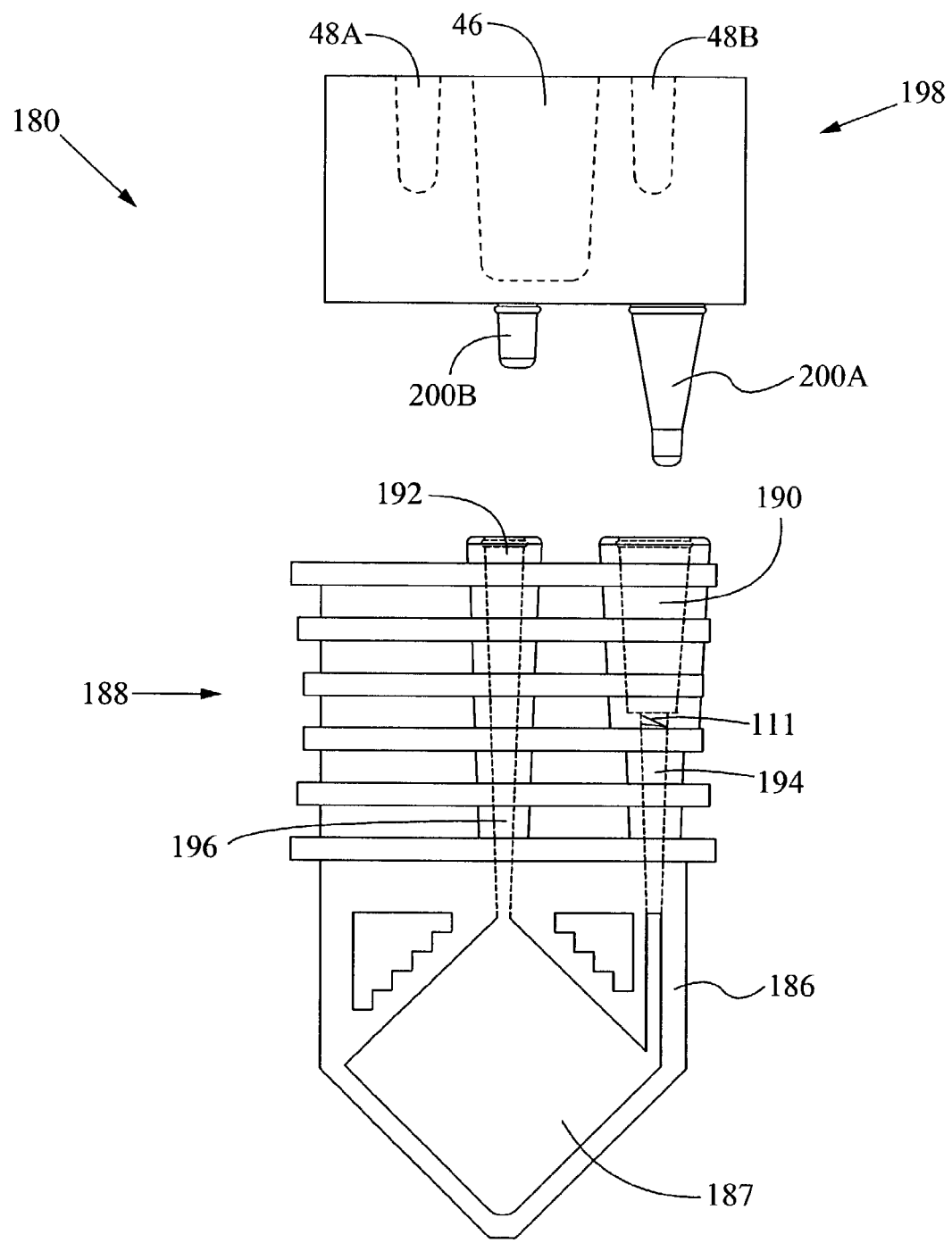
FIG. 25B is a schematic, front view of a reaction vessel having a valve according to another embodiment of the invention.
Figure 25C:
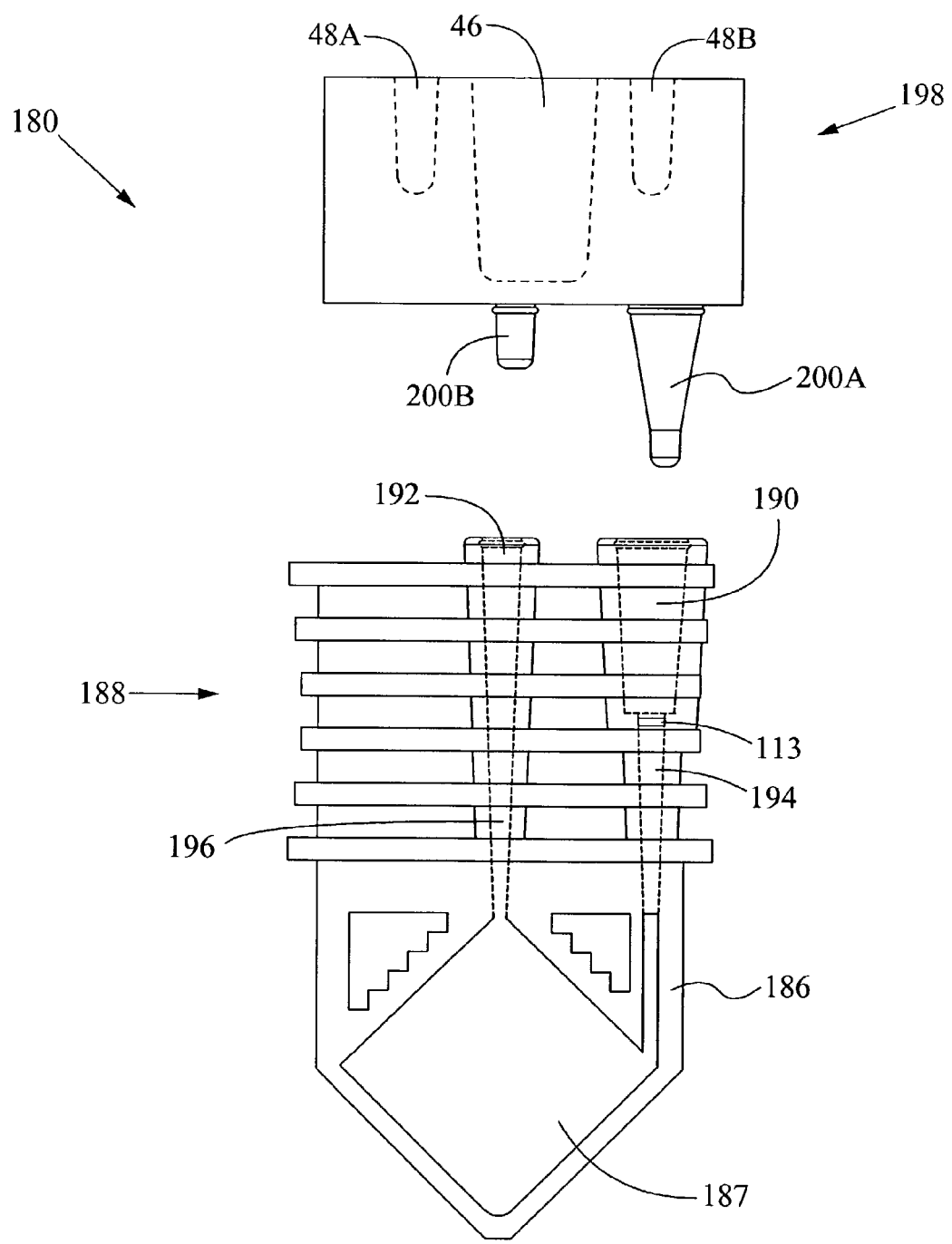
FIG. 25C is a schematic, front view of a reaction vessel having a membrane or screen according to another embodiment of the invention.

The vessel 180 preferably includes flow control means for preventing substantial flow of the sample from the loading reservoir 190 to the reaction chamber 187 until the sample is drawn into the chamber 187 by an aspiration device. As previously described, suitable flow control means include, but are not limited to: a channel having a narrow width or diameter; one or more valves; one or more membranes; or one or more screens. FIG. 25A shows one embodiment of the vessel in which the flow control means is at least one portion of the channel 194 having a sufficiently small width or diameter (e.g., 0.031 inches or less is suitable for most aqueous solutions having the viscosity of water) to prevent substantial flow of the sample (e.g., due to gravitational force) from the loading reservoir 190 to the chamber 187 until the sample is drawn into the chamber by application of a vacuum to aspiration port 192. FIG. 25B shows another embodiment of the vessel in which the flow control means is a valve 111 in the channel 194. There are many types of valves known in the art that are suitable for this purpose including, e.g., a flap valve, check valve, or rotary valve. FIG. 25C shows another embodiment of the vessel in which the flow control means is a membrane or screen 113 in the channel 194. Suitable membranes include, e.g., burstable or piercable membranes that are burst or pierced to permit fluid flow through the channel 194. If a screen is used as the flow control component, the screen should have a pore size sufficient to prevent substantial flow of the sample before a vacuum is applied to the aspiration port 192 and permit flow of the sample when the vacuum is applied.

In operation, a sample is dispensed into the loading reservoir 190 using an aspirating and dispensing device, e.g. a pipette. The pipette tip is then inserted into the aspiration port 192 such that the pipette tip establishes a seal with the tapered walls. The sample is then drawn (aspirated) from the loading reservoir 190 into the chamber 187 by application of vacuum pressure to the aspiration port 192. Following loading of the sample into the chamber 187, the cap 198 is placed on the vessel 180 such that the plugs 200A, 200B are inserted into the loading reservoir 190 and aspiration port 192, respectively. The plugs 200A, 200B should be designed to seal the loading reservoir 190 and aspiration port 192, respectively, at exactly the same time. Otherwise, the sample may be forced to squirt out of the loading reservoir 190 or the aspiration port 192. For this reason, the vessel described in FIGS. 1–2A is presently preferred. The sealing aperture 14 ensures perfect sealing and pressurization of the vessel.

Figure 26:
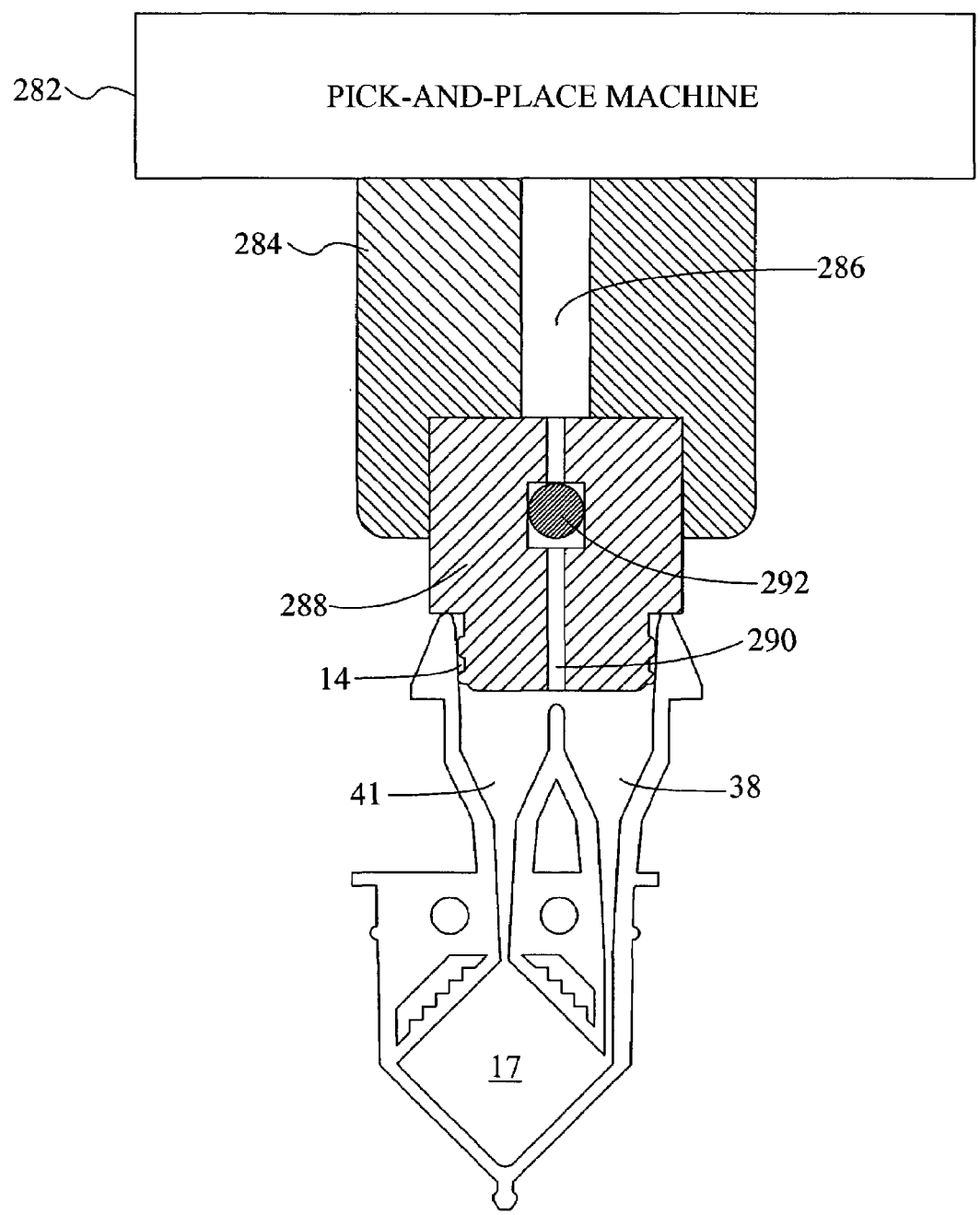
FIG. 26 is a schematic diagram of a pick-and-place machine for pressurizing a reaction vessel according to another embodiment of the invention.

FIG. 26 shows an alternative embodiment of the invention in which the pressurization of the vessel 12 is performed by a pick-and-place machine 282 having a machine head 284. The machine head 284 has an axial bore 286 for communicating with the chamber 17 through the loading reservoir 38 and aspiration port 41. The pick-and-place machine 282 also includes a regulated pressure source in fluid communication with the bore 286 for pressurizing the vessel 12 through the bore 286. The pressure source may comprise, e.g., a syringe pump, compressed air source, pneumatic pump, or connection to an external air supply.

The system also preferably includes a disposable adapter 288 for placing the bore 286 in fluid communication with the chamber 17. The adapter 288 has an axial bore 290 that connects the bore 286 in the machine head to the aperture 14 in the vessel. The adapter 288 is sized to be inserted into the aperture 14 such that the adapter establishes a seal with the walls of the aperture. The adapter 282 preferably comprises an elastomeric material, e.g., a thermalplastic elastomer (TPE) or silicone. The adapter 288 preferably includes a one-way valve 292 (e.g., a check valve) for preventing fluid from escaping from the vessel 12.

In operation, the vessel 12 is preferably placed into a heat-exchanging module and filled with a sample as previously described in the preferred embodiment. The vessel may be filled manually by a human operator, or alternatively, the pick-and-place machine 282 may include a pipette for filling the vessel. After the chamber 17 is filled with the sample, the machine head 284 picks up the adapter 288 and inserts the adapter into the aperture 14. To pick and place the adapter 288, the machine head 284 preferably has a collet for gripping and releasing the adapter 288. Alternatively, the machine head may be sized to establish a press or friction fit with the adapter 288. When inserted into the aperture 14, the adapter 288 establishes a seal with the walls of the aperture.

The pick-and-place machine 282 then transmits gas, preferably air, from the pressure source into the vessel 12 to increase the pressure in the chamber 17. The flow of air into the vessel 12 is stopped when the desired pressurization of the chamber 17 is achieved.

The desired pressurization of the chamber 17 in this embodiment is the same as that described in the preferred embodiment above. As shown in FIG. 4, the pressure in the chamber 17 should be sufficiently high to ensure that the flexible major walls 18 of the chamber outwardly expand to contact and conform to the surfaces of the plates 50A, 50B. The pressure should not be so great, however, that the walls 18 burst, become unattached from the frame 16, or deform the frame or plates. It is presently preferred to pressurize the chamber 17 to a pressure in the range of 2 to 50 psi above ambient pressure. This range is preferred because 2 psi is generally enough pressure to ensure conformity between the flexible walls 18 and the surfaces of the plates 50A, 50B, while pressures above 50 psi may cause bursting of the walls 18 or deformation of the frame 16 or plates 50A, 50B. More preferably, the chamber 17 is pressurized to a pressure in the range of 8 to 15 psi above ambient pressure. This range is more preferred because it is safely within the practical limits described above to allow for any manufacturing or operational deviations from specification.

Referring again to FIG. 26, the machine head 284 is disengaged from the adapter 288 following the pressurization of the vessel 12. When the machine head 284 is disengaged from the adapter 288, the valve 292 prevents fluid from escaping from the vessel 12. Thus, the chamber 17 remains pressurized for thermal processing and the vessel 12 is effectively sealed to prevent the sample in the vessel from contaminating the external environment. The remaining operation of this embodiment is analogous to the operation of the preferred embodiment described above.

Figure 27:
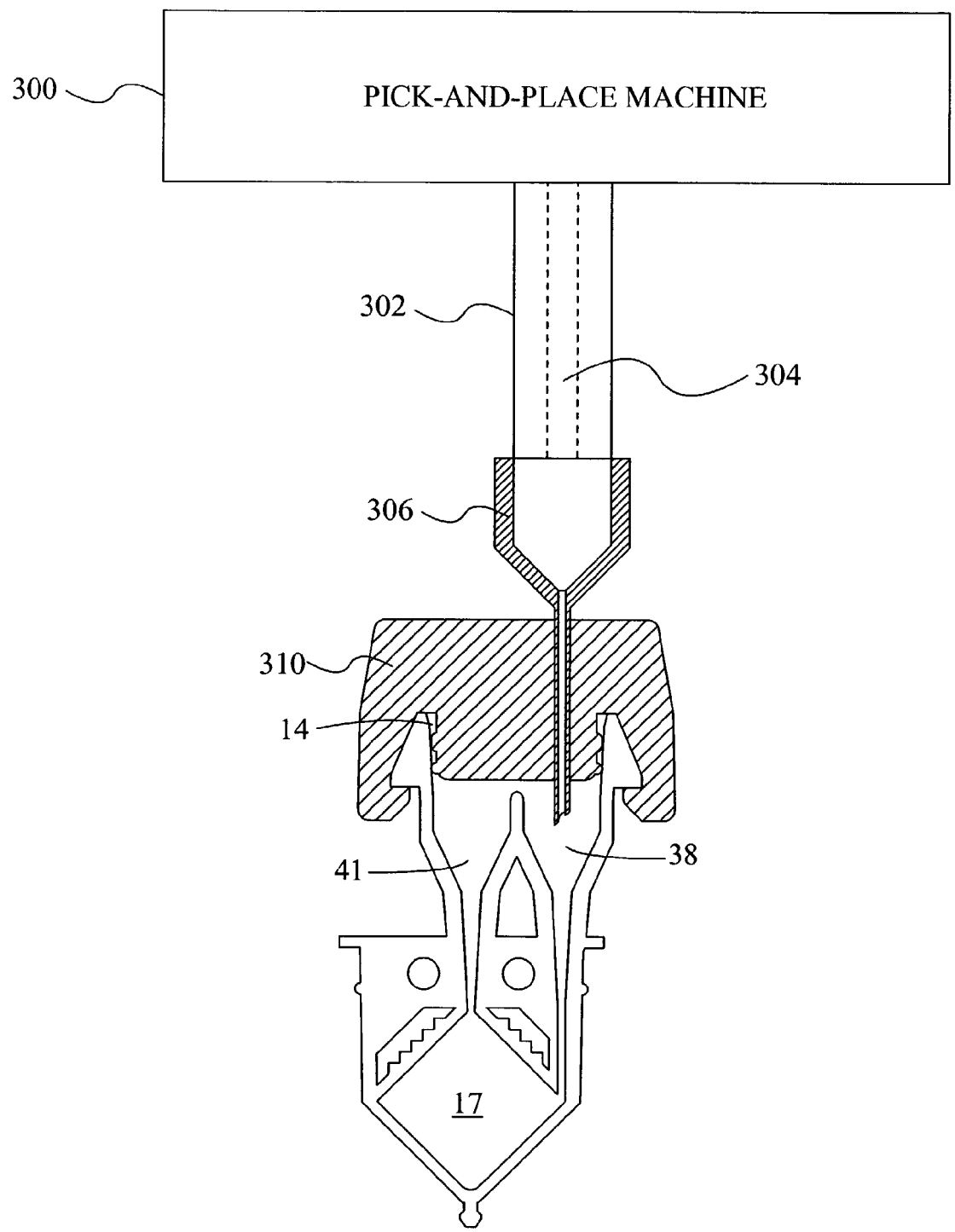
FIG. 27 is a schematic diagram of a pick-and-place machine using a needle to pressurize a reaction vessel according to an alternative embodiment of the invention.

FIG. 27 shows another embodiment of the invention in which the pressurization of vessel 12 is performed by a pick-and-place machine 300 having a machine head 302 for manipulating a needle 306. The machine head 302 has an axial bore 304 for communicating with the needle 306. The pick-and-place machine 300 has controllable vacuum and pressure sources in communication with the bore 304 for aspirating and dispensing fluids using the needle 306. The vacuum and pressure sources may comprise, e.g., one or more syringe pumps, compressed air sources, pneumatic pumps, vacuum pumps, or connections to external sources of pressure. The machine head 302 engages the needle 306 using any standard needle fitting, such as a luer lock.

The system also includes an elastomeric plug 310 that is inserted into the aperture 14 of the vessel such that the plug forms a seal with the walls of the aperture. The needle 306 is inserted through the plug 310 by the machine head 302 to pressurize the chamber 17. The elastomeric plug 310 should be self-sealing so that it seals fluid within the vessel 12 when the needle 306 is withdrawn from the plug 310. The plug 310 may be inserted into the aperture 14 by a robotic arm or machine tip of the pick-and-place machine 300 or the plug may be manually inserted by a human operator.

In operation, the vessel 12 is preferably placed into a heat-exchanging module and filled with a sample as previously described in the preferred embodiment. The vessel may be filled manually by a human operator, or alternatively, the pick-and-place machine 300 may include a pipette for filling the vessel. After the chamber 17 is filled with the sample, the self-sealing plug 310 is inserted into the aperture 14. The machine head 302 then inserts the needle 306 through the plug 319 so that the tip of the needle is inside the vessel 12. The pick-and-place machine 300 then flows gas, preferably air, from the controllable pressure source into the vessel 12 through the needle 306 to increase pressure in the chamber 17. The machine 300 then stops the flow of air when the desired pressurization of the chamber 17 is achieved.

The desired pressurization of the chamber 17 in this embodiment is the same as that described in previous embodiments, e.g., 5 to 50 psi and more preferably 8 to 15 psi for the reasons discussed above. Following pressurization, the machine head 302 retracts the needle 306 from the plug 310, and the plug 310 self seals to maintain the desired pressure in the vessel 12 for thermal processing. The remaining operation of this embodiment is analogous to the operation of the preferred embodiment described above.

Figure 28:
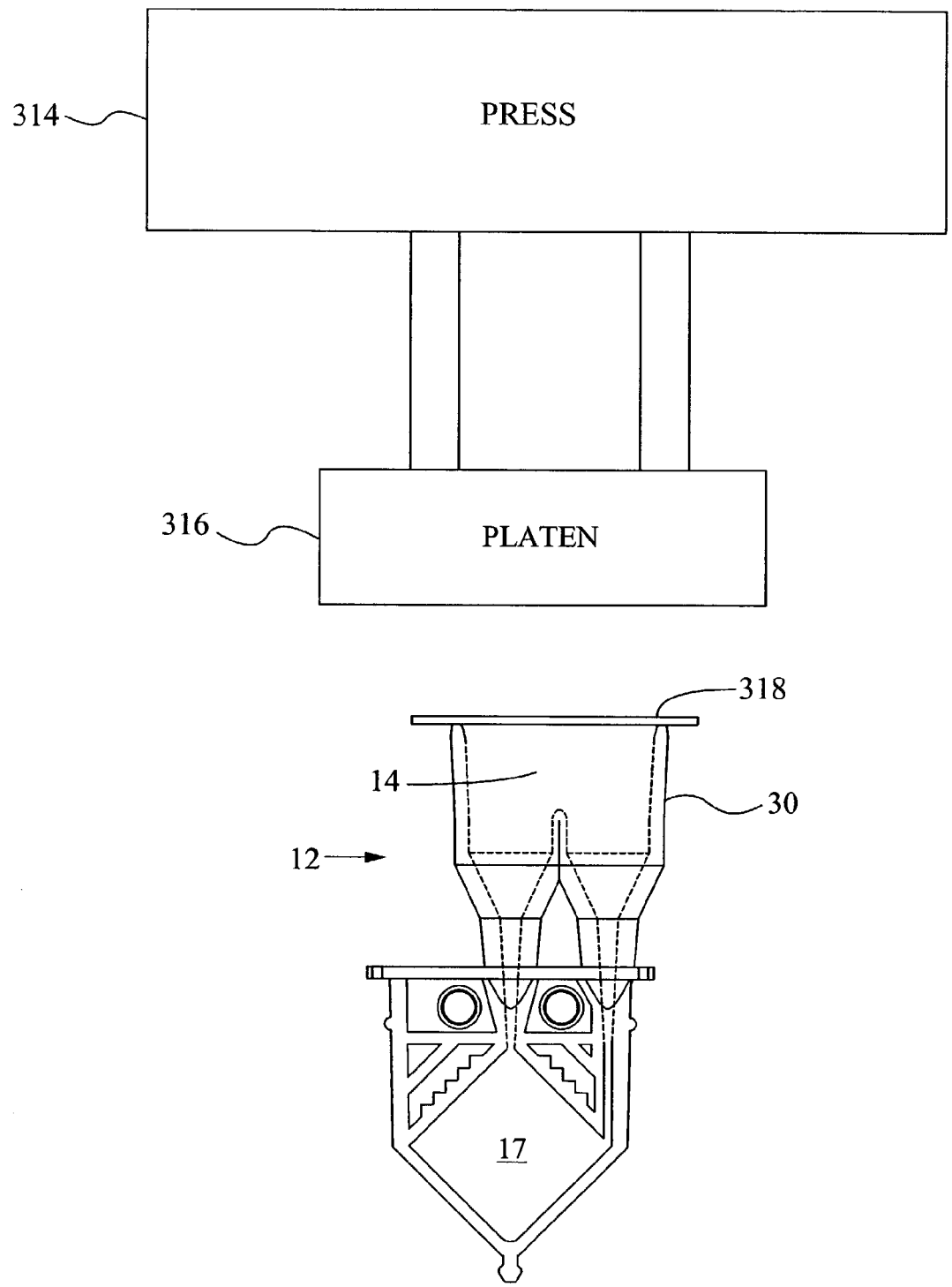
FIGS. 28–29 are schematic diagrams of a press machine having a platen for sealing a port of a reaction vessel according to another embodiment of the invention.

FIG. 28 shows another embodiment of the invention in which the sealing and pressurization of vessel 12 is performed by a press 314 having a heated platen 316 for heat sealing a film or foil 318 to the portion of the loading structure 30 forming the seal aperture 14. The foil 318 is preferably a laminate comprising a layer of metal (e.g., aluminum) on top of a layer of polymeric material (e.g., polypropylene or polyester). In operation, the vessel 12 is preferably placed in a holder (e.g., a tray or nest) that moves on an assembly line for automated filling, sealing, and pressurization of the vessel. In a first step, the chamber 17 of the vessel is filled with a sample as previously described in the preferred embodiment. After the chamber 17 is filled, the foil 318 is placed on top of the loading structure 30 with the metal layer facing up. The foil 318 may be placed on the vessel manually by a human operator, or more preferably, by the robotic arm of a pick-and-place machine. The vessel 12 is then moved under the heated platen 316 for sealing and pressurization. The platen 316 is then pressed to the top of the vessel 12 and the platen 316 heat seals the foil 318 to the vessel to seal the aperture 14.

Figure 29:
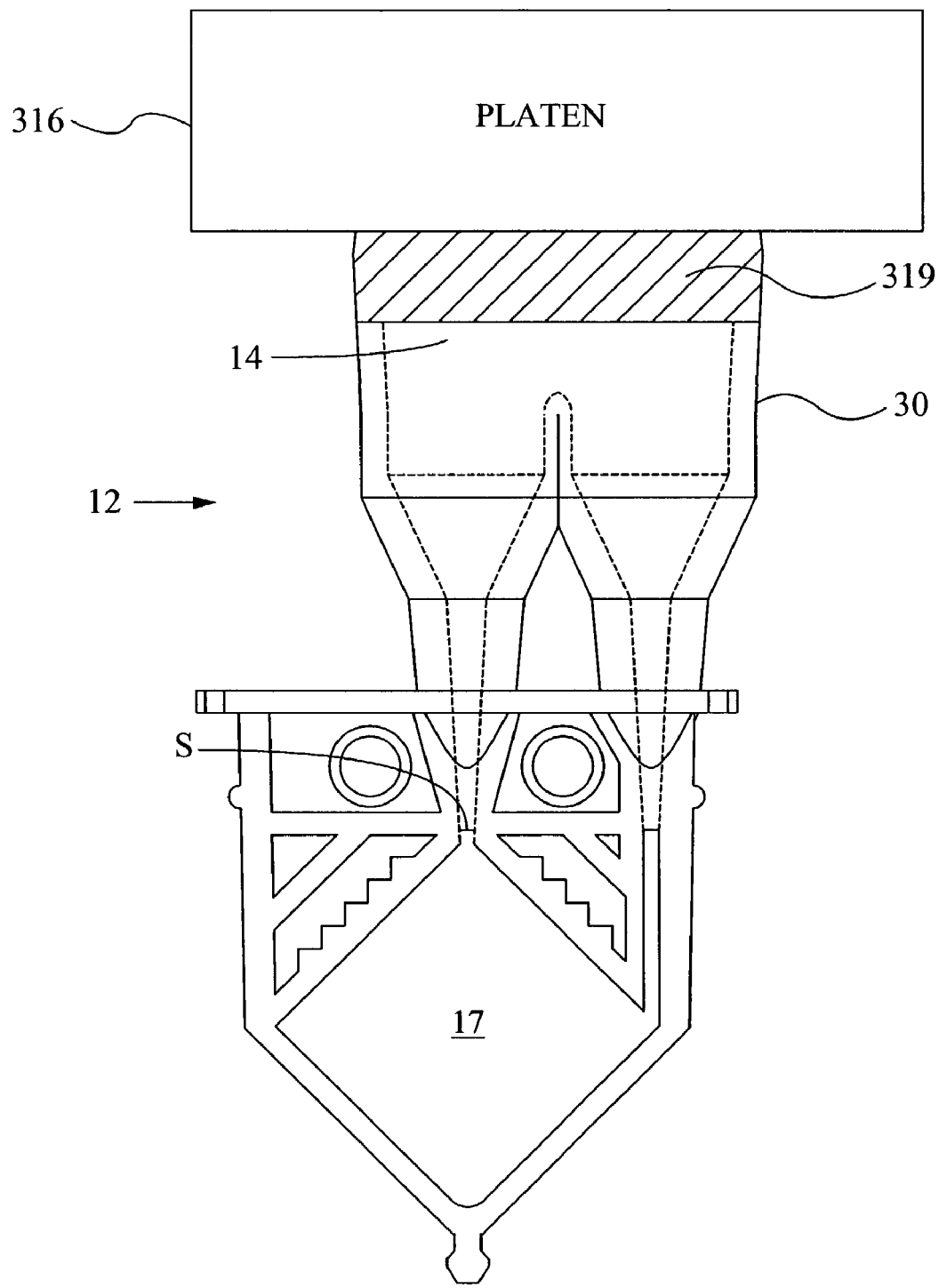

As shown in FIG. 29, the heat from the platen 316 also melts the top portion of the loading structure 30, thereby collapsing an end of the aperture 14 to produce a collapsed zone 319. The volume capacity of the vessel 12 is therefore reduced. The reduction of the volume capacity of the vessel 12 after the port is sealed compresses air trapped in the vessel and causes the desired pressurization of the chamber 17. The desired pressurization of the chamber 17 in this embodiment is the same as that described in the previous embodiments, e.g., 2 to 50 psi above the ambient pressure, and more preferably 8 to 15 psi above the ambient pressure. After the vessel 12 is sealed and pressurized in this manner, it is picked and placed into one of the heat-exchanging modules 60 (FIG. 18) for thermal processing and optical detection. The remaining operation of this embodiment is the same as the operation of the preferred embodiment described above.

The desired pressurization of the chamber 17 may be achieved by use of the equation:

$$P_i * V_i = P_f * V_f$$

where:

$P_i$ is equal to the initial pressure in the vessel 12 prior to sealing the aperture;

$V_i$ is equal to the volume capacity of the vessel between the surface level S and the top of the aperture 14 prior to sealing the vessel;

$P_f$ is equal to the desired final pressure in the chamber 17; and $V_f$ is equal to the final volume capacity of the vessel between the surface level S and the collapsed zone 319.

To ensure the desired final pressure $P_f$ in the chamber 17, the heat-sealing of the vessel should reduce the volume capacity of the vessel such that the ratio of the volumes $V_i:V_f$ is substantially equal to the ratio of the pressures $P_f:P_i$. An engineer having ordinary skill in the art will be able to select suitable values for the volumes $V_i$ and $V_f$ using the description and equation given above. For example, if the initial pressure $P_i$ in the vessel is equal to standard atmospheric pressure of about 14 psi, the desired final pressure $P_f$ is equal to 26 psi (the desired 12 psi above ambient pressure), and the initial volume capacity $V_i$ is equal to 500 l, then the heat sealing of the vessel should reduce the volume capacity to a volume $V_f$ of about 275 l. This is just one example of suitable values for the initial and final volumes, and it is to be understood that the scope of the invention is not limited to this example. Many other suitable values may be selected to achieve the desired ratios, as will be apparent to one having ordinary skill in the art.

The various embodiments of the system of the present invention may find use in many applications. The system may be utilized to perform chemical reactions on samples, e.g., nucleic acid amplification, and to optically detect amplified target sequences. Although amplification by PCR has been described herein, it will be appreciated by persons skilled in the art that the system may be utilized for a variety of other polynucleotide amplification reactions and ligand-binding assays. Such additional reactions may be thermally cycled or they may be carried out at a single temperature, e.g., isothermal nucleic acid amplification. Other applications of the system are intended to be within the scope of the invention where those applications require temperature control of a sample and/or optical detection.

Summary, Ramifications, and Scope

Although the above description contains many specificities, these should not be construed as limitations on the scope of the invention, but merely as examples of some of the presently preferred embodiments. Many modifications or substitutions may be made to the system and methods described without departing from the scope of the invention. For example, in one alternative embodiment, the reaction vessel has only one flexible sheet forming a major wall of the reaction chamber. The rigid frame defines the other major wall of the chamber, as well as the side walls of the chamber. In this embodiment, the major wall formed by the frame should have a minimum thickness of about 0.05 inches (the practical minimum thickness for injection molding), while the flexible sheet may be as thin as 0.0005 inches. The advantage to this embodiment is that the manufacturing of the reaction vessel is simplified, and hence less expensive, since only one flexible sheet need be attached to the frame. The disadvantage is that the heating and cooling rates of the sample are likely to be slower since the major wall formed by the frame will probably not permit as high a rate of heat transfer as the thin, flexible sheet.

In some embodiments, the system may have just one thermal surface for contacting a flexible wall of the reaction vessel and one thermal element for heating and/or cooling the thermal surface. The advantage to using one thermal surface and one thermal element is that the system may be manufactured less expensively. The disadvantage is that the heating and cooling rates are likely to be about twice as slow. Further, although it is presently preferred that the thermal surfaces be formed by thermally conductive plates, each thermal surface may be provided by any rigid structure having a contact area for contacting a wall of the vessel. The thermal surface preferably comprises a material having a high thermal conductivity, such as ceramic or metal. Moreover, the thermal surface may comprise the surface of the thermal element itself. For example, the thermal surface may be the surface of an ultrasonic transducer that contacts the flexible wall of the chamber for ultrasonic heating and/or lysing of the sample in the chamber. Alternatively, the thermal surface may be the surface of a thermoelectric device that contacts the wall to heat and/or cool the chamber. In addition, the vessel may have a heated lid or cap.

The filters used in the optics assemblies may be designed to provide excitation and emission light in any wavelength ranges of interest, not just the specific wavelength ranges described above. The choice of fluorescent dyes for any given application depends upon the analytes of interest. One skilled in the art will realize that different combinations of light sources, filters, or filter wavelengths may be used to accommodate the different peak excitation and emission spectra of the selected dyes. Moreover, although blue and green light sources are presently preferred, different color light sources, such as blue-green, red, or amber LEDs, may be used in the system. Further, infrared or ultraviolet light sources may be used.

Moreover, although fluorescence excitation and emission detection is a preferred embodiment, optical detection methods such as those used in absorption and/or transmission with on-axis geometries may also be applied to the system of the present invention. Alternative geometries, such as on-axis alignments of light sources and detectors, can be used to monitor changes in dye concentrations and physical conditions (temperature, pH, etc.) of a reaction by measuring absorption of the illumination. The optics may also be used to measure time decay fluorescence. Additionally, the optics are not limited to detection based upon fluorescent labels. The optics system may be applicable to detection based upon phosphorescent labels, chemiluminescent labels, or electrochemiluminescent labels.

The scope of the invention should, therefore, be determined not with reference to the above description, but instead should be determined with reference to the appended claims along with their full scope of equivalents.

What is claimed is:

1. A system for controlling the temperature of a sample, the system comprising:
 a) a reaction vessel having:
  i) a reaction chamber defined by two opposing major walls and side walls connecting the major walls to each other, at least one of the major walls comprising a sheet or film;
  ii) a loading reservoir for receiving the sample prior to loading the sample into the reaction chamber, the loading reservoir being connected to the reaction chamber via a first channel; and
  iii) an aspiration port connected to the reaction chamber via a second channel;
 b) an aspiration device for establishing a seal with the aspiration port and for drawing the sample from the loading reservoir into the reaction chamber, wherein the vessel further includes flow control means for preventing substantial flow of the sample from the loading reservoir into the reaction chamber until the sample is drawn into the chamber by the aspiration device;
 c) at least one heating or cooling surface for contacting the sheet or film, the sheet or film being sufficiently flexible to conform to the surface; and d) at least one thermal element for heating or cooling the surface to induce a temperature change in the reaction chamber.

2. The system of claim 1, wherein the flow control means comprises at least one portion of the first channel having a sufficiently small width or diameter to prevent substantial flow of the sample from the loading reservoir to the chamber until the sample is drawn into the chamber by the aspiration device.

3. The system of claim 1, wherein the flow control means comprises at least one valve in the first channel.

4. The system of claim 1, wherein the flow control means comprises at least one membrane or screen in the first channel.

5. The system of claim 1, wherein the system includes at least two heating or cooling surfaces positioned to receive the vessel between them such that the surfaces contact the major walls, and wherein each of the major walls comprises a flexible sheet or film.

6. The system of claim 5, wherein the heating or cooling surfaces are the surfaces of opposing plates positioned to receive the vessel between them, each of the plates having a thermal mass less than 1 J/° C.

7. The system of claim 1, wherein each of the plates comprises a ceramic material, and wherein the at least one thermal element comprises heating elements coupled to the plates.

8. The system of claim 1, wherein at least two of the side walls of the chamber are optically transmissive, and wherein the system further includes optics for optically interrogating the chamber while the sheet or film is in contact with the heating or cooling surface, the optics comprising at least one light source for transmitting light to the chamber through a first one of the optically transmissive walls and at least one detector for detecting light exiting the chamber through a second one of the optically transmissive walls.

9. The system of claim 8, wherein the optically transmissive walls are angularly offset from each other by about 90°.

10. The system of claim 9, further comprising at least one controller for controlling the operation of the thermal element, light source, and detector.

11. The system of claim 1, wherein the chamber has a thickness less than the width or diameter of the aspiration device.

12. The system of claim 1, wherein the ratio of the width of the chamber to the thickness of the chamber is at least 4:1, and wherein the thickness of the chamber is less than or equal to 3 mm.

13. The system of claim 1, further comprising means for increasing the pressure in the chamber, wherein the pressure increase in the chamber is sufficient to force the sheet or film to conform to the surface.

14. The system of claim 13, wherein the vessel further includes a seal aperture extending over an outer end of the loading reservoir and an outer end of the aspiration port, and wherein the means for increasing the pressure in the chamber comprises a plug that is insertable into the aperture to compress gas in the vessel.

15. The system of claim 14, wherein the vessel includes an inner surface defining the seal aperture, and wherein the inner surface has at least one pressure control groove formed therein, the pressure control groove extending to a predetermined depth in the aperture to allow gas to escape from the aperture until the plug reaches the predetermined depth.

16. The system of claim 15, further comprising an automated machine for inserting the plug into the aperture, wherein the machine has a machine tip for engaging the plug, and wherein the plug includes a cap having an engagement aperture for receiving and establishing a fit with the machine tip.

17. The system of claim 14, wherein the plug includes a cap having latches, and wherein the vessel further comprises catches for engaging the latches, thereby securing the plug in the aperture.

18. The system of claim 13, wherein the means for increasing the pressure in the chamber comprises first and second plugs which are inserted into the loading reservoir and the aspiration port, respectively, to compress gas in the vessel and increase pressure in the chamber.

19. The system of claim 13, wherein the means for increasing pressure in the chamber comprises:
i) a machine head for communicating with the vessel; and
ii) a pressure source for pressurizing the chamber through the machine head.

20. The system of claim 19, wherein the vessel further includes a seal aperture extending over an outer end of the loading reservoir and an outer end of the aspiration port, the system further comprises an adapter for placing the machine head in fluid communication with the chamber, and the adapter is sized to be inserted into the aperture.

21. The system of claim 20, wherein the adapter includes a valve for preventing fluid from escaping from the vessel.

22. The system of claim 13, wherein the vessel further includes a seal aperture extending over an outer end of the loading reservoir and an outer end of the aspiration port, and wherein the means for increasing pressure in the chamber comprises:
i) an elastomeric plug for sealing the aperture; and
ii) a needle for injecting fluid into the vessel through the plug.

23. The system of claim 13, wherein the vessel further includes a seal aperture extending over an outer end of the loading reservoir and an outer end of the aspiration port, and wherein the means for increasing pressure in the chamber comprises a platen for heat sealing a film or foil to the vessel to seal the aperture.

24. The system of claim 1, further comprising a pick-and-place machine having a machine tip for engaging the vessel, wherein either the loading reservoir or the aspiration port has tapered walls for establishing a fit with the machine tip, thereby enabling the machine tip to pick and place the vessel.

25. A system for controlling the temperature of a sample, the system comprising:
a) a reaction vessel having:
i) a reaction chamber;
ii) a loading reservoir for receiving the sample, wherein the loading reservoir is connected to the reaction chamber via a first channel;
iii) an aspiration port connected to the reaction chamber via a second channel; and
iv) a seal aperture extending over an outer end of the loading reservoir and an outer end of the aspiration port;
b) an aspiration device for establishing a seal with the aspiration port and for drawing the sample from the loading reservoir into the reaction chamber, wherein the vessel further includes flow control means for preventing substantial flow of the sample from the loading reservoir into the reaction chamber until the sample is drawn into the reaction chamber by the aspiration device;
c) a plug that is insertable into the aperture; and d) at least one thermal element for heating or cooling the reaction chamber.

26. The system of claim 25, wherein the flow control means comprises at least one portion of the first channel having a sufficiently small width or diameter to prevent substantial flow of the sample from the loading reservoir to the chamber until the sample is drawn into the chamber by the aspiration device.

27. The system of claim 25, wherein the flow control means comprises at least one valve in the first channel.

28. The system of claim 25, wherein the flow control means comprises at least one membrane or screen in the first channel.

29. The system of claim 25, wherein the reaction chamber is defined by two opposing major walls and side walls connecting the major walls to each other, at least one of the major walls comprises a sheet or film, and the at least one thermal element comprises:
   i) at least one heating or cooling surface for contacting the sheet or film, the sheet or film being sufficiently flexible to conform to the surface; and
   ii) means for heating or cooling the surface.

30. The system of claim 25, wherein the vessel includes a rigid frame defining side walls of the chamber, the vessel includes two sheets or films attached to opposite sides of the frame to form two opposing major walls of the chamber, and the at least one thermal element comprises:
   i) opposing plates positioned to receive the vessel between them such that the plates contact the major walls; and
   ii) means for heating or cooling the plates.

31. The system of claim 30, wherein each of the plates comprises a ceramic material, and wherein each of the plates has a thickness less than or equal to 1 mm.

32. The system of claim 30, wherein the means for heating or cooling the plates comprises resistive heating elements coupled to the plates.

33. The system of claim 30, wherein each of the plates has a thermal mass less than or equal to 1 J/° C.

34. The system of claim 25, wherein the reaction chamber is defined by a plurality of walls, at least two of the walls are optically transmissive, and the system further comprises optics for optically interrogating the chamber, the optics comprising at least one light source for transmitting light to the chamber through a first one of the optically transmissive walls and at least one detector for detecting light exiting the chamber through a second one of the optically transmissive walls.

35. The system of claim 34, wherein the optically transmissive walls are angularly offset from each other by about 90°.

36. The system of claim 34, further comprising at least one controller for controlling the operation of the thermal element, light source, and detector.

37. The system of claim 25, wherein the reaction chamber has a thickness less than the width or diameter of the aspiration device.

38. The system of claim 25, wherein the ratio of the width the reaction chamber to the thickness of the reaction chamber is at least 4:1, and wherein the thickness of the reaction chamber is less than or equal to 3 mm.

39. The system of claim 25, wherein the plug is sized to compress gas in the vessel, thereby increasing pressure in the reaction chamber to at least 2 pounds per square inch above ambient pressure.

40. The system of claim 25, further comprising an automated machine for inserting the plug into the aperture, wherein the machine has a machine tip for engaging the plug, and wherein the plug includes a cap having an engagement aperture for receiving the machine tip.

41. The system of claim 25, wherein the plug includes a cap having latches, and wherein the vessel further comprises catches for engaging the latches, thereby securing the plug in the aperture.

42. A system for loading a sample into a reaction vessel and for controlling the temperature of the sample in the vessel, wherein the vessel includes a reaction chamber, a loading reservoir connected to the reaction chamber via a first channel, an aspiration port connected to the reaction chamber via a second channel, and a seal aperture extending over an outer end of the loading reservoir and an outer end of the aspiration port, the system comprising:
   a) an aspiration and dispensing device for dispensing the sample into the loading reservoir, for establishing a seal with the aspiration port, and for drawing the sample from the loading reservoir into the reaction chamber, wherein the vessel includes flow control means for preventing substantial flow of the sample from the loading reservoir into the reaction chamber until the sample is drawn into the reaction chamber by the aspiration and dispensing device;
   b) an automated machine for inserting a plug into the seal aperture after loading the sample into the chamber; and
   c) at least one thermal element for heating or cooling the reaction chamber.

43. The system of claim 42, wherein the flow control means comprises at least one portion of the first channel having a sufficiently small width or diameter to prevent substantial flow of the sample from the loading reservoir to the chamber until the sample is drawn into the chamber by the aspiration device.

44. The system of claim 42, wherein the flow control means comprises at least one valve in the first channel.

45. The system of claim 42, wherein the flow control means comprises at least one membrane or screen in the first channel.

46. The system of claim 42, wherein the at least one thermal element comprises:
   i) opposing plates positioned to receive the vessel between them such that the plates contact major walls of the reaction chamber; and
   ii) means for heating or cooling the plates.

47. The system of claim 46, wherein each of the plates comprises a ceramic material, and wherein each of the plates has a thickness less than or equal to 1 mm.

48. The system of claim 46, wherein the means for heating or cooling the plates comprises resistive heating elements coupled to the plates.

49. The system of claim 46, wherein each of the plates has a thermal mass less than or equal to 1 J/° C.

50. The system of claim 42, wherein the reaction chamber is defined by a plurality of walls, at least two of the walls are optically transmissive, and the system further comprises optics for optically interrogating the chamber, the optics comprising at least one light source for transmitting light to the chamber through a first one of the optically transmissive walls and at least one detector for detecting light exiting the chamber through a second one of the optically transmissive walls.

51. The system of claim 50, further comprising at least one controller for controlling the operation of the thermal element, light source, and detector.

52. A reaction vessel comprising:
a) a reaction chamber defined by two opposing major walls and side walls connecting the major walls to each other, wherein at least one of the major walls comprises a sheet or film sufficiently flexible to conform to a heating or cooling surface, and wherein at least two of the side walls are optically transmissive to provide optical windows to the reaction chamber;
b) a loading reservoir for receiving the sample prior to loading the sample into the reaction chamber, wherein the loading reservoir is connected to the reaction chamber via a first channel; and
c) an aspiration port for establishing a seal with an aspiration device, the aspiration port being connected to the reaction chamber via a second channel, thereby enabling the aspiration device to draw the sample from the loading reservoir into the chamber, wherein the vessel further includes flow control means for preventing substantial flow of the sample from the loading reservoir into the reaction chamber until the sample is drawn into the reaction chamber by the aspiration device.

53. The vessel of claim 52, wherein the flow control means comprises at least one portion of the first channel having a sufficiently small width or diameter to prevent substantial flow of the sample from the loading reservoir to the reaction chamber until the sample is drawn into the reaction chamber by the aspiration device.

54. The vessel of claim 52, wherein the flow control means comprises at least one valve in the first channel.

55. The vessel of claim 52, wherein the flow control means comprises at least one membrane or screen in the first channel.

56. The vessel of claim 52, wherein the vessel includes a rigid frame defining the side walls, each of the two opposing major walls comprises a flexible sheet or film attached to the frame, and the vessel includes a loading structure extending from the frame, the loading structure defining the loading reservoir and the aspiration port.

57. The vessel of claim 52, wherein the optically transmissive walls are angularly offset from each other by about 90°.

58. The vessel of claim 52, wherein the ratio of the width the reaction chamber to the thickness of the reaction chamber is at least 4:1, and wherein the thickness of the reaction chamber is less than or equal to 3 mm.

59. The vessel of claim 52, further comprising:
i) a seal aperture extending over an outer end of the loading reservoir and an outer end of the aspiration port; and
ii) a plug that is insertable into the aperture.

60. The vessel of claim 59, wherein the plug is sized to compress gas in the vessel, thereby increasing pressure in the reaction chamber.

61. The vessel of claim 59, wherein the vessel includes an inner surface defining the seal aperture, and wherein the inner surface has at least one pressure control groove formed therein, the pressure control groove extending to a predetermined depth in the aperture to allow gas to escape from the aperture until the plug reaches the predetermined depth.

62. The vessel of claim 52, wherein the plug includes a cap having an engagement aperture for receiving and establishing a fit with a machine tip.

63. The vessel of claim 52, wherein the plug includes a cap having latches, and wherein the vessel further comprises catches for engaging the latches, thereby securing the plug in the aperture.

64. The vessel of claim 52, wherein either the loading reservoir or the aspiration port has tapered walls for establishing a fit with a machine tip, thereby enabling the machine tip to pick and place the vessel.

65. The vessel of claim 52, further comprising dried or lyophilized reagents in the reaction chamber.

66. A reaction vessel comprising:
a) a reaction chamber;
b) a loading reservoir for receiving the sample prior to loading the sample into the reaction chamber, the loading reservoir being connected to the chamber via a first channel;
c) an aspiration port for establishing a seal with an aspiration device, the aspiration port being connected to the reaction chamber via a second channel thereby enabling the aspiration device to draw the sample from the loading reservoir into the reaction chamber, wherein the vessel further includes flow control means for preventing substantial flow of the sample from the loading reservoir into the reaction chamber until the sample is drawn into the reaction chamber by the aspiration device; and
d) a seal aperture, extending over an outer end of the loading reservoir and an outer end of the aspiration port, for receiving a plug that is inserted into the aperture after loading the sample into the reaction chamber.

67. The vessel of claim 66, wherein the flow control means comprises at least one portion of the first channel having a sufficiently small width or diameter to prevent substantial flow of the sample from the loading reservoir to the reaction chamber until the sample is drawn into the reaction chamber by the aspiration device.

68. The vessel of claim 66, wherein the flow control means comprises at least one valve in the first channel.

69. The vessel of claim 66, wherein the flow control means comprises at least one membrane or screen in the first channel.

70. The vessel of claim 66, wherein the reaction chamber is defined by two opposing major walls and side walls connecting the major walls to each other, and wherein at least one of the major walls comprises a sheet or film sufficiently flexible to conform to a heating or cooling surface.

71. The vessel of claim 70, wherein at least two of the side walls are optically transmissive to provide optical windows to the reaction chamber.

72. The vessel of claim 70, wherein the vessel includes a rigid frame defining the side walls, each of the two opposing major walls comprises a flexible sheet or film attached to the frame, and the vessel includes a loading structure extending from the frame, the loading structure defining the loading reservoir and the aspiration port.

73. The vessel of claim 71, wherein the optically transmissive walls are angularly offset from each other by about 90°.

74. The vessel of claim 66, wherein the ratio of the width the reaction chamber to the thickness of the reaction chamber is at least 4:1, and wherein the thickness of the reaction chamber is less than or equal to 3 mm.

75. The vessel of claim 66, wherein the plug is sized to compress gas in the vessel, thereby increasing pressure in the reaction chamber.

76. The vessel of claim 66, wherein the pressure increase is at least 2 pounds per square inch.

77. The vessel of claim 66, wherein the pressure increase is in the range of 8 to 15 pounds per square inch.

78. The vessel of claim 66, wherein the vessel includes an inner surface defining the seal aperture, and wherein the inner surface has at least one pressure control groove formed therein, the pressure control groove extending to a predetermined depth in the aperture to allow gas to escape from the aperture until the plug reaches the predetermined depth.

79. The vessel of claim 66, wherein the plug includes a cap having an engagement aperture for receiving and establishing a fit with a machine tip.

80. The vessel of claim 66, wherein the plug includes a cap having latches, and wherein the vessel further comprises catches for engaging the latches, thereby securing the plug in the aperture.

81. The vessel of claim 66, wherein either the loading reservoir or the aspiration port has tapered walls for establishing a fit with a machine tip, thereby enabling the machine tip to pick and place the vessel.

82. The vessel of claim 66, further comprising dried or lyophilized reagents in the reaction chamber.

* * * * *